(12) United States Patent
Naya et al.

(10) Patent No.: US 6,885,454 B2
(45) Date of Patent: Apr. 26, 2005

(54) MEASURING APPARATUS

(75) Inventors: Masayuki Naya, Kaisei-machi (JP);
Nobufumi Mori, Kaisei-machi (JP);
Toshihito Kimura, Kaisei-machi (JP);
Hitoshi Shimizu, Kaisei-machi (JP);
Shu Sato, Kaisei-machi (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 249 days.

(21) Appl. No.: 10/108,258

(22) Filed: Mar. 28, 2002

(65) Prior Publication Data
US 2002/0140938 A1 Oct. 3, 2002

(30) Foreign Application Priority Data

Mar. 28, 2001 (JP) ........................................ 2001-093085
Feb. 12, 2002 (JP) ........................................ 2002-034136

(51) Int. Cl.[7] .................. G01N 21/55; G01N 21/41; H04J 14/08; G02B 26/08; G02B 17/00
(52) U.S. Cl. ..................... 356/445; 356/134; 356/136; 359/136; 359/212; 359/595
(58) Field of Search ................ 356/134, 136, 356/139.08, 139.01, 141.1, 141.5, 400, 445, 145; 359/136, 212, 222, 595, 598

(56) References Cited

U.S. PATENT DOCUMENTS

| | | | | |
|---|---|---|---|---|
| 5,055,265 A | * | 10/1991 | Finlan | |
| 5,064,619 A | * | 11/1991 | Finlan | |
| 5,255,075 A | * | 10/1993 | Cush | |
| 5,485,277 A | * | 1/1996 | Foster | |
| 5,822,073 A | * | 10/1998 | Yee et al. | |
| 5,991,048 A | * | 11/1999 | Karlson et al. | |
| 2001/0040130 A1 | * | 11/2001 | Lorch et al. | |

FOREIGN PATENT DOCUMENTS

JP 6-167443 6/1994

OTHER PUBLICATIONS

Takayuki Okamoto, "Spectral Researches" vol. 47, No. 1, Dec. 8, 1998, pp. 21–23, 26–27.

* cited by examiner

Primary Examiner—Frank G. Font
Assistant Examiner—Khaled Brown
(74) Attorney, Agent, or Firm—Sughrue Mion, PLLC

(57) ABSTRACT

A measuring apparatus is disclosed which includes a measuring unit equipped with a dielectric block and a thin film layer; an incidence system for making a light beam enter the dielectric block so that a condition for total internal reflection is satisfied at an interface between the dielectric block and the thin film layer; and a photodetector for receiving the light beam totally reflected at the interface. The measuring unit is measured a plurality of times, and a change in the state of attenuated total reflection during the plurality of measurements is detected. The sensor further includes a tilt measurement section for measuring the longitudinal tilt of the interface which changes the incidence angles during the plurality of measurements, and a calculating section for obtaining a measured value in which errors due to the longitudinal tilt have been corrected.

27 Claims, 35 Drawing Sheets

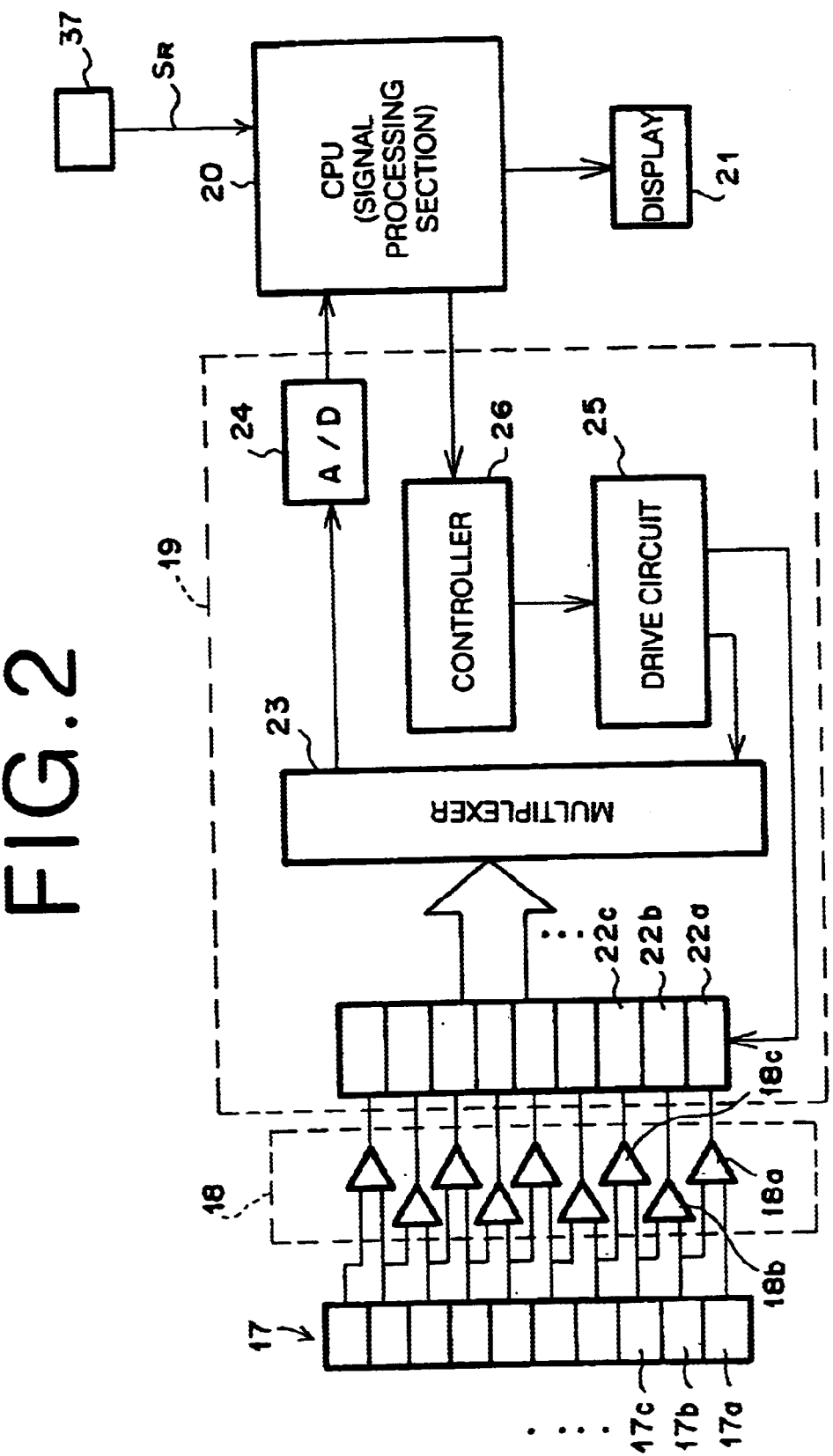

FIG.3A
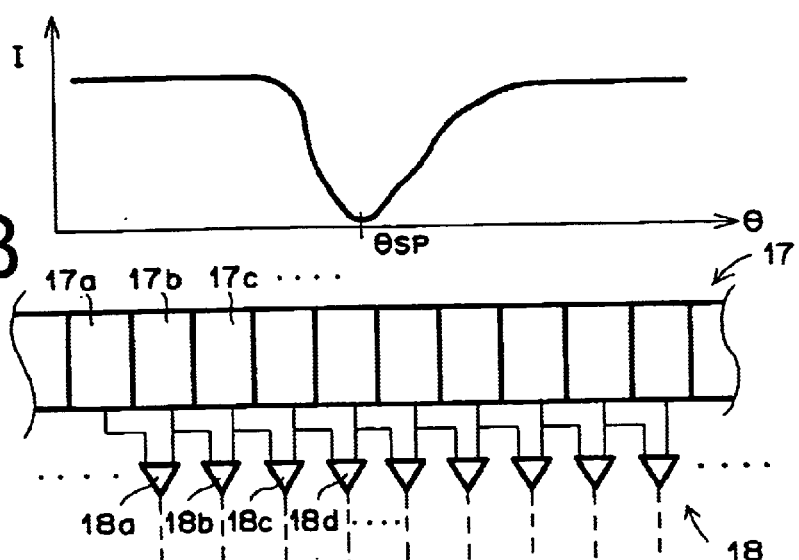
FIG.3B
FIG.3C
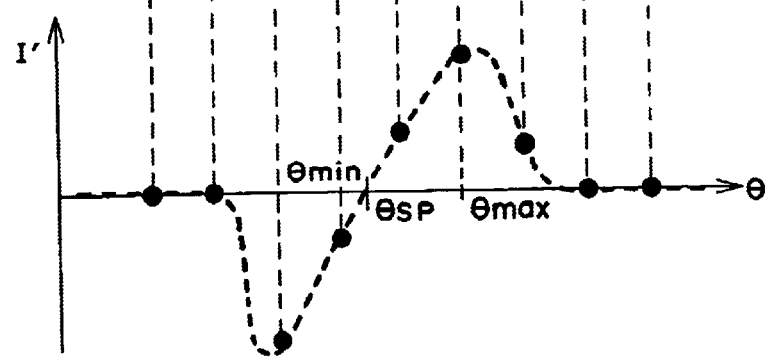

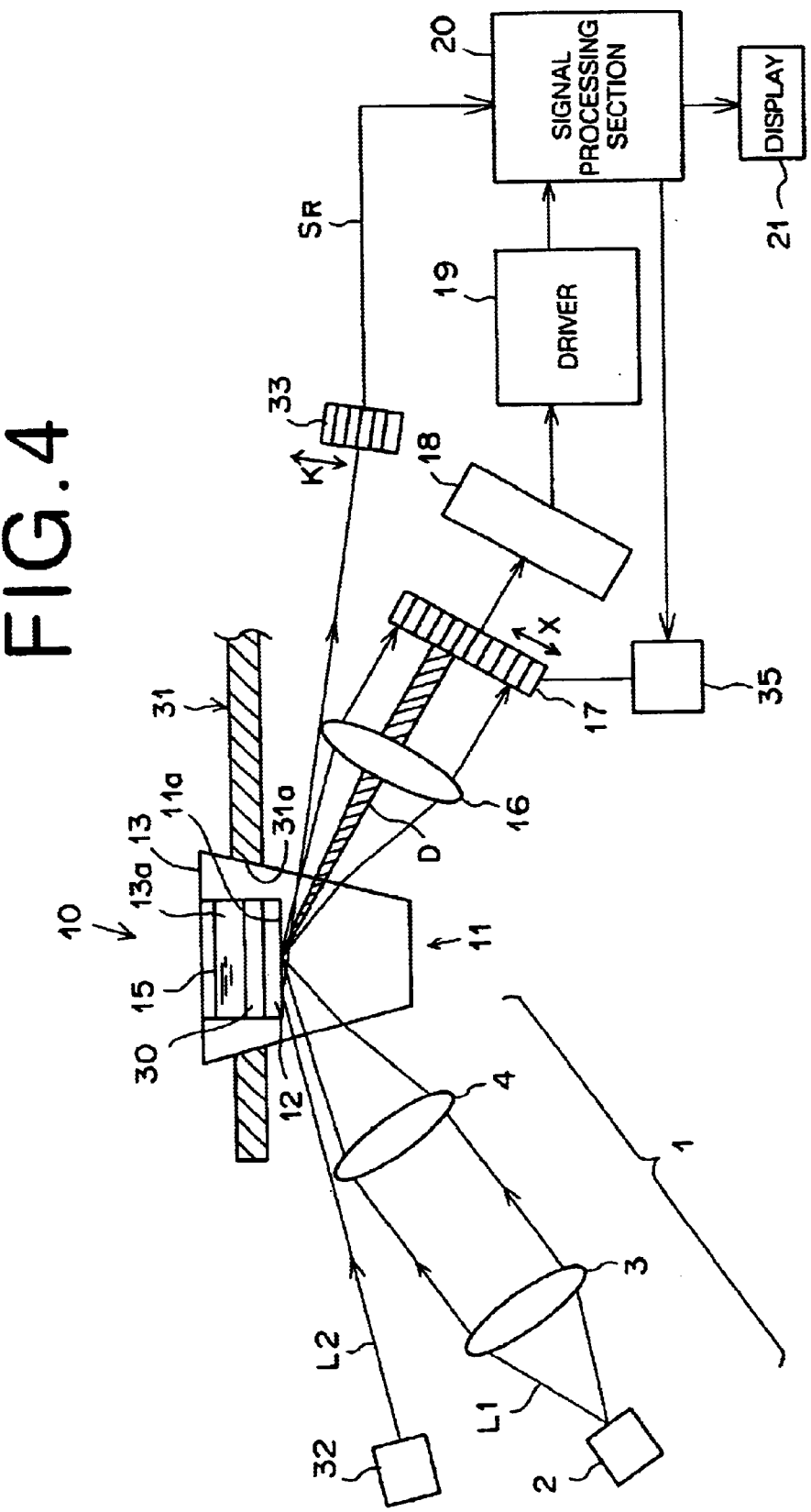

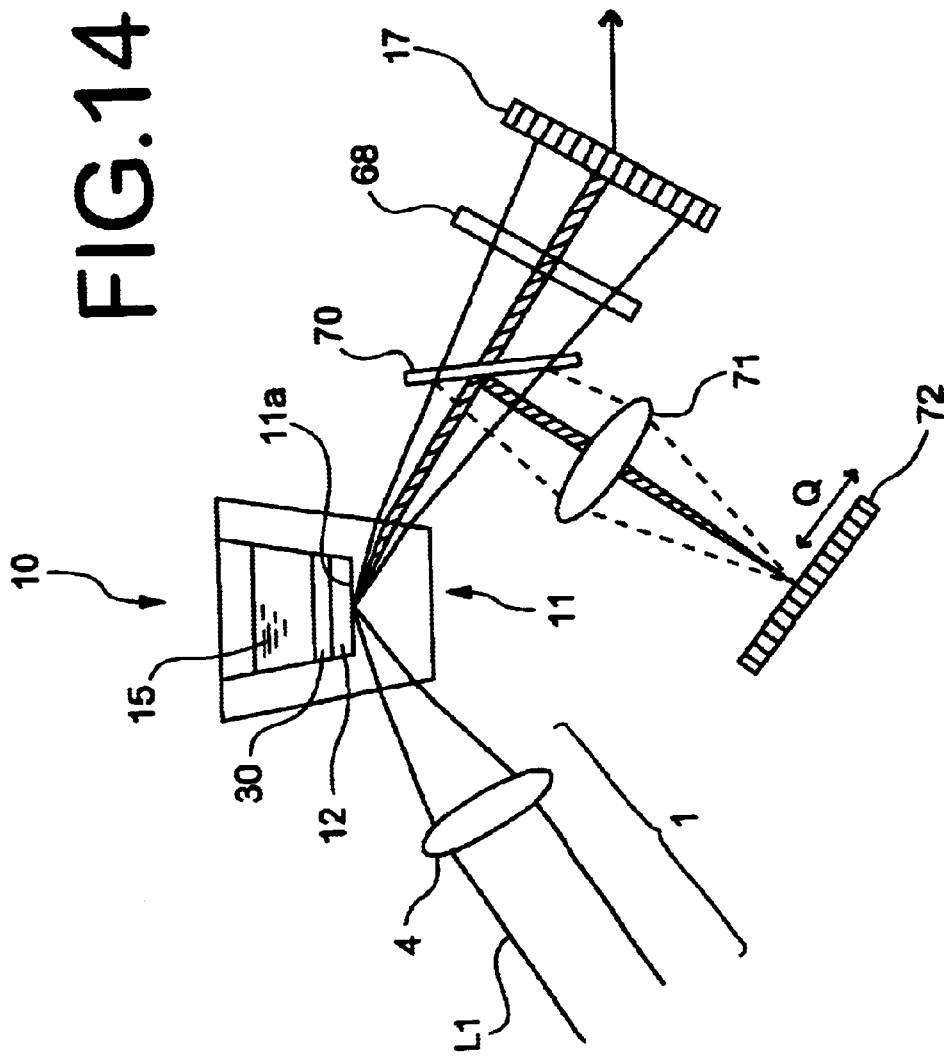

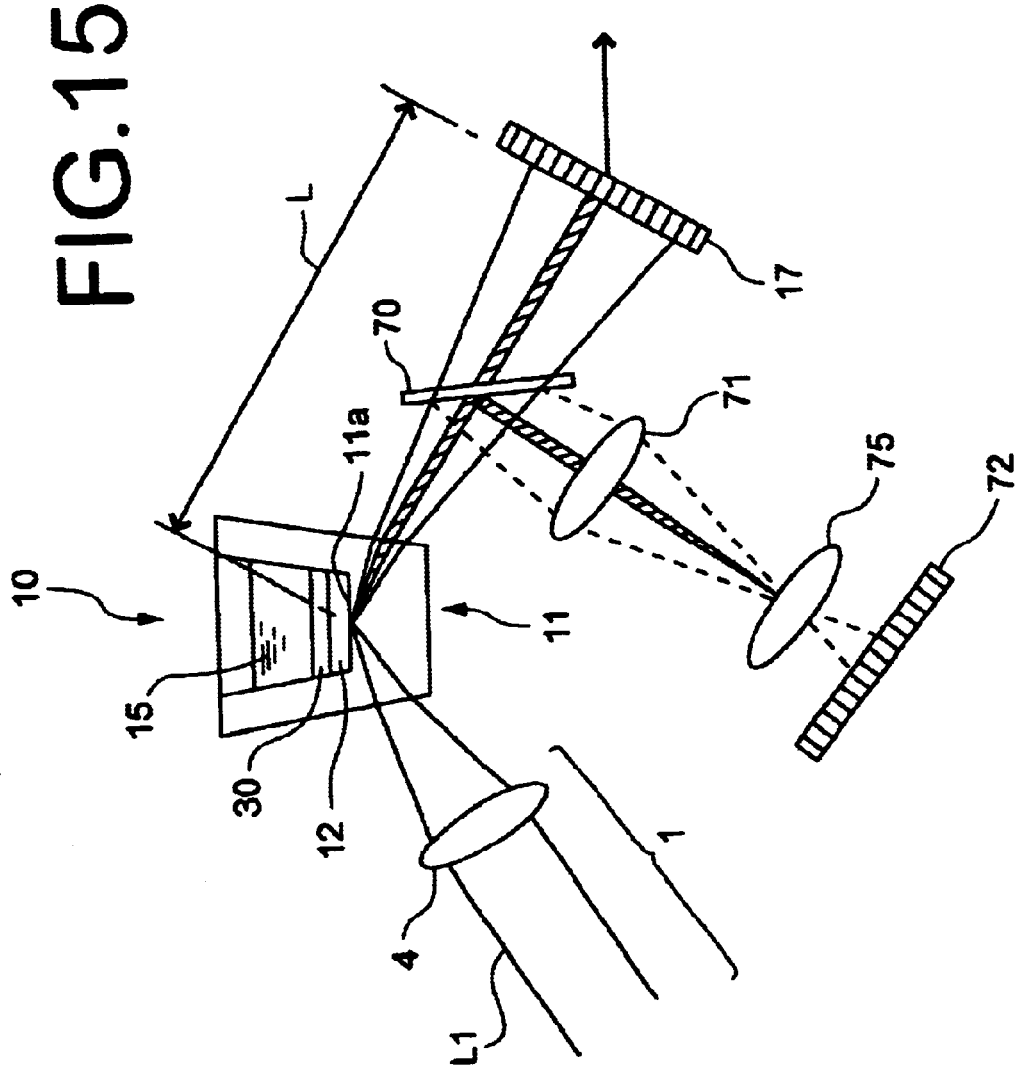

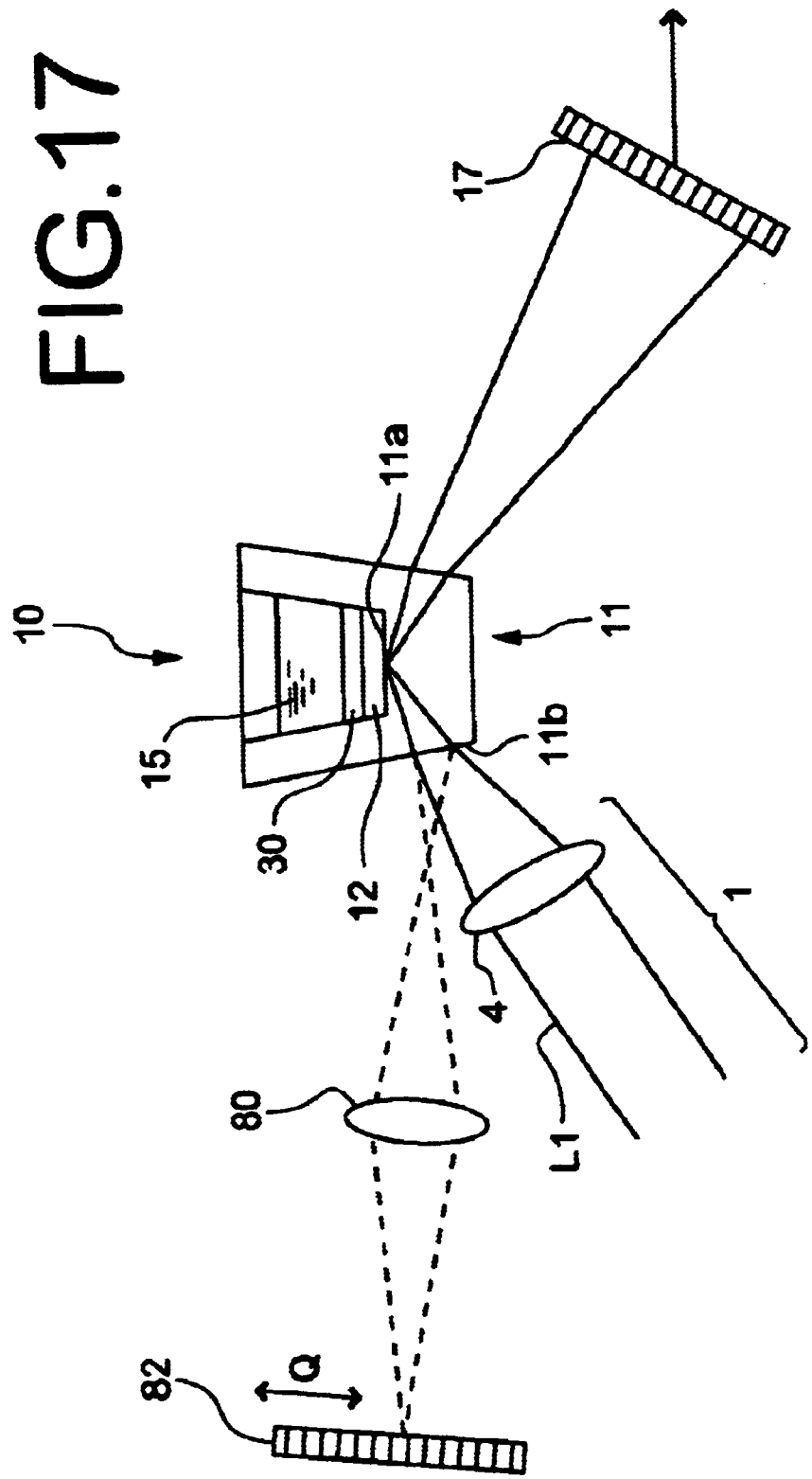

MEASURING APPARATUS

BACKGROUND OF THE INVENTION

1. Field of the Invention

The present invention relates to a measuring apparatus such as a surface plasmon resonance sensor for quantitatively analyzing a substance in a sample by utilizing the excitation of surface plasmon.

2. Description of the Related Art

In metals, if free electrons are caused to vibrate in a group, a compression wave called a plasma wave will be generated. The compression wave, generated in the metal surface and quantized, is called surface plasmon.

There have hitherto been proposed various kinds of surface plasmon resonance sensors for quantitatively analyzing a substance in a sample by taking advantage of a phenomenon that surface plasmon is exited by a light wave. Among such sensors, one employing a system called "Kretschmann configuration" is particularly well known (e.g., see Japanese Unexamined Patent Publication No. 6(1994)-167443).

The surface plasmon resonance sensor employing the "Kretschmann configuration" is equipped with a dielectric block formed, for example, into the shape of a prism; a metal film, formed on one surface of the dielectric block, for placing a sample thereon; and a light source for emitting a light beam. The surface plasmon resonance sensor is further equipped with an optical system for making the light beam enter the dielectric block so that a condition for total internal reflection (TIR) is satisfied at the interface between the dielectric block and the metal film and that various angles of incidence, including a surface plasmon resonance condition, are obtained; and photodetection means for measuring the intensity of the light beam satisfying TIR at the interface, and detecting surface plasmon resonance, that is, attenuated total reflection (ATR).

To obtain various angles of incidence in the aforementioned manner, a relatively thin light beam can be emitted so that it strikes the above-mentioned interface at different angles of incidence, or a relatively thick beam can be emitted so that it strikes the interface convergently or divergently. In the former, the light beam whose reflection angle varies with the incidence angle thereof can be detected by a small photodetector that is moved in synchronization with the reflection angle variation, or by an area sensor extending along a direction where the reflection angle varies. In the latter, on the other hand, the light beam can be detected by an area sensor extending in a direction where all the light beam components reflected at various angles are received.

In the surface plasmon resonance sensor mentioned above, an evanescent wave with electric field distribution is generated in a sample in contact with the metal film, if a light beam strikes the metal film at a specific incidence angle $\theta_{sp}$ greater than a critical incidence angle at which total internal reflection (TIR) takes place. The generated evanescent wave excites surface plasmon at the interface between the metal film and the sample. When the wave vector of the evanescent wave is equal to the wave number of the surface plasmon and therefore the wave numbers between the two are matched, the evanescent wave resonates with the surface plasmon and the light energy is transferred to the surface plasmon, whereby the intensity of the light satisfying TIR at the interface between the dielectric block and the metal film drops sharply. This sharp intensity drop is generally detected as a dark line by the above-mentioned photodetection means.

Note that the above-mentioned resonance occurs only when an incident light beam is a p-polarized light beam. Therefore, in order to make the resonance occur, it is necessary to make a p-polarized light beam strike the interface, or to detect only the p-polarized light component of an incident light beam.

If the wave number of the surface plasmon is found from the specific incidence angle $\theta_{sp}$ at which ATR takes place, the dielectric constant of a sample to be analyzed can be calculated by the following Equation:

$$K_{sp}(\omega) = (\omega/c)\{\epsilon_m(\omega)\epsilon_s\}^{1/2}/\{\epsilon_m(\omega)+\epsilon_s\}^{1/2}$$

where $K_{sp}$ represents the wave number of the surface plasmon, $\omega$ represents the angular frequency of the surface plasmon, c represents the speed of light in vacuum, and $\epsilon_m$ and $\epsilon_s$ represent the dielectric constants of the metal and the sample, respectively.

If the dielectric constant $\epsilon_s$ of a sample is found, the density of a specific substance in the sample is found based on a predetermined calibration curve, etc. As a result, the specific substance in the sample can be quantitatively analyzed by finding the specific incidence angle $\theta_{sp}$ at which the intensity of the reflected light at the interface drops sharply.

As a similar sensor making use of ATR, there is a leaky mode sensor (e.g., see "Spectral Researches," Vol. 47, No. 1 (1998), pp. 21 to 23 and pp. 26 to 27). This leaky mode sensor is equipped with a dielectric block formed, for example, into the shape of a prism; a cladding layer formed on one surface of the dielectric block; and an optical waveguide layer, formed on the cladding layer, for placing a sample thereon. The leaky mode sensor is further equipped with a light source for emitting a light beam; an optical system for making the light beam enter the dielectric block at various angles of incidence so that a condition for total internal reflection (TIR) is satisfied at the interface between the dielectric block and the cladding layer and that ATR occurs by a waveguide mode excited in the optical waveguide layer; and photodetection means for measuring the intensity of the light beam totally reflected at the interface between the dielectric block and the cladding layer, and detecting the excited state of the waveguide mode, that is, ATR.

In the leaky mode sensor mentioned above, if a light beam strikes the cladding layer through the dielectric block at incidence angles greater than a critical incidence angle at which TIR takes place, the light beam is transmitted through the cladding layer and then only light with a specific wave number, incident at a specific incidence angle, propagates through the optical waveguide layer in a waveguide mode. If the waveguide mode is excited in this manner, the greater part of the incident light is confined within the optical waveguide layer, and consequently, ATR occurs in which the intensity of light totally reflected at the above-mentioned interface drops sharply. Since the wave number of the light propagating through the optical waveguide layer depends on the refractive index of a sample on the optical waveguide layer, both the refractive index of the sample and the properties of the sample related to the refractive index thereof can be analyzed by finding the above-mentioned specific incidence angle $\theta_{sp}$ at which ATR takes place.

Note that there are several types of measuring apparatuses utilizing TIR, such as the surface plasmon sensor or the leaky mode sensor, wherein light is made incident on an interface at an incidence angle in which conditions for TIR are obtained, and qualitative analysis is performed on a sample by measuring the change in the state of light totally reflected at the interface due to the evanescent waves generated by the light, other than those that measure the specific incidence angle at which ATR occurs. For example, there are those that make light beams of a plurality of wavelengths incident on an interface, and measure the degree of ATR for each wavelength, or those that divide a portion of a light beam made incident on an interface before the light beam enters the interface, and make the divided light beam interfere with the light beam reflected at the interface, and measure the state of said interference, etc.

In the conventional surface plasmon resonance sensor or leaky mode sensor of the type described above, when a single sample (the same measuring unit) is measured a plurality of times at predetermined time intervals in order to examine a change in the state thereof, there are cases where the sample and the dielectric body are both exchanged to efficiently measure a plurality of samples. In this case, if one sample is removed from the measuring apparatus and then the sample is again set, there is a disadvantage that difference (tilt) will occur between the first base line (aforementioned interface) and the next base line. If the tilt of the base line is a longitudinal tilt that changes the incidence angle of a light beam, the angle of the reflected light being measured will be shifted, resulting in a reduction in the measurement accuracy.

In addition, even when a sample is not exchanged, there are cases where the tilt of the base line changes slightly due to vibration, etc., when a table with a plurality of samples is being rotated. In such a case, the tilt of the base line during a plurality of measurements causes errors in measurement.

Furthermore, if the transverse tilt of the interface which shifts the angle of reflected light, as well as the longitudinal tilt of the interface which changes the incidence angle of the light beam, occurs, there are cases where the reflection direction of reflected light changes and therefore the reflected light cannot be received by the light-receiving surface of photodetection means. Thus, the longitudinal and transverse tilts of the interface result in a reduction in the accuracy of measurement.

SUMMARY OF THE INVENTION

The present invention has been made in view of the circumstances mentioned above. Accordingly, it is the primary object of the present invention to provide a measuring apparatus which has high accuracy of measurement even when measuring the same measuring unit a plurality of times.

To achieve this end and in accordance with the present invention, there is provided a first measuring apparatus, comprising:

a measuring unit equipped with a transparent dielectric block and a thin film layer formed on one surface of the dielectric block;

first beam incidence means for making a first light beam enter the dielectric block at various angles of incidence so that a condition for total internal reflection is satisfied at an interface between the dielectric block and the thin film layer; and first photodetection means for receiving a predetermined polarized light component of the first light beam totally reflected at the interface;

wherein the measuring unit is measured a plurality of times and a change in the state of attenuated total reflection during the plurality of measurements is detected;

and wherein the measuring apparatus further comprises:

tilt measurement means for measuring a longitudinal tilt of the interface which changes the incidence angles during the plurality of measurements, and calculating means for obtaining a measured value in which errors due to the longitudinal tilt have been corrected according to the longitudinal tilt measured by the tilt measurement means.

The measuring apparatus described above may employ a metal film as the thin film layer, and be of a construction in which the aforementioned surface plasmon resonance effect is utilized to perform measurements.

Alternatively, the measuring apparatus described above may employ a cladding layer formed on a surface of the dielectric block and an optical waveguide layer formed atop the cladding layer as the thin film layer, and may be of a construction in which the excitation effect of a waveguide mode at the optical waveguide layer is utilized to perform measurements.

In accordance with the present invention, there is provided a second measuring apparatus, comprising:

a measuring unit equipped with a transparent dielectric block and a thin film layer formed on one surface of the dielectric block;

first beam incidence means for making a first light beam enter the dielectric block at an angle of incidence so that a condition for total internal reflection is satisfied at an interface between the dielectric block and the thin film layer; and first photodetection means for receiving a predetermined polarized light component of the first light beam totally reflected at the interface;

wherein the measuring unit is measured a plurality of times and a change in the state of attenuated total reflection during the plurality of measurements is detected;

and wherein the measuring apparatus further comprises:

tilt measurement means for measuring a longitudinal tilt of the interface which changes the incidence angles during the plurality of measurements, and adjustment means for making adjustments to the measuring unit, the first beam incidence means, and/or the first photodetection means so that errors due to the longitudinal tilt are corrected according to the longitudinal tilt measured by the tilt measurement means.

The measuring apparatus described above may employ a metal film as the thin film layer, and be of a construction in which the aforementioned surface plasmon resonance effect is utilized to perform measurements.

Alternatively, the measuring apparatus described above may employ a cladding layer formed on a surface of the dielectric block and an optical waveguide layer formed atop the cladding layer as the thin film layer, and may be of a construction in which the excitation effect of a waveguide mode at the optical waveguide layer is utilized to perform measurements.

Note that with regard to the second measuring apparatus described above, "a change in the state of attenuated total reflection during the plurality of measurements is detected" may refer to detecting a change in the state of ATR by detecting the light reflected at an interface, said light having been made incident to the interface with various angles of incidence, as in the first measuring apparatus. Alternatively, the measuring apparatus may be of the type that makes light beams of a plurality of wavelengths incident on an interface so that a condition for total internal reflection is met, and detect the degree of ATR for each wavelength by measuring the intensity of light of each wavelength totally internally reflected at the interface, as described by D. V. Noort, K. Johansen, and C. F. Mandenius in "Porous Gold in Surface Plasmon Resonance Measurement", *EUROSENSORS XIII*, 1999, pp. 585–588. Or, the measuring apparatus may be of the type that divides a portion of a light beam made incident on an interface so that a condition for total internal reflection is met before the light beam enters the interface, and makes the divided light beam interfere with the light beam reflected at the interface, and detects the intensity of the light beam after said interference, as described by P. I. Nikitin, A. N. Grigorenko, A. A. Beloglazov, M. V. Valeiko, A. I. Savchuk, and O. A. Savchuk in "Surface Plasmon Resonance Interferometry for Micro-Array Biosensing", *EUROSENSORS XIII*, 1999, pp. 235–238.

In the aforementioned measuring apparatuses, the expression "receiving a predetermined polarized light component of the first light beam totally reflected at the interface" means that if the light beam is a linearly polarized light capable of observing the state of totally internally reflected light, the light beam is received as it is. In the case where the light beam has a plurality of polarized light components, only a linearly polarized light capable of observing the state of totally internally reflected light is received by use of an optical component such as an analyzer, etc.

The expression "longitudinal tilt of the interface which changes the incidence angles" refers to a tilt from a reference interface position. It may be a tilt from the position of the interface obtained by an initial measurement, or a tilt from an average value of the interface positions obtained by a plurality of measurements.

The expression "making adjustments to the measuring unit, the first beam incidence means, and/or the first photodetection means" means that adjustments are performed on at least one of them to correct the tilt of the measuring unit.

With regard to the first or second measuring apparatus of the present invention, in the case that the beam incidence means as well as the photodetection means is constructed to make light beams incident on the interface at various angles of incidence, the state of ATR generated at the interface at a predetermined angle of incidence is measured, and the first light beam is a single light beam including components which strike the interface at various angles and having a predetermined light quantity distribution in a direction where an incidence angle to the interface changes, the tilt measurement means may measure the longitudinal tilt by utilizing at least a portion of the first light beam reflected at a portion of the measuring unit.

More specifically, the tilt measurement means may measure the longitudinal tilt by utilizing a component of the first light beam which is outside a measuring range of the attenuated total reflection. In this case, the tilt measurement means may measure the longitudinal tilt from a relationship between intensity of reflected light and a detected position, obtained for a portion of the first light beam, which is outside a measuring range of the attenuated total reflection, and in which a great change in a light quantity occurs due to the change in the incidence angle. In addition, the tilt measurement means may cause a portion of the first light beam, which is outside a measuring range of the attenuated total reflection, to strike the interface as a dark line, and may measure the longitudinal tilt, based on position of the dark line included in the first light beam reflected at the interface, detected by the first photodetection means.

The aforementioned tilt measurement means may comprise a converging lens for converging at least a portion of the first light beam reflected at a portion of the measuring unit, and second photodetection means for receiving the light beam converged by the converging lens and detecting position of the first light beam. That is, the longitudinal tilt of the interface may be detected by converging the reflected light with a converging lens and then detecting a change in the converged position.

Note that if the converging lens is movable along the optical path of the light beam and also in a direction perpendicular to the optical path, then the aforementioned first photodetection means can also be used as the second photodetection means. In this case, tilt measurements are made with the converging lens disposed in the optical path, while ATR measurements are made with the converging lens removed from the optical path.

In the case where the first light beam includes a plurality of polarized light components, the second photodetection means may receive a polarized light component, other than the predetermined polarized light component, of the first light beam, and may detect position of the first light beam.

In the measuring apparatus with the converging lens, the aforementioned tilt measurement means may further comprise a second lens between the converging lens and the second photodetection means. In this case, the converging lens, the second lens, and the second photodetection means are disposed with L, d0, d1, d2, f1, and f2 selected so that a relationship between a moved distance A of an angle of attenuated total reflection, expressed as $L \tan \theta + x$, and a spot movement quantity B of the first light beam on the second photodetection means, expressed as $\theta\{d1+d2-d1d2/f2-d0(d1/f1+d0/f1-d1d2/f1/f2-1+d2/f2)\}-x(d1/f1+d2/f1-d1d2/f1/f2-1+d2/f2)$, is $A = B$ or $A = -B$ , when f1 and f2 represent the focal lengths of the converging lens and the second lens, L represents the distance between the reflected position of the first light beam and the first photodetection means, d0 represents the distance between the reflected position and the converging lens, d1 represents the distance the converging lens and the second lens, d2 represents the distance between the second lens and the second photodetection means, x represents the shift quantity of the reflected position based on the shift quantity of the interface, and $\theta$ represents the longitudinal tilt of the interface.

Thus, if two lenses are disposed in the optical path between the interface and the second photodetection means at a predetermined interval, both the longitudinal tilt of the interface and the shift in a vertical direction of the interface can be detected.

For example, the converging lens, the second lens, and the second photodetection means can be disposed so that the relationship between the distances L, d0, d1, and d2 and the focal lengths f1 and f2 becomes d1=f1, d2=f2, and d0=f1+L.

In addition, with regard to the first or second measuring apparatuses of the present invention, the aforementioned tilt measurement means may comprise second beam incidence means for making a second light beam, which differs from the first light beam, enter a portion of the measuring unit, and second photodetection means for receiving the second light beam reflected at the portion of the measuring unit and detecting position of the second light beam.

In this case, the second light beam may have a wavelength differing from that of the first light beam. In the case where the first light beam is a linearly polarized light beam of the predetermined polarized light component, the second light beam may be a linearly polarized light beam of a polarized light component differing from the first light beam. In addition, a portion of the measuring unit may be the aforementioned interface or a predetermined surface of the measuring unit which tilts according to the longitudinal tilt of the interface. The predetermined surface may be the side or bottom surface of the dielectric body. In addition, it may be a reflecting surface provided near the one surface of the dielectric block on which the thin film layer is formed.

In accordance with the present invention, there is provided a third measuring apparatus, comprising:

a measuring unit equipped with a transparent dielectric block and a thin film layer formed on one surface of the dielectric block;

first beam incidence means for making a first light beam enter the dielectric block at various angles of incidence so that a condition for total internal reflection is satisfied at an interface between the dielectric block and the thin film layer; and first photodetection means for receiving a predetermined polarized light component of the first light beam totally reflected at the interface;

wherein the measuring unit is measured a plurality of times and a change in the state of attenuated total reflection during the plurality of measurements is detected;

and wherein the measuring apparatus further comprises
tilt measurement means for measuring a longitudinal tilt and a transverse tilt of the interface which change the incidence angles during the plurality of measurements, adjustment means for making adjustments to the measuring unit, the first beam incidence means, and/or the first photodetection means so that a shift of a received position of the first light beam on the first photodetection means resulting from the transverse tilt is corrected according to the transverse tilt measured by the tilt measurement means, and calculating means for obtaining a measured value in which errors due to the longitudinal tilt have been corrected according to the longitudinal tilt measured by the tilt measurement means.

The measuring apparatus described above may employ a metal film as the thin film layer, and be of a construction in which the aforementioned surface plasmon resonance effect is utilized to perform measurements.

Alternatively, the measuring apparatus described above may employ a cladding layer formed on a surface of the dielectric block and an optical waveguide layer formed atop the cladding layer as the thin film layer, and may be of a construction in which the excitation effect of a waveguide mode at the optical waveguide layer is utilized to perform measurements.

In accordance with the present invention, there is provided a fourth measuring apparatus, comprising:

a measuring unit equipped with a transparent dielectric block and a thin film layer formed on one surface of the dielectric block;

first beam incidence means for making a first light beam enter the dielectric block at an angle of incidence so that a condition for total internal reflection is satisfied at an interface between the dielectric block and the thin film layer; and first photodetection means for receiving a predetermined polarized light component of the first light beam totally reflected at the interface;

wherein the measuring unit is measured a plurality of times and a change in the state of attenuated total reflection during the plurality of measurements is detected;

and wherein the measuring apparatus further comprises
tilt measurement means for measuring a longitudinal tilt and a transverse tilt of the interface which change the incidence angles during the plurality of measurements, and adjustment means for making adjustments to the measuring unit, the first beam incidence means, and/or the first photodetection means so that a shift of a received position of the first light beam on the first photodetection means resulting from the transverse tilt, and errors due to the longitudinal tilt, are corrected according to the longitudinal and transverse tilts measured by the tilt measurement means.

The measuring apparatus described above may employ a metal film as the thin film layer, and be of a construction in which the aforementioned surface plasmon resonance effect is utilized to perform measurements.

Alternatively, the measuring apparatus described above may employ a cladding layer formed on a surface of the dielectric block and an optical waveguide layer formed atop the cladding layer as the thin film layer, and maybe of a construction in which the excitation effect of a waveguide mode at the optical waveguide layer is utilized to perform measurements.

Note that with regard to the fourth measuring apparatus described above, "a change in the state of attenuated total reflection during the plurality of measurements is detected" may refer to detecting a change in the state of ATR by detecting the light reflected at an interface, said light having been made incident to the interface with various angles of incidence, as in the third measuring apparatus. Alternatively, the measuring apparatus may be of the type that makes light beams of a plurality of wavelengths incident on an interface so that a condition for total internal reflection is met, and detect the degree of ATR for each wavelength by measuring the intensity of light of each wavelength totally internally reflected at the interface. Or, the measuring apparatus may be of the type that divides a portion of a light beam made incident on an interface so that a condition for total internal reflection is met before the light beam enters the interface, and makes the divided light beam interfere with the light beam reflected at the interface, and detects the intensity of the light beam after said interference.

In the third or fourth measuring apparatuses of the present invention, in the case that the beam incidence means as well as the photodetection means is constructed to make light beams incident on the interface at various angles of incidence, the state of ATR generated at the interface at a predetermined angle of incidence is measured, and the first light beam is a single light beam including components which strike the interface at various angles and having a predetermined light quantity distribution in a direction where an incidence angle to the interface changes, the aforementioned tilt measurement means may comprise a converging lens for converging at least a portion of the first light beam reflected at a portion of the measuring unit, and two-dimensional photodetection means for receiving the light beam converged by the converging lens and detecting position of the first light beam.

In addition, with regard to the third or fourth measuring apparatuses of the present invention, the tilt measurement means may comprise second beam incidence means for making a second light beam, which differs from the first light beam, enter a portion of the measuring unit, and two-dimensional photodetection means for receiving the second light beam reflected at the portion of the measuring unit and detecting position of the second light beam.

The aforementioned second light beam may have a wavelength differing from that of the first light beam. In the case where the first light beam is a linearly polarized light beam of the predetermined polarized light component, the second light beam may be a linearly polarized light beam of a polarized light component differing from the first light beam.

The aforementioned two-dimensional photodetection means may be constructed of a four-piece photodiode or resistance photodetector.

In addition, a portion of the measuring unit may be the aforementioned interface or a predetermined surface of the measuring unit which tilts according to the longitudinal tilt of the interface. The predetermined surface may be the side or bottom surface of the dielectric body. In addition, it may be a reflecting surface provided near the one surface of the dielectric block on which the thin film layer is formed.

In the aforementioned measuring apparatuses, the aforementioned dielectric block may be formed as a single block having a light entrance surface, a light exit surface, and the one surface on which the thin film layer is formed. In addition, the dielectric block may be constructed of a first portion having a light entrance surface and a light exit surface, and a second portion having the one surface on which the thin film layer is formed. In this case, the first portion and the second portion may be joined together through index-matching means.

In each of the aforementioned measuring apparatuses, the photodetection means can employ an area sensor, a line sensor, etc. More specifically, a two-piece photodiode and a photodiode array are preferred.

As described above, the first measuring apparatus of the present invention is equipped with tilt measurement means for measuring a longitudinal tilt of the interface which changes the incidence angles during the plurality of measurements, and calculating means for obtaining a measured value in which errors due to the longitudinal tilt are corrected according to the longitudinal tilt measured by the tilt measurement means. Therefore, when the same measuring unit is measured a plurality of times and a change in the state of ATR during the plurality of measurements is detected, a compensation for errors due to the longitudinal tilt of the interface is made and measurements can be performed more accurately.

The second measuring apparatus of the present invention is equipped with tilt measurement means for measuring a longitudinal tilt of the interface which changes the incidence angles during the plurality of measurements, and adjustment means for making adjustments to the measuring unit, the first beam incidence means, and/or the first photodetection means so that errors due to the longitudinal tilt have been corrected according to the longitudinal tilt measured by the tilt measurement means. Therefore, when the same measuring unit is measured a plurality of times and a change in the state of the totally internally reflected light during the plurality of measurements is detected, a compensation for errors due to the longitudinal tilt of the interface is made and measurements can be performed more accurately.

In the case that the apparatus makes light beams of various angles of incidence incident on the interface and measures the state of ATR, if the reflected-light intensity of a component, outside a measuring range of ATR, of the measuring light beam is utilized as the tilt measurement means, the longitudinal tilt of the interface can be detected without using a special device, and the size of the sensor and costs can be reduced.

In addition, as the tilt measurement means, a second light beam differing from a first measuring light beam can be utilized. Particularly, if a light beam with a polarization direction differing from that of the measuring light beam, or a light beam with a wavelength different from that of the measuring light beam, is utilized, totally internally reflected light and the longitudinal tilt of the interface can be simultaneously measured without having influence on the measuring light beam.

The third measuring apparatus of the present invention is equipped with adjustment means for making adjustments to the measuring unit, the first beam incidence means, and/or the first photodetection means so that a shift of a received position of the first light beam on the first photodetection means resulting from the transverse tilt is corrected according to the transverse tilt measured by the tilt measurement means, and calculating means for obtaining a measured value in which errors due to the longitudinal tilt have been corrected according to the longitudinal tilt measured by the tilt measurement means. Therefore, when the same measuring unit is measured a plurality of times and a change in the state of ATR during the plurality of measurements is detected, the shift of the received position of the measuring light beam due to the transverse tilt of the interface is corrected. In addition, the measuring light beam is prevented from not being received by the photodetection means, and a compensation for errors due to the longitudinal tilt of the interface is made. Thus, measurements can be performed more accurately.

The fourth measuring apparatus of the present invention is equipped with adjustment means for making adjustments to the measuring unit, the first beam incidence means, and/or the first photodetection means so that a shift of a received position of the first light beam on the first photodetection means resulting from the transverse tilt, and errors due to the longitudinal tilt, are corrected according to the longitudinal and transverse tilts measured by the tilt measurement means. Therefore, when the same measuring unit is measured a plurality of times and a change in the state of the totally internally reflected light during the plurality of measurements is detected, the shift of the received position of the measuring light beam due to the transverse tilt of the interface is corrected. In addition, the measuring light beam is prevented from not being received by the photodetection means, and a compensation for errors due to the longitudinal tilt of the interface is made. Thus, measurements can be performed more accurately.

BRIEF DESCRIPTION OF THE DRAWINGS

The present invention will be described in further detail with reference to the accompanying drawings wherein:

FIG. 2 is a block diagram showing the electrical construction of the surface plasmon resonance sensor shown in FIG. 1;

FIG. 3A is a graph showing the relationship between the incidence angle of a light beam and the intensity of the light beam, obtained according to the surface plasmon resonance sensor shown in FIG. 1;

FIG. 3B is a diagram showing a photodiode array employed in the surface plasmon resonance sensor shown in FIG. 1;

FIG. 3C is a graph showing the relationship between the incidence angle of the light beam and the differentiated value of the output of photodetection means;

FIG. 4 is a side view showing a surface plasmon resonance sensor constructed according to a second embodiment of the present invention;

FIG. 14 is a side view showing a surface plasmon resonance sensor constructed according to a tenth embodiment of the present invention;

FIG. 15 is a side view showing a surface plasmon resonance sensor constructed according to an eleventh embodiment of the present invention;

FIG. 17 is a side view showing a surface plasmon resonance sensor constructed according to a twelfth embodiment of the present invention;

DESCRIPTION OF THE PREFERRED EMBODIMENTS

Embodiments of the present invention will hereinafter be described in detail with reference to the drawings.

Figure 1:
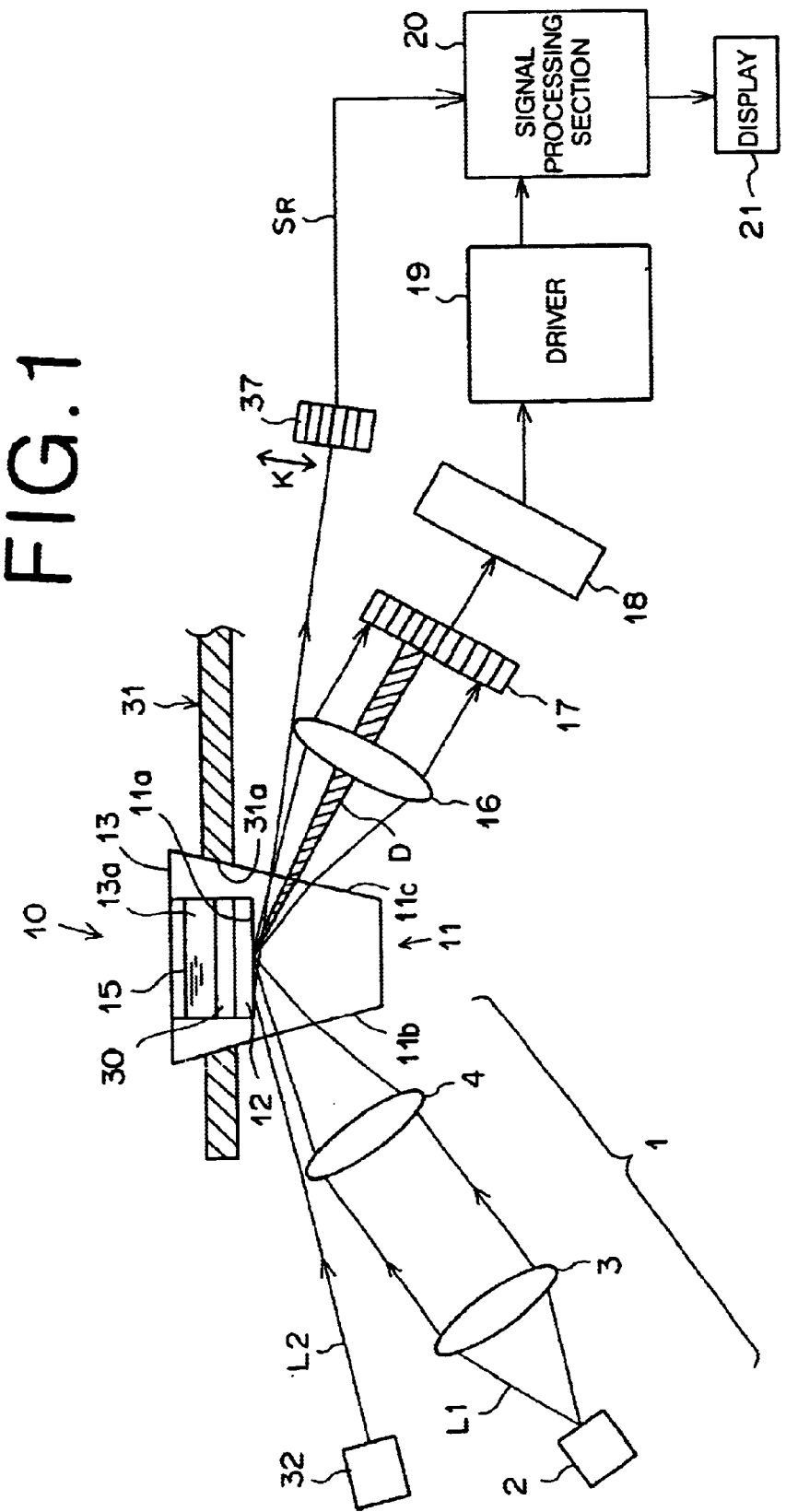
FIG. 1 is a side view showing a surface plasmon resonance sensor constructed according to a first embodiment of the present invention.

FIG. 1 schematically shows a side view of a measuring apparatus constructed according to a first embodiment of the present invention, which is a surface plasmon sensor that utilizes surface plasmon resonance.

A measuring chip 10 of the surface plasmon resonance sensor as a measuring unit has, for example, an inverted, truncated quadrangular pyramid shape formed from transparent resin, etc. The upper portion of the measuring chip 10 constitutes a target-substance holding portion 13, which has a target-substance holding hole 13a circular in cross section. The bottom surface of the target-substance holding hole 13a (a surface 11a of a dielectric block 11, to be described later) has a metal film 12 attached thereto, and the target-substance holding hole 13a holds, for example, a liquid sample 15 on the metal film 12. The lower portion of the measuring chip 10 constitutes the dielectric block 11. Two side surfaces of the four side surfaces of the dielectric block 11 are used as a light entrance surface 11b and a light exit surface 11c. That is, the dielectric block is formed as a single block having the entrance surface 11b, the exit surface 11c, and the surface on which a thin film layer (metal film) 12 is formed. In the first embodiment, a sensing medium 30 (which is to be described later) is placed on the metal film 12.

The measuring chip 10 is fitted in each of the chip holding apertures 31a formed in a turntable 31. With the measuring chips 10 thus fitted in the chip holding apertures 31a of the turntable 31, the turntable 31 is intermittently rotated a fixed angle at a time. If the measuring chip 10 is stopped at a predetermined position, the liquid sample 15 is dropped into the measuring chip 10 and held within the target-substance holding portion 13. If the turntable 31 is further rotated by the fixed angle, the measuring chip 10 is moved to the measuring position shown in FIG. 1 and is stopped there.

The surface plasmon resonance sensor of the first embodiment, in addition to the measuring chip 10 which is a measuring unit, is equipped with beam incidence means 1, a collimator lens 16, photodetection means 17, a differential amplifier array 18 connected to the photodetection means 17, a driver 19, a signal processing section 20 constructed of a computer system, etc., and display means 21 connected to the signal processing section 20. The beam incidence means 1 consists of an optical system for making a light beam L1 enter the dielectric block 11 so that various angles of incidence are obtained with respect to the interface 10a between the dielectric block 11 and the metal film 12. The collimator lens 16 is used for collimating the light beam L1 satisfying total internal reflection at the interface 11a. The photodetection means 17 is used for detecting the collimated light beam L1.

The beam incidence means 1 is constructed of a light source 2, which consists of a semiconductor laser, etc., for emitting the light beam L1; a collimator lens for 3 for collimating the light beam L1 emitted divergently from the light source 2; and a condenser lens 4 for collecting the collimated light beam L1 so that the beam L1 converges on the interface 11a.

As shown in FIG. 1, the light beam L1 emitted divergently from the light source 2 converges on the interface 10a between the dielectric block 11 and the metal film 12 by operation of the lenses 3, 4. Thus, the light beam L1 includes components incident at various incidence angles 0 with respect to the interface 11a. Note that the incidence angles 0 are greater than a critical incidence angle at which total internal reflection (TIR) takes place. Hence, the light beam L1 is totally reflected at the interface 11a, and the reflected light beam L1 includes components reflected at various angles. Note that the light beam L1 has to strike the interface 10a as a p-polarized light beam. For this reason, the light source 2 needs to be disposed so that the polarization direction thereof becomes a predetermined direction. Alternatively, the polarization direction of the light beam L1 may be controlled with a wavelength plate, a polarizing plate, etc. In addition, the beam incidence means 1 may be constructed so that the light beam 11 in a defocused state strikes the interface 11a. If done in this manner, errors in detecting the state of the surface plasmon resonance (e.g., errors in measuring the position of the aforementioned dark line) are averaged, whereby the accuracy of measurement is enhanced.

The light beam L1 satisfying total internal reflection at the interface 11a is collimated by the collimator lens 16 and is detected by the photodetection means 17. The photodetection means 17 in the first embodiment is constructed of a photodiode array in which a plurality of photodiodes 17a, 17b, 17c, . . . are juxtaposed in a row. As shown in FIG. 1, the direction in which the photodiodes are juxtaposed is approximately perpendicular to the traveling direction of the collimated light beam L1. Therefore, the components of the light beam L1 totally reflected at the interface 10a at various angles are received by the different photodiodes 17a, 17b, 17c, . . . , respectively.

FIG. 2 shows the electrical construction of the surface plasmon resonance sensor shown in FIG. 1. As shown in FIG. 2, the driver 19 is constructed of (1) sample holding circuits 22a, 22b, 22c, . . . for holding the outputs of the differential amplifiers 18a, 18b, 18c, . . . of the differential amplifier array 18; (2) a multiplexer 23 to which the outputs of the sample holding circuits 22a, 22b, 22c, . . . are input; and (3) an A/D converter 24 for digitizing the output of the multiplexer 23 and then inputting the digitized output to the signal processing section 20. The driver 19 is further constructed of (4) a drive circuit 25 for driving the multiplexer 23 and the sample holding circuits 22a, 22b, 22c, . . . , and (5) a controller 26 for controlling operation of the drive circuit 25 in response to a control signal from the signal processing section 20.

The outputs of the photodiodes 17a, 17b, 17c, . . . are input to the differential amplifiers 18a, 18b, 18c, . . . of the differential amplifier array 18. When it arises, the outputs of two adjacent photodiodes are input in common to a single differential amplifier. Therefore, the outputs of the differential amplifiers 18a, 18b, 18c, . . . are considered to be values obtained by differentiating photodetection signals, output from the photodiodes 17a, 17b, 17c . . . , in the direction where the photodiodes are juxtaposed.

The outputs of the differential amplifiers 18a, 18b, 18c, . . . are held at predetermined timing by the sample holding circuits 22a, 22b, 22c . . . , respectively, and are input to the multiplexer 23. The multiplexer 23 transmits the held outputs of the differential amplifiers 18a, 18b, 18c, . . . to the A/D converter 24 in a predetermined order. The A/D converter 24 digitizes these outputs and then inputs the digitized signals to the signal processing section 20.

FIG. 3A shows the relationship between the light intensity of the light beam L1 totally reflected at the interface 10a when it strikes the interface 10a at an incidence angle θ, and the output of the differential amplifier 18. Assume that the relationship between the incidence angle θ of the light beam L1 with respect to the interface 11a and the above-mentioned intensity I will become like that shown in FIG. 3A.

The light beam L1, incident on the interface 10a at a specific angle $\theta_{sp}$, excites surface plasmon at the interface 10a. Because of this, for the light beam L1 incident at the specific angle $\theta_{sp}$, the intensity I of the light beam L1 reflected at the interface 10a drops sharply. That is, the specific incidence angle $\theta_{sp}$ is an incidence angle at which ATR occurs. At the specific incidence angle $\theta_{sp}$, the intensity I of the reflected light beam L1 becomes the minimum value. The sharp drop in the intensity I of the reflected light beam L1 is observed as a dark line in the reflected light beam L, as shown at D in FIG. 1.

FIG. 3B shows the direction in which the photodiodes 17a, 17b, 17c . . . are juxtaposed. As described previously, the positions of the photodiodes 17a, 17b, 17c, . . . juxtaposed perpendicular to the reflected light beam correspond to the above-mentioned incidence angles θ, respectively.

The relationship between the juxtaposed positions of the photodiodes 17a, 17b, 17c, . . . (i.e., the incidence angles θ) and the outputs I' of the differential amplifiers 18a, 18b, 18c, . . . (i.e., the differentiated values of the intensities I) becomes like that shown in FIG. 3C.

Based on a differentiated value I' input from the A/D converter 24, the signal processing section 20 selects a differential amplifier of the differential amplifiers 18a, 18b, 18c, . . . which is outputting a value closest to the differentiated value I'=0 corresponding to the specific incidence angle $\theta_{sp}$ at which ATR occurs. In the example shown in FIG. 3, the differential amplifier 18d is selected. The differentiated value I' output from the selected differential amplifier is displayed on the display means 21. Note that when the output of one of the differential amplifiers is I'=0, that one differential amplifier is selected.

Thereafter, each time a predetermined time elapses, the output I' of the selected differential amplifier 18d is displayed on the display means 21. If the dielectric constant or refractive index of the substance in contact with the metal film 12 (see FIG. 1) changes and therefore the curve in FIG. 3A is shifted in the horizontal direction, then the differentiated value I' is increased or decreased according to the horizontal shift. Therefore, by continuously measuring the differentiated value I' with the lapse of time, a change in the refractive index of the substance in contact with the metal film 12, that is, a change in the property of the substance, can be detected.

Particularly, in the first embodiment, the sensing medium 30 that bonds with a specific substance in the liquid sample 15 is placed on the metal film 12, and according to the bonding state, the refractive index of the sensing medium 30 changes. Therefore, by continuously measuring the differentiated value I', how the bonding state changes can be detected. In this case, both the liquid sample 15 and the sensing medium 30 are samples that are analyzed. As a combination of the specific substance and the sensing medium 30, there is, for example, the combination of an antigen and an antibody.

Note that, in order to observe the manner in which the bonding state between the specific substance in the liquid sample 11 and the sensing medium 30 changes with the lapse of time, the differentiated value I' may be calculated and displayed, every time a predetermined time elapses. In addition, the difference ΔI' between the initial differentiated value I' (0) and the differentiated value I' (t) measured after the lapse of a predetermined time may be calculated and displayed.

In the case of measuring a difference between the differentiated values I', as described above, the same measuring chip is measured a plurality of times at predetermined time intervals. To measure a plurality of samples (measuring chips) efficiently, the measuring chip 10 is removed from the turntable 31, then the next measuring chip with another sample is measured, and the first measuring chip is again fitted in the turntable 31 after a predetermined time and is measured.

When resetting the measuring chip 10, there are cases in which the measuring chip is tilted from the previous state. Particularly, the longitudinal tilt of the interface 11a which changes the incidence angle of the light beam L1 relative to the interface 11a will have a great influence on a measured value.

Hence, the surface plasmon resonance sensor of the first embodiment is equipped with tilt measurement means, which is constructed of second beam incidence means 32 and second photodetection means 37. The second beam incidence means 32 is used for making a second light beam L2 enter the dielectric block 11 so that the second light beam L2 is totally reflected at the interface 11a. The second photodetection means 37 is used for detecting the second light beam L2, output from the second beam incidence means 32 and reflected at the interface 11a. More specifically, the second photodetection means 37 is a line photodetector, such as a photodiode array, etc., similar to the first photodetection means 17. More specifically, the second photodetection means 37 is constructed of photodiodes juxtaposed in the direction of arrow K so that a shift of the light beam 12 from the traveling direction thereof, caused by a change in the incidence angle (i.e., the reflection angle) of the light beam L2 due to the longitudinal tilt of the interface 11a, is detected. That is, the second photodetection means 37 is used for detecting the position of the light beam L2 shifted in the direction of arrow K. An output signal $S_R$ from the second photodetection means 37 is sent to the signal processing section 20. In the signal processing section 20, a correction signal for correcting the tilt of the interface 11a is added to a signal output from the photodetection means 17 that detects a surface plasmon resonance signal. In this manner, errors due to the tilt of the interface 11a are corrected and measured values are accurately obtained. More specifically, a correction is made by adding or subtracting the tilt of the interface 11a, found from a signal from the second photodetection means 37, to or from an angle (measured value) obtained for the plasmon resonance signal. That is, the signal processing means 20 constitutes calculating means. The second light beam L2 strikes the interface 11a as an s-polarized light beam so that the polarization direction thereof differs from that of the light beam L1.

When a first measurement of the sample 15 is made, the second light beam L2 emitted from the second beam incidence means 32 is reflected at the interface 11a, and the reflected light beam is detected by the second photodetection means 37. When a second measurement is made, the second light beam L2 is similarly reflected and detected, and a shift in the direction of arrow K from the position obtained in the first measurement is calculated. This positional shift corresponds to the longitudinal tilt of the interface 11a. Thus, the longitudinal tilt of the interface 11a is measured by measuring the detected position of the reflected light beam that changes due to the longitudinal tilt of the interface 11a which changes the incidence angle of the light beam L1 with respect to the interface 11a. Based on the longitudinal tilt of the interface 11a obtained by a change in the detected position of the light beam L2, the signal processing section 20 obtains a measured value in which errors due to the longitudinal tilt have been corrected. In a third measurement and measurements thereafter, measured values in which errors due to the longitudinal tilt of the interface from the first measurement have been corrected are likewise obtained. This makes it possible to obtain a measured value in which a compensation for the longitudinal tilt of the interface 11a has been made. In this manner, measurements can be performed more accurately.

Note that the tilt of the interface 11a during a plurality of measurements occurs when a table for supporting the measuring chip is rotated, or when the supporting table, the light source, and the photodetectors are moved, as well as when the measuring chip is reset. As with the aforementioned embodiments, the longitudinal tilt of the interface 11a that occurs in these cases is measured, and based on the measured tilt, a measured value in which corrections have been made according to the longitudinal tilt can be obtained. In this manner, measurements can be performed with higher reliability.

In addition, in the case where a change in the aforementioned specific incidence angle (at which ATR occurs) due to only the liquid sample 15 is detected by measuring the state of ATR before the pouring of the liquid sample 15 into the measuring chip 10 and then subtracting the bulk effect of the measuring chip 10 from a value measured after the pouring of the liquid sample into the measuring chip 10, the reliability of measured values will be reduced, if the tilt of the interface 11a occurs before and after the pouring of the liquid sample 15 into the measuring chip 10. In such a case, if the longitudinal tilt of the interface 11a is measured, and measured values are corrected based on the tilt, measurements can be performed with high reliability.

FIG. 4 shows measuring apparatus constructed according to a second embodiment of the present invention. Note that in FIG. 4 and figures thereafter that the same reference numerals are applied to the same parts as those in FIG. 1, and that a description of the same parts is omitted unless particularly necessary.

The surface plasmon resonance sensor of the second embodiment is nearly the same in construction as the first embodiment, but means for tilt compensation after the tilt measurement of an interface 11a differs from that of the first embodiment. The measuring apparatus of the second embodiment is equipped with position adjustment means for moving first photodetection means 17, which detects a specific incidence angle at which ATR occurs, in the direction of arrow x in order to compensate for the longitudinal tilt of the interface 11a obtained from a value measured by second photodetection means 37. That is, the position adjustment means, which is a vertical adjustment means, consists of first photodetection means 17 movable in the direction of arrow x and drive means 35 for moving the first photodetection means 17. The drive means 35 moves the first photodetection means 17 in response to a signal from a signal processing section 20. That is, in the second embodiment, errors due to the longitudinal tilt of the interface 11a are corrected not by correcting a measured value by calculation, but by moving the first photodetection means 17.

Thus, the surface plasmon resonance sensor of the second embodiment is equipped with vertical adjustment means for moving the photodetection means 17 according to a longitudinal tilt detected by tilt measurement means, and is capable of obtaining results of measurement in which a compensation for the longitudinal tilt of the interface 11a has been made by a physical positional adjustment.

Figure 5:
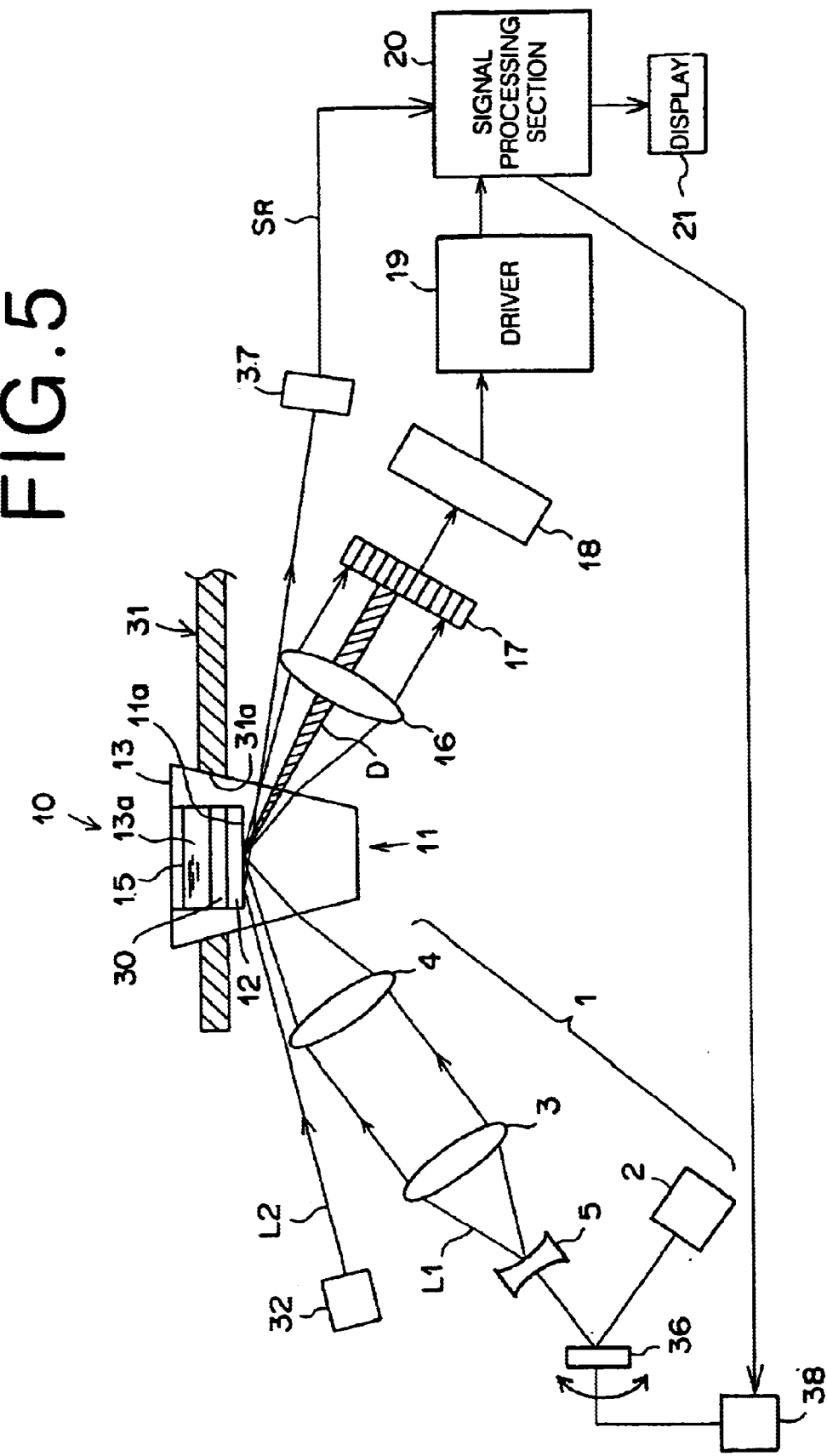
FIG. 5 is a side view showing a surface plasmon resonance sensor constructed according to a third embodiment of the present invention.

FIG. 5 shows a measuring apparatus constructed according to a third embodiment of the present invention. In the measuring apparatus, of the third embodiment, which is a plasmon sensor, incidence-angle adjustment means for adjusting an incidence angle by beam incidence means 1 is provided as the longitudinal adjustment means instead of positional adjustment of the photodetection means 17. The incidence-angle adjustment means is constructed of a mirror 36 and drive means 38 for rotating the mirror 36. The mirror 36 has a surface for reflecting a light beam L1 emitted from a light source 2, and is rotatable in the direction where the reflecting surface changes the incidence angle of the light beam L1. The drive means 38 rotates the mirror 36 in response to a signal from a signal processing section 20 to adjust an angle of reflection. That is, by adjusting the incidence angle of the light beam L1 with respect to an interface 11a when each measurement is made, adjustments are made so that the light beam L1 is always reflected at the interface 11a in approximately the same direction. Note that the beam incidence means 1 of the third embodiment is constructed so that the small-diameter light beam emitted from the light source 2 is diffused by a concave lens 5.

Thus, the light beam L1 is inclined according to the longitudinal tilt of the interface 11a obtained by the tilt measurement means, whereby the incidence angle of the light beam L1 with respect to the interface 11a can be made constant. Therefore, the measuring apparatus of the third embodiment is capable of obtaining results of measurement in which a compensation for the longitudinal tilt of the interface 11a has been made.

As described above, in addition to making adjustments to the photodetection means 17 or beam incidence means 1, adjustments may be made so that the longitudinal tilt of the interface 11a is corrected by tilting the measuring chip 10 itself. In addition, by adjusting all or two of the photodetection means 17, beam incidence means 1, and measuring chip 10, measured values may be obtained in which a compensation for the longitudinal tilt of the interface 11a has been made as a whole.

Figure 6:
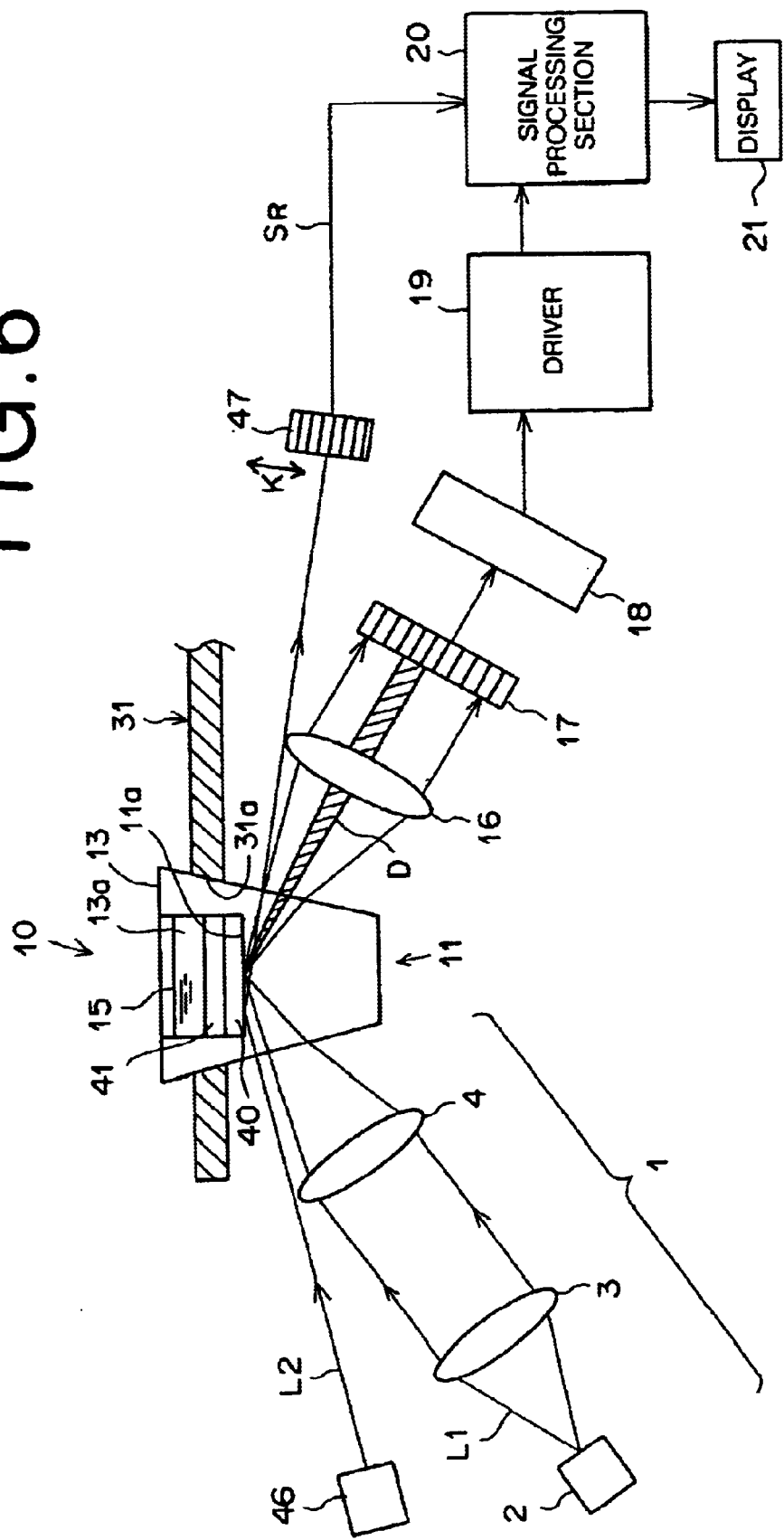
FIG. 6 is a side view showing a leaky mode sensor constructed according to a fourth embodiment of the present invention.

FIG. 6 shows a measuring apparatus constructed according to a fourth embodiment of the present invention, which is a leaky mode sensor described above. The fourth embodiment is similarly constructed so that a measuring chip 10 is employed as a measuring unit. However, the bottom surface of the target-substance hole 13a of the measuring chip 10 is provided with a cladding layer 40 on which an optical waveguide layer 41 is formed.

The cladding layer 40 is formed into the shape of a thin film by employing a dielectric lower in refractive index than a dielectric block 11, or metal such as gold, etc. The optical waveguide layer 41 is also formed into the shape of a thin film by employing a dielectric, such as polymethylmethacrylate (PMMA), which is higher in refractive index than the cladding layer 40. The cladding layer 40 is 36.5 nm in thickness when it is formed from a thin gold film. The optical waveguide layer 41 is about 700 nm in thickness when it is formed from PMMA.

In the leaky mode sensor of the fourth embodiment, if a light beam L1 emitted from a light source 2 strikes the cladding layer 40 through the dielectric block 11 at angles of incidence greater than an angle of incidence at which total internal reflection takes place, the light beam L1 is totally reflected at an interface 11a between the dielectric block 11 and the cladding layer 40. However, the light beam with a specific wave number, incident on the optical waveguide layer 41 through the cladding layer 40 at a specific angle of incidence, propagates through the optical waveguide layer 41 in a waveguide mode. If the waveguide mode is thus excited, the greater part of the incident light is confined within the optical waveguide layer 41, and consequently, ATR occurs in which the intensity of the light totally reflected at the interface 10a drops sharply.

Since the wave number of the light propagating through the optical waveguide layer 41 depends on the refractive index of a sample 15 on the optical waveguide layer 41, both the refractive index of the sample 15 and the properties of the sample 15 related to the refractive index thereof can be analyzed by finding the above-mentioned specific incidence angle $\theta_{sp}$ at which ATR takes place. The properties of the sample 15 can also be analyzed based on the intensity I of the reflected light near the specific incidence angle $\theta_{sp}$, or the differentiated value I' output from each differential amplifier of the differential amplifier array 18.

The leaky mode sensor of the fourth embodiment is equipped with second beam incidence means 46 and photodetection means 47. The second beam incidence means 46 is used for making a second light beam L2 enter the dielectric block 11 so that the second light beam L2 is totally reflected at the interface 11a. The photodetection means 47 is used for detecting the second light beam L2, output from the second beam incidence means 46 and reflected at the interface 11a. An output signal $S_R$ from the photodetection means 47 is sent to a signal processing section 20. In the signal processing section 20, a correction signal for correcting the tilt of the interface 11a is added to a signal output from the photodetection means 17 that detects a surface plasmon resonance signal. In this manner, measured values can be accurately obtained. That is, the signal processing means 20 constitutes calculating means. Note that the second light beam L2 has a wavelength different from that of the first light beam L1.

When a first measurement of the sample 15 is made, the second light beam L2 emitted from the second beam incidence means 46 is reflected at the interface 11a, and the reflected light beam is detected by the photodetection means 47. When a second measurement is made, the second light beam L2 is similarly reflected and detected, and a shift in the direction of arrow K from the position obtained in the first measurement is calculated. This positional shift corresponds to the longitudinal tilt of the interface 11a. Based on the obtained tilt, the signal processing section 20 obtains a measured value in which errors due to the tilt has been corrected. This makes it possible to obtain a measured value in which a compensation for the longitudinal tilt of the interface 11a has been made. In this manner, measurements can be performed more accurately.

Figure 7:
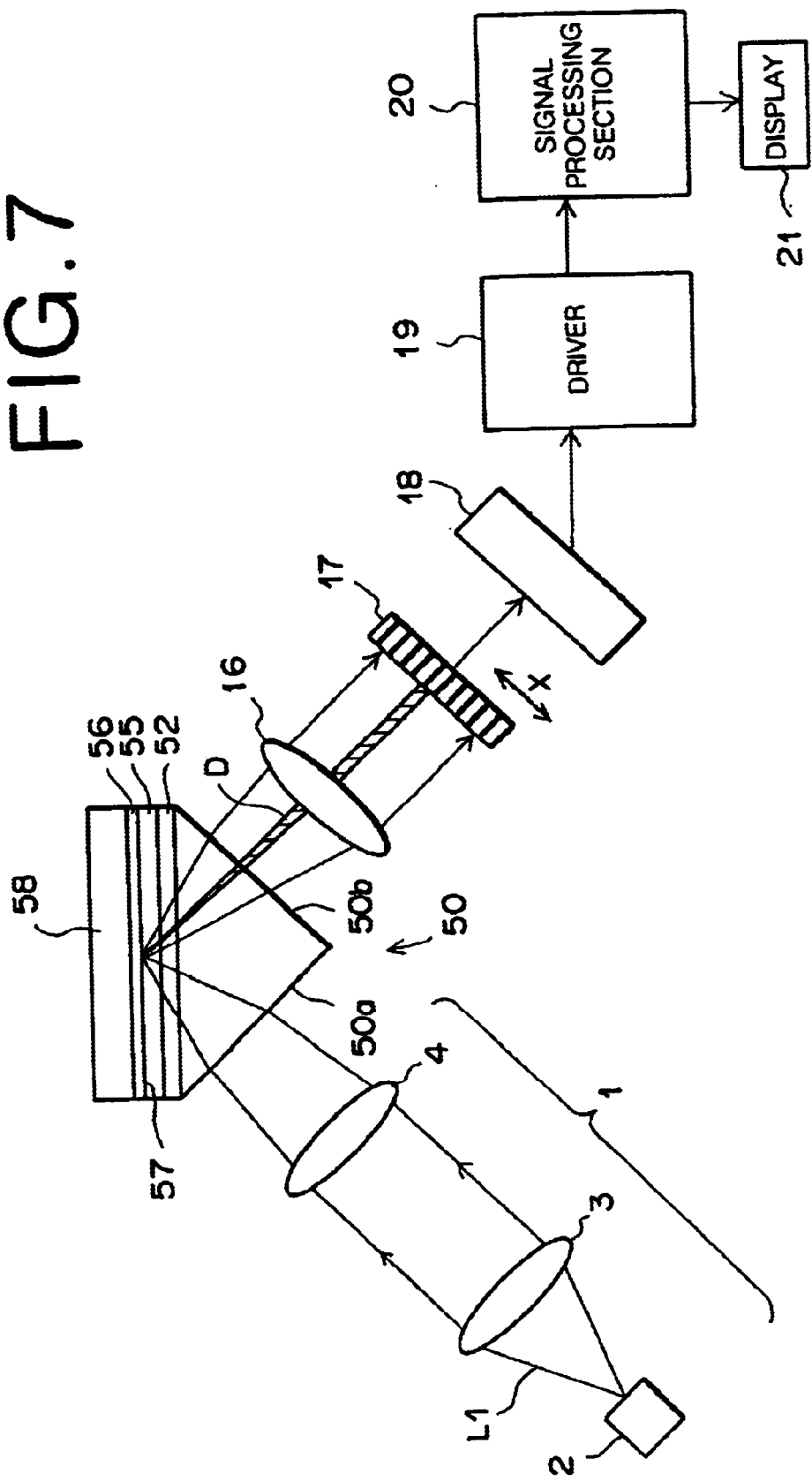
FIG. 7 is a side view showing a surface plasmon resonance sensor constructed according to a fifth embodiment of the present invention.

FIG. 7 shows a measuring apparatus constructed according to a fifth embodiment of the present invention, which is a surface plasmon sensor that utilizes surface plasmon resonance, similar to the measuring apparatus of the first embodiment.

The fifth embodiment employs a measuring unit differing in construction from that shown in FIG. 1. That is, the fifth embodiment employs a trigonal prism 50 and a dielectric plate instead of the measuring chip 10 employed in the first embodiment of FIG. 1. The trigonal prism 50 is formed from a dielectric such as glass and extends in a direction perpendicular to the surface of the drawing sheet of FIG. 7. The dielectric plate 55 is mounted on the top surface of the trigonal prism 50 through index-matching oil 52. The prism 50 has a light entrance surface 50a and a light exit surface 50b. On the other hand, the dielectric plate 55 has a metal film 56 formed thereon, and a light beam L1 is totally reflected at the interface 57 between the dielectric plate 55 and the metal film 56. A sample 58 is placed on the dielectric plate 55 having the metal film 56 formed thereon, and the dielectric plate 55 with the sample 58 is removable. That is, in the measuring unit of the fifth embodiment, the portion 50 with the entrance surface 50a and the exit surface 50b is joined with the portion 55 with a surface having the thin film layer 56 formed thereon, by the index-matching means (index-matching oil) 52.

The surface plasmon resonance sensor of the fifth embodiment is equipped with tilt measurement means differing from the tilt measurement means of surface plasmon resonance sensor of the first embodiment. A description will hereinafter be described of the tilt measurement means of the fifth embodiment.

Figure 8:
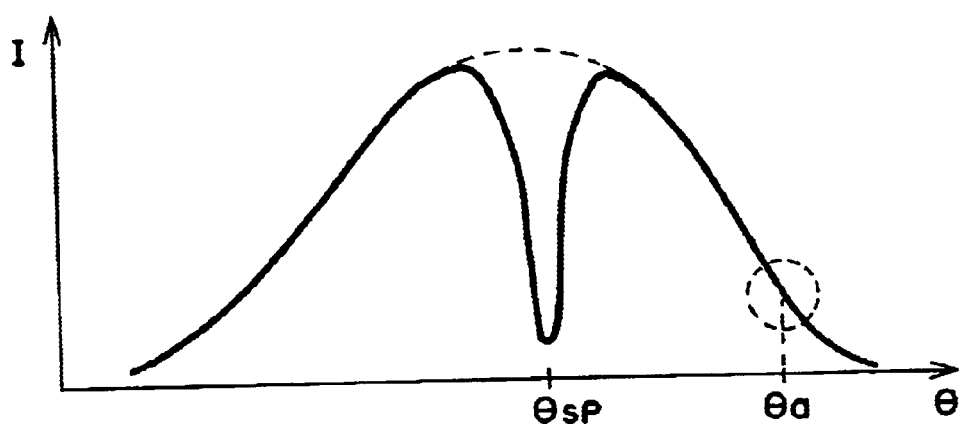
FIG. 8 is a diagram showing the reflected light intensity distribution employed in the surface plasmon resonance sensor of the fifth embodiment.

Generally, surface plasmon resonance sensors employ a light beam whose light-quantity distribution becomes like a Gaussian distribution shown in FIG. 8. The aforementioned specific incidence angle $\theta_{sp}$ at which ATR takes place is set near the peak intensity, and as described above, a change in the specific incidence angle $\theta_{sp}$ is observed. Therefore, both end portions of the Gaussian distribution hardly contribute to measurements. Hence, in the surface plasmon resonance sensor of the fifth embodiment, the longitudinal tilt of the interface 57 is calculated by utilizing the portions of the Gaussian distribution that are outside a measuring range. In the region of the Gaussian distribution outside the measuring range, the relationship between the intensity and incidence angle of a light beam does not change, and a change in the relationship will occur only by the tilt of the interface. Therefore, in the fifth embodiment, a light quantity is observed at a place where the light-quantity distribution changes sharply, like a place enclosed within a circle indicated by a broken line in FIG. 8. Based on a change in the light quantity, the longitudinal tilt of the interface is calculated. More specifically, the light intensity at an incidence angle $\theta_a$ is detected by photodetection means 17. That is, the longitudinal tilt of the interface 57 is detected by detecting a change in the output of a predetermined photodiode of the photodetection means 17. Based on the tilt thus detected, as with the aforementioned embodiments, a signal processing section 20 obtains a measured value in which errors due to the longitudinal tilt have been corrected.

Figure 9:
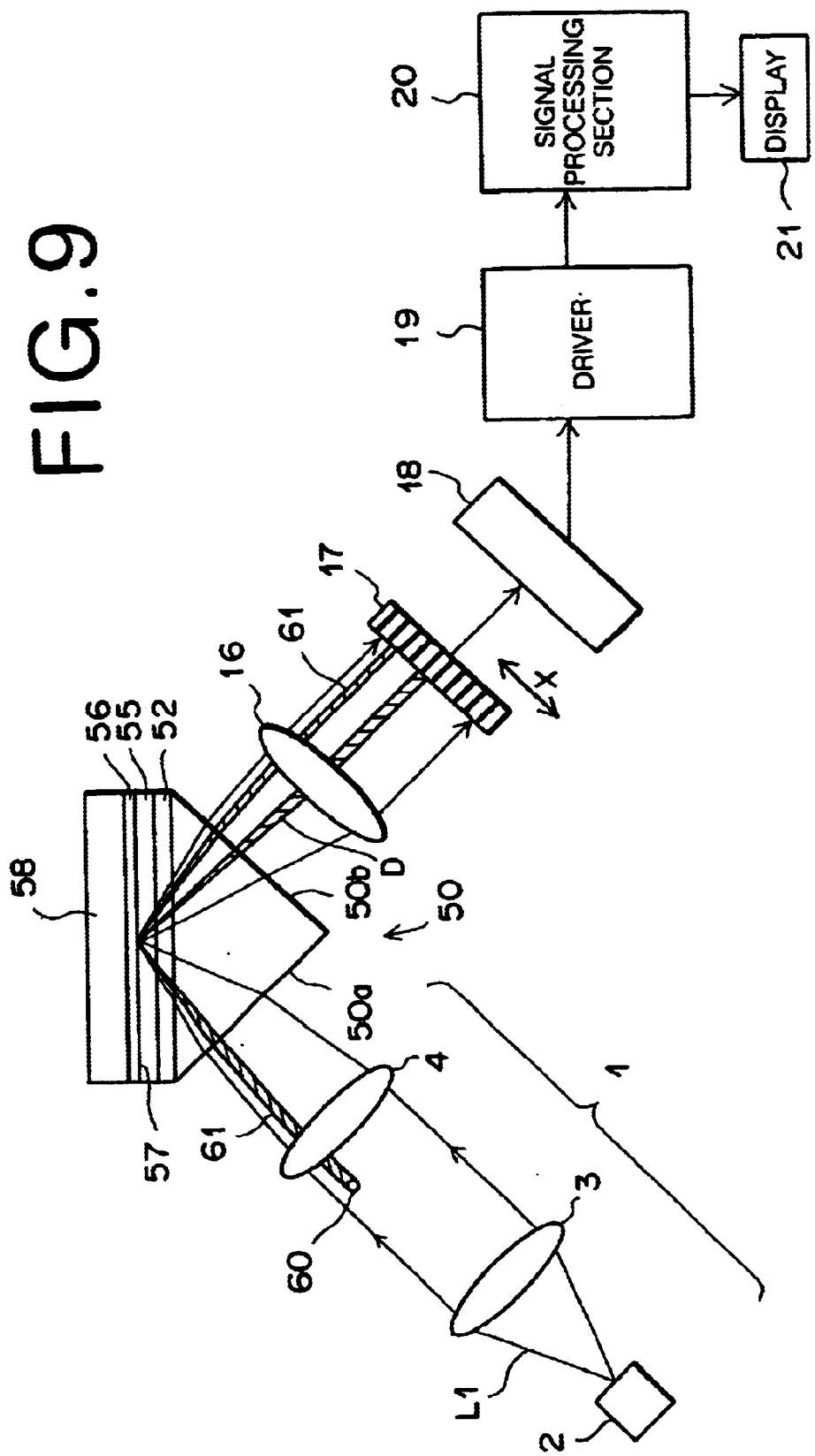
FIG. 9 is a side view showing a surface plasmon resonance sensor constructed according to a sixth embodiment of the present invention.

FIG. 9 shows a measuring apparatus constructed according to a sixth embodiment of the present invention, which is a surface plasmon sensor that utilizes surface plasmon resonance, similar to the fifth embodiment. The sixth embodiment is nearly the same in construction as the fifth embodiment, but differs in that (1) a shielding object 60 is disposed in an optical path on the side of an optical incidence system for a light beam L1, (2) part of the light beam L1 is caused to strike an interface 57 as a dark line 61, and (3) the longitudinal tilt of the interface 57 is detected by detecting the dark line 61 included in the light beam L1 reflected at the interface 57.

Figure 10:
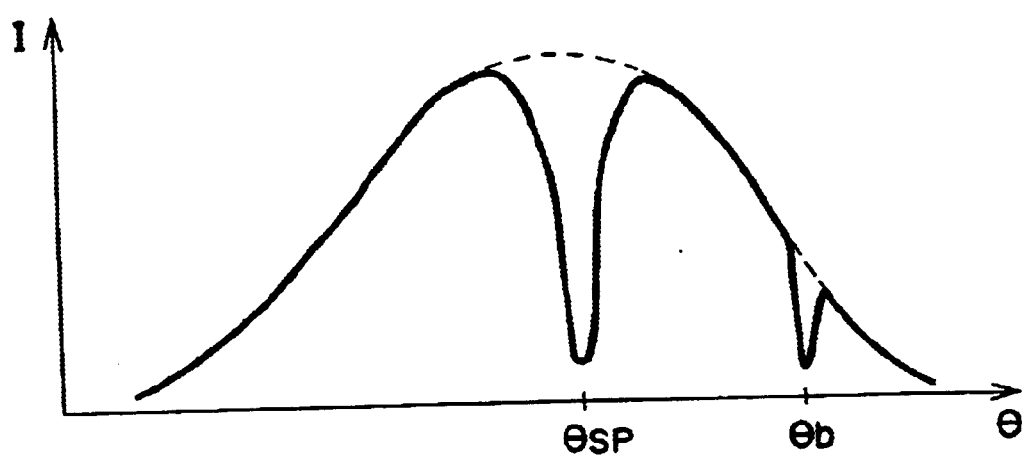
FIG. 10 is a diagram showing the light intensity distribution employed in the surface plasmon resonance sensor of the sixth embodiment.

As with the fifth embodiment, the light beam L1 employs a light beam whose light-quantity distribution becomes like the Gaussian distribution shown in FIG. 10, and the longitudinal tilt of an interface 57 is detecting by utilizing the end portions of the Gaussian distribution which hardly contribute to measurements of ATR. As described above, part of the light beam L1 is caused to strike the interface 57 as a dark line 61, and the dark line 61 is detected by photodetection means 17. Unless the longitudinal tilt of the interface 57 changes, the position of the dark line 61 which is detected on the photodetection means 17 remains the same. Therefore, a shift from the initial position corresponds to the vertical shift of the interface 57. For example, the dark line 61 is detected by the photodiode corresponding to the angle $\theta_a$ at a first measurement. Thereafter, if the angle of the interface 57 changes, the dark line 61 will be detected by a different photodiode at a second measurement. Therefore, the longitudinal tilt of the interface 57 is detected by the position of a photodiode detecting the dark line 61. Based on the tilt thus obtained, a signal processing section 20 obtains a measured value in which errors due to the tilt have been corrected.

Other embodiments of measuring apparatuses will hereinafter be described with reference to FIGS. 11 to 23. However, the method of measuring ATR is nearly the same as those in the aforementioned embodiments, and the tilt measurement means differs in construction. Therefore, a description will be given of the tilt measurement means, and for the parts associated with measurements of ATR, only the changed parts will be described.

Figure 11:
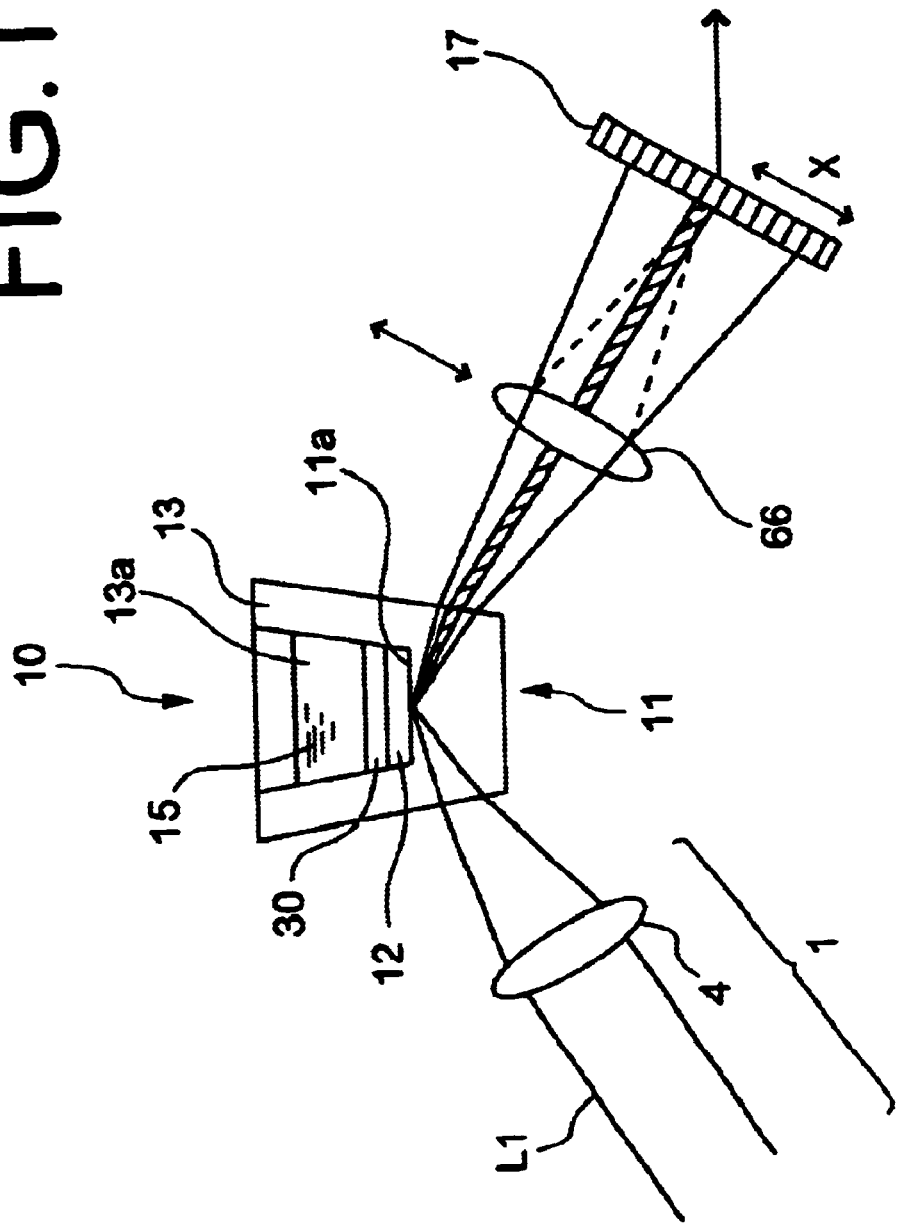
FIG. 11 is a side view showing a surface plasmon resonance sensor constructed according to a seventh embodiment of the present invention.
Figure 12:
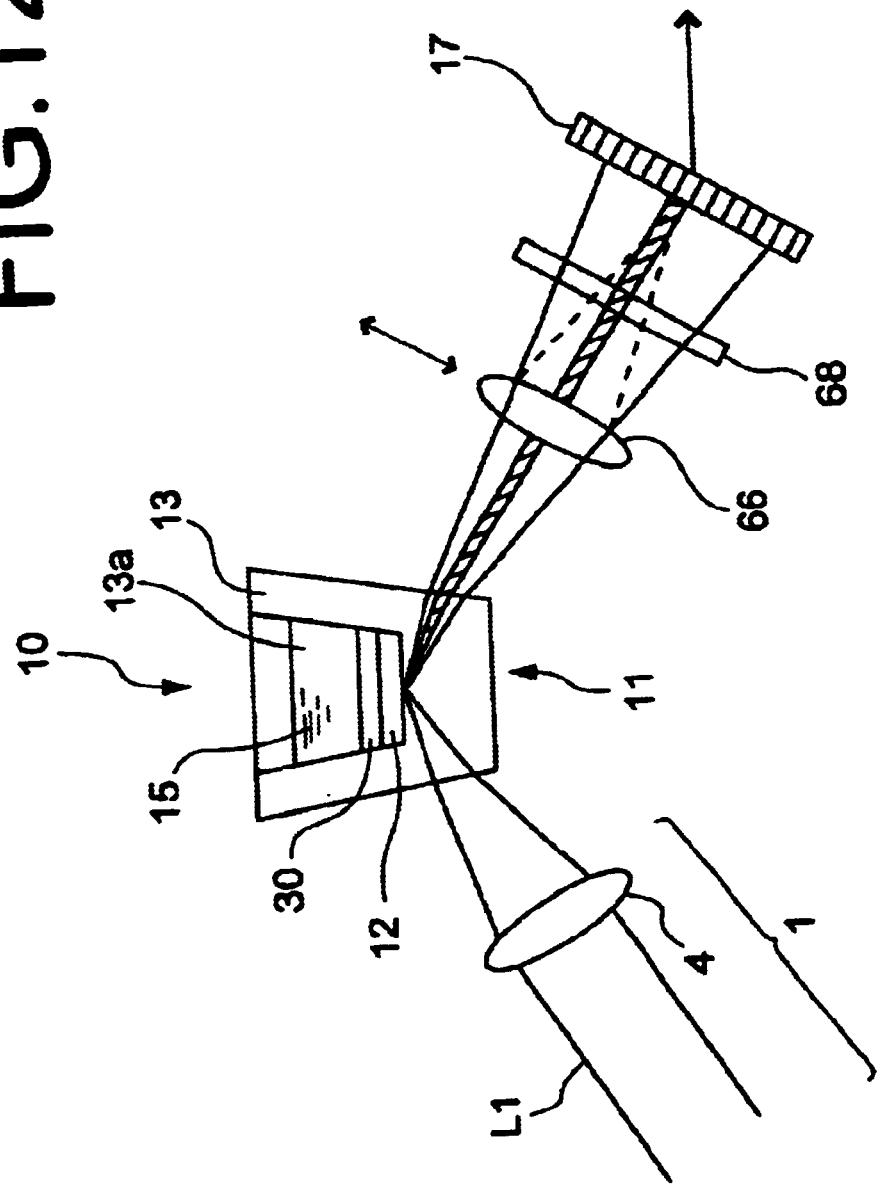
FIG. 12 is a side view showing a surface plasmon resonance sensor constructed according to an eighth embodiment of the present invention.

FIG. 11 shows a measuring apparatus constructed according to a seventh embodiment of the present invention.

The tilt measurement means of the measuring apparatus of the seventh embodiment is constructed of a converging lens 66 and photodetection means 17. The converging lens 66 is movable along the optical path between an interface 11a and the photodetection means 17 and also in a direction perpendicular to the optical path. In the measuring apparatus of the seventh embodiment, the longitudinal tilt of the interface 11a is measured with the converging lens 66 disposed between the interface 11a and the photodetection means 17, and is also measured without it the converting lens 66. That is, in the sensor of the seventh embodiment, the light beam L1 reflected at the interface 11a is caused to converge on the photodetection means 17 by the converging lens 66, and by detecting a change in the position, detected in the direction of arrow x, of the light beam converging on the photodetection means 17, the longitudinal tilt of the interface 11a is measured.

In the seventh embodiment, the light beam L1 strikes the interface 11a as p-polarized light, and the state of a dark line generated by surface plasmon resonance is detected. However, in the case where light including a plurality of polarized light components is utilized as the light beam L1, it is necessary to detect only a p-polarized light component at the photodetection means 17 to detect the surface plasmon resonance. In the case where the light beam L1 includes polarized light components other than the p-polarized light component, an analyzer 68 can be disposed between the converging lens 66 and the photodetection means 17, as in a sensor of an eighth embodiment shown in FIG. 12. In this case, only the p-polarized light component is transmitted through the analyzer 68. Note that the analyzer 68 may be rotated during measurement so that the position, on the photodetection means 17, of the s-polarized light component perpendicular to the p-polarized light component can be detected.

Figure 13:
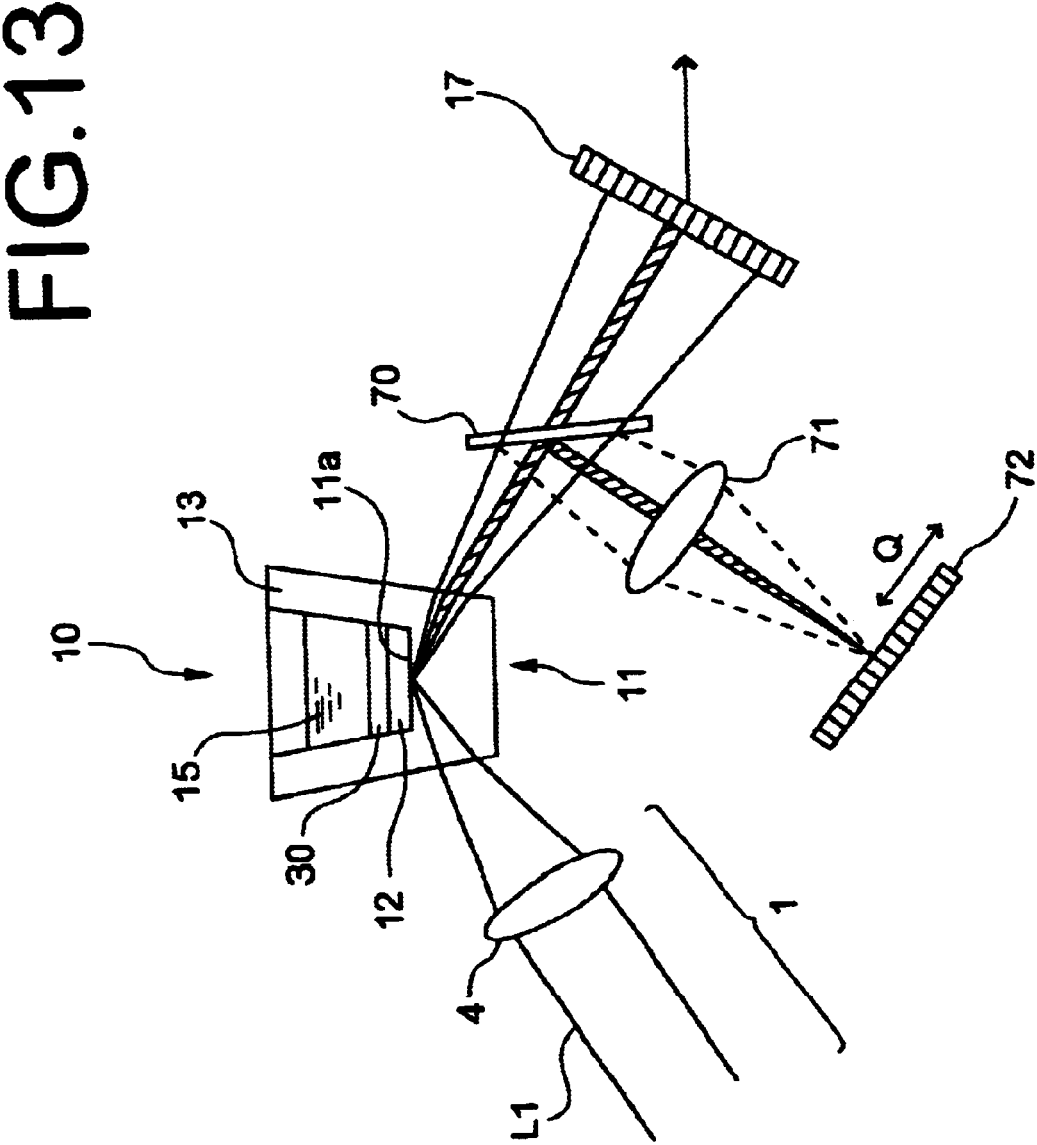
FIG. 13 is a side view showing a surface plasmon resonance sensor constructed according to a ninth embodiment of the present invention.

FIG. 13 shows a measuring apparatus constructed according to a ninth embodiment of the present invention.

The tilt measurement means of the measuring apparatus of the ninth embodiment is constructed of a half mirror 70, a converging lens 71, and second photodetection means 72. The half mirror 70 is disposed in the optical path between an interface 11a and photodetection means 17. The converging lens 71 is used for converging part of a light beam separated by the half mirror 70, and the second photodetection means 72 is used for detecting the light beam converged by the converging lens 71. The light beam L1 reflected at an interface 11a is split into two light beams by the half mirror 70. One of the two light beams is used for measuring ATR, while the other is used for measuring a tilt. The light beam L1 reflected by the half mirror 70 is converged on the second photodetection means 72 by the converging lens 71. Based on a change in the position, detected in the direction of arrow Q, of the light beam on the photodetection means 72, the longitudinal tilt of the interface 11 is detected. Note that the ninth embodiment may be equipped with a mirror movable along the optical path and also in a direction perpendicular to the optical path, instead of the half mirror 70. In this case, the longitudinal tilt of the interface 11a is detected with the movable mirror disposed between the interface 11a and the photodetection means 72, and ATR is measured with the movable mirror removed from the optical path between the interface 11a and the photodetection means 17.

In the ninth embodiment, the light beam L1 strikes the interface 11a as p-polarized light, and the state of a dark line generated by surface plasmon resonance is detected. However, in the case where light including a plurality of polarized light components is utilized as the light beam L1, an analyzer 68 can be disposed between the converging lens 66 and the photodetection means 17, as in a sensor of a tenth embodiment shown in FIG. 14. In this case, only the p-polarized light component is transmitted through the analyzer 68.

FIG. 15 shows a measuring apparatus constructed according to an eleventh embodiment of the present invention.

The tilt measurement means of the measuring apparatus of the eleventh embodiment is constructed so that in the ninth embodiment shown in FIG. 13, a second lens 75 is further disposed in the optical path between a converging lens 71 and second photodetection means 72. The use of the two lenses 71 and 75 makes it possible to obtain both the vertical tile of an interface 11a and a characteristic value corresponding to the quantity of the interface 11a shifted in the vertical direction. In this manner, the state of ATR can be measured with a high degree of accuracy.

Figure 16A:
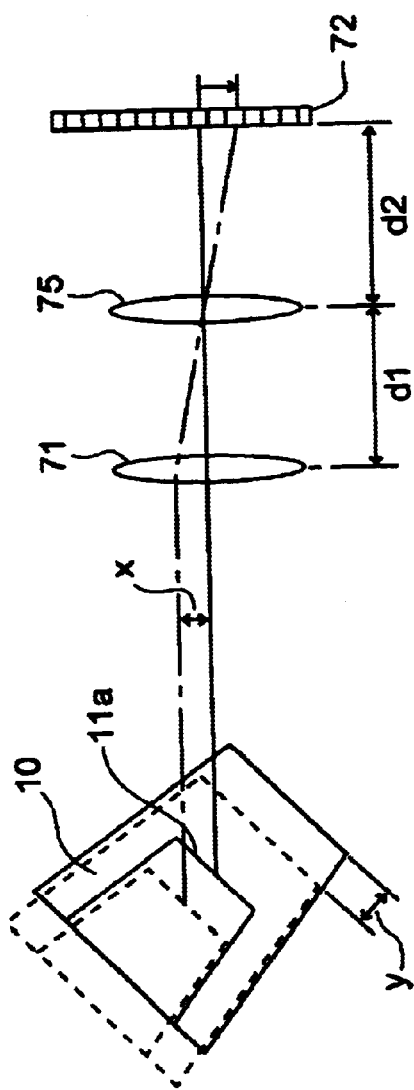
FIG. 16A is a schematic diagram used to explain how the vertical shift quantity of an interface is detected.

The manner in which the longitudinal tilt and vertical shift quantity of the interface are detected will be briefly described with reference to FIG. 16. FIG. 16A shows the manner in which the vertical shift quantity is detected. FIG. 15B shows the manner in which the longitudinal tilt is detected.

Figure 16B:
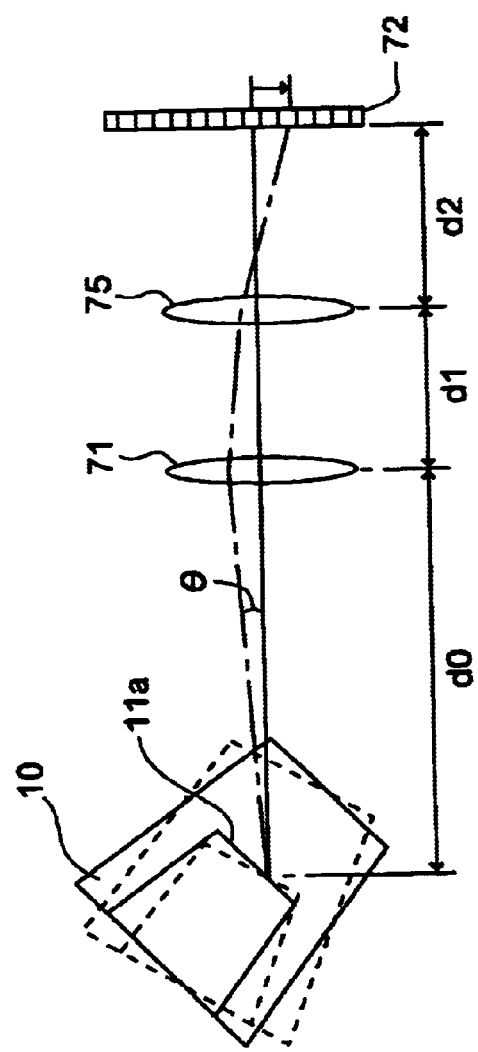
FIG. 16B is a schematic diagram used to explain how the longitudinal tilt of the interface is detected.

The focal lengths of the converging lens 71 and second lens 75 are represented by f1 and f2, respectively. The distance between the reflected position of the light beam L1 and the photodetection means is represented by L (see FIG. 15). As shown in FIGS. 16A and 16B, the distance between the reflected position of the light beam and the converging lens 71 is represented by d0, the distance between the converging lens 71 and the second lens 75 by d1, and the distance between the second lens 75 and the second photodetection means 72 by d2. Furthermore, the shift quantity of the reflected position based on the vertical shift quantity y of the interface 11a is represented by x, and the tilt of the interface 11a is represented by θ. In FIG. 15, while the optical path is changed in direction by the half mirror 70, in FIG. 16 the optical path is expressed as a straight line for the purpose of explanation.

When the longitudinal tilt and vertical shift quantity of the interface 11a are θ and x, the moved distance A of the specific incidence angle (at which ATR occurs) due to the longitudinal tilt and vertical shift of the interface 11a is expressed as $L \tan \theta + x$.

On the other hand, when the measuring chip 10 is shifted for a distance y from the position indicated by a solid line to the position indicated by a broken line, as shown in FIG. 16A, the shift quantity x of the incidence position of the light beam develops as a predetermined shift quantity at the beam-detected position on the second photodetection means 72. When the measuring chip 10 is tilted from the position indicated by a solid line to the position indicated by a broken line, as shown in FIG. 16B, the beam-detected position on the photodetection means 72 changes by a predetermined shift quantity.

The spot movement quantity B of the light beam on the second photodetection means 72 due to the tilt and vertical shift of the interface 11a is expressed as $\theta\{d1+d2-d1d2/f2-d0(d1/f1+d0/f1-d1d2/f1/f2-1+d2/f2)\}-x(d1/f1+d2/f1-d1d2/f1/f2-1+d2/f2)$.

Therefore, if L, d0, d1, d2, f1, and f2 are selected so that the relationship between the moved distance A of the aforementioned specific incidence angle on the photodetection means 17 and the spot movement quantity B of the light beam on the second photodetection means 72 is A=B or A=−B, and the converging lens 71, the second lens 75, and the second photodetection means 72 are disposed, then the moved distance of the specific incidence angle due to a fluctuation in the interface develops as the spot movement quantity on the second photodetection means 72. To satisfy A=B or A=−B, it is necessary to install the converging lens 71, the second lens 75, and the second photodetection means 72 so that distances L, d0, d1, and d2 and the focal distances f1 and f2 are d1=f1, d2=f2, and d0=f1+L.

If, as in the eleventh embodiment, the tilt and vertical shift quantity of the interface 11a are obtained by utilizing the two lenses, then a measured value in which errors due to the quantity of fluctuation of the interface 11a has been corrected can be obtained and therefore ATR measurements can be performed with a higher degree of accuracy.

FIG. 17 shows measuring apparatus constructed according to a twelfth embodiment of the present invention.

The tilt measurement means of the measuring apparatus of the twelfth embodiment is constructed of a lens 80 for collecting a light beam L1 reflected at the light entrance surface 11b of the dielectric block 11 of a measuring chip 10, and second photodetection means 82 for detecting the light beam L1 converged by the lens 80. That is, the tilt measurement means of the measuring apparatus of the twelfth embodiment utilizes the portion of the light beam L1 reflected at the entrance surface 11b. Since the entrance surface 11b is tilted in proportion to the longitudinal tilt of the interface 11a which is a portion of the dielectric block 11, a fluctuation in the position, in the direction of arrow Q, of the reflected light on the second photodetection means 82 is proportional to the longitudinal tilt of the interface 11a.

Figure 18:
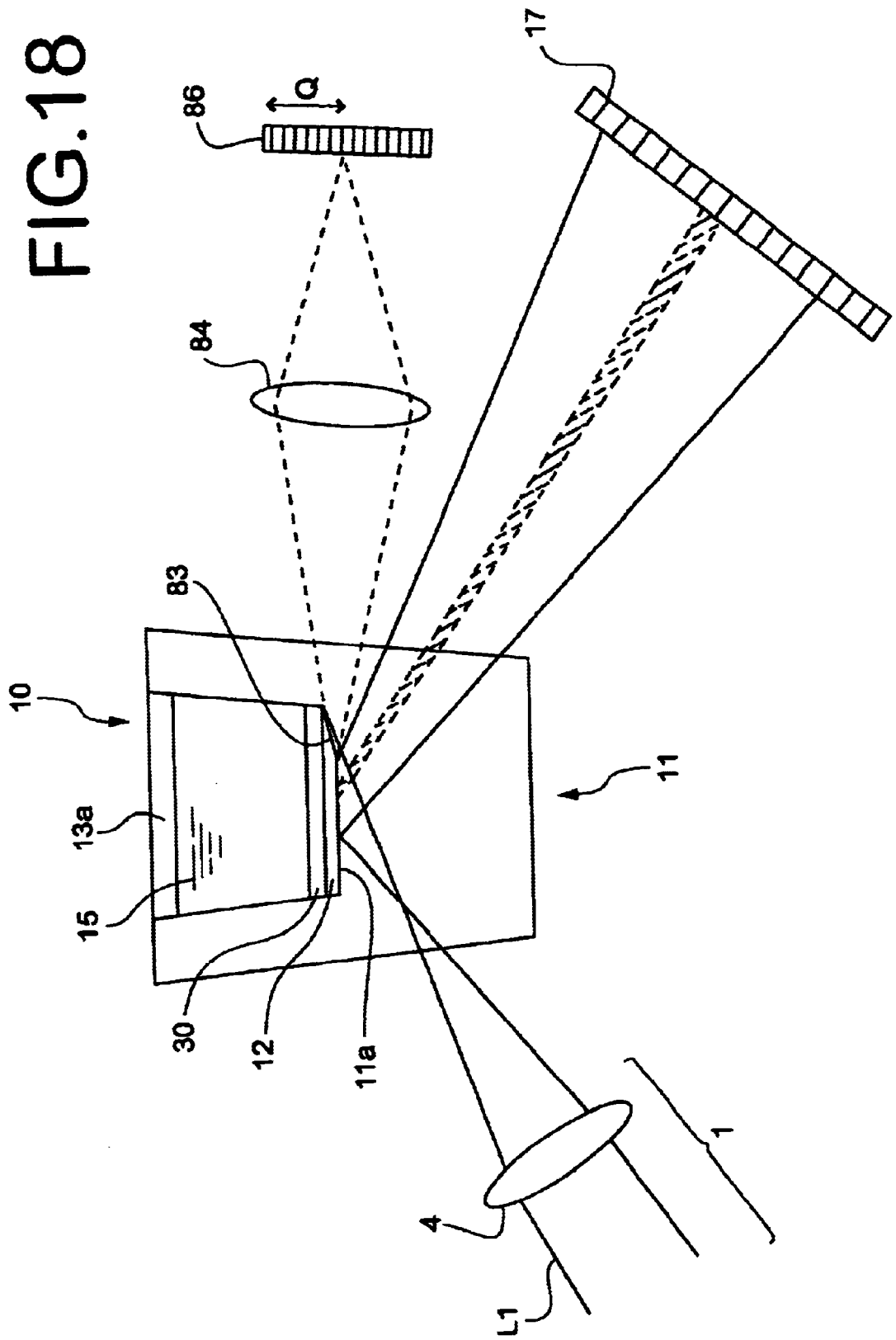
FIG. 18 is a side view showing a surface plasmon resonance sensor constructed according to a thirteenth embodiment of the present invention.

FIG. 18 shows a measuring apparatus constructed according to a thirteenth embodiment of the present invention.

The tilt measurement means of the measuring apparatus of the thirteenth embodiment is constructed of a reflecting surface 83 provided on a portion of the bottom surface of the target-substance holding hole 13a of a measuring chip 10, a lens 84 for collecting a light beam L1 reflected at the reflecting surface 83, and second photodetection means 86 for detecting the light beam L1 collected by the lens 84. In the thirteenth embodiment, the light beam L1 divergently strikes an interface 11a so that part of the light beam L1 strikes the reflecting surface 83. The light beam L1 incident on the interface 11a is reflected toward photodetection means 17 for measuring ATR. On the other hand, part of the light beam L1 incident on the reflecting surface 83 is reflected to the side of the second photodetection means 86, and the light beam is collected by the lens 84 and converges on the second photodetection means 86. Since the reflecting surface 83 is provided at a predetermined angle to the interface 11a and tilted in proportion to the longitudinal tilt of the interface 11a, a fluctuation in the position, in the direction of arrow Q on the second photodetection means 86, of the light beam reflected at the reflecting surface 83 is proportional to the longitudinal tilt of the interface 11a.

Figure 19:
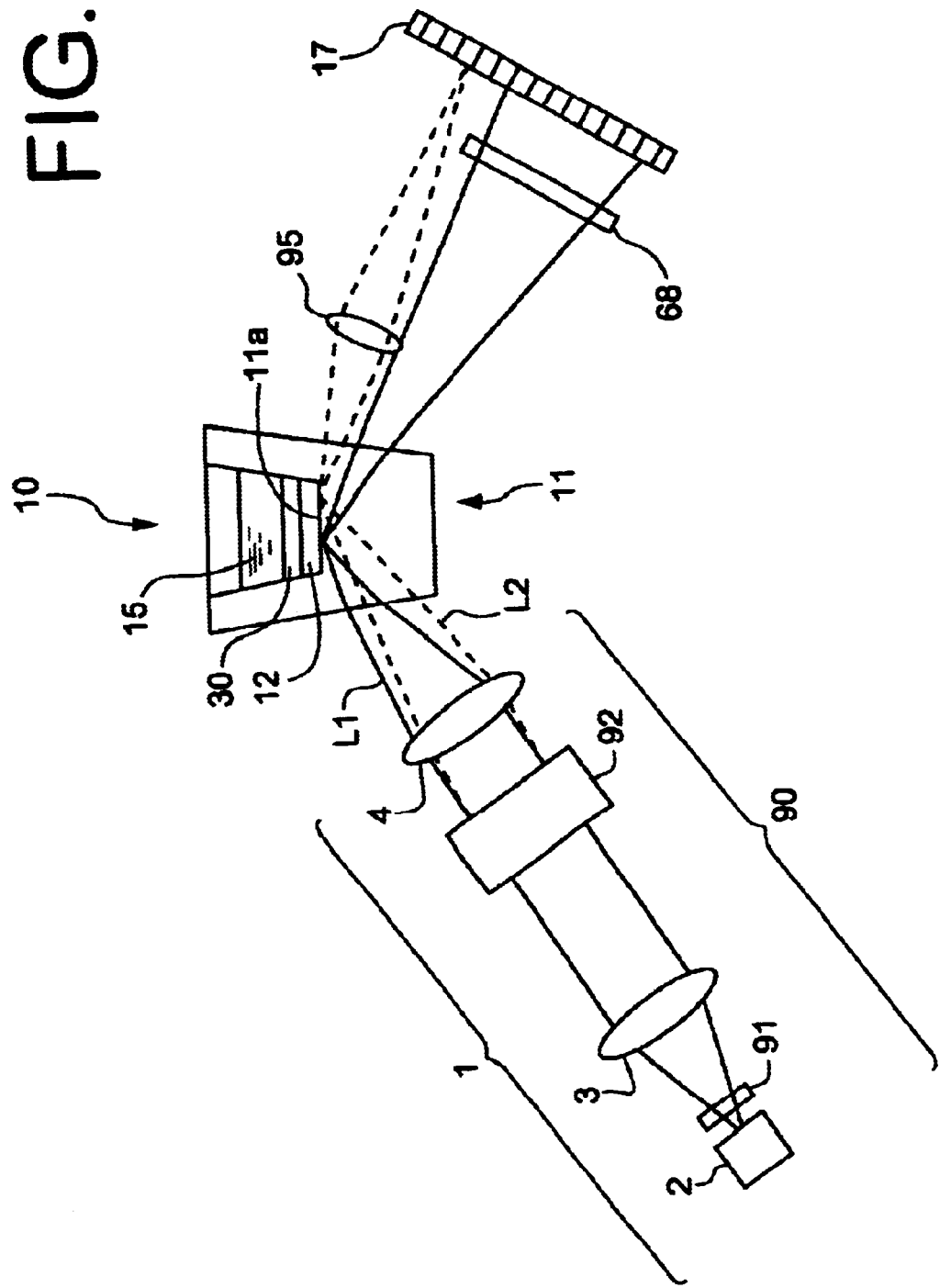
FIG. 19 is a side view showing a surface plasmon resonance sensor constructed according to a fourteenth embodiment of the present invention.

FIG. 19 shows a measuring apparatus constructed according to a fourteenth embodiment of the present invention.

The tilt measurement means of the measuring apparatus of the fourteenth embodiment is constructed of second beam incidence means 90, a condenser lens 95, and photodetection means 17. The second beam incidence means 90 is used for making a second light beam enter a dielectric block 11 so that the second light beam is totally reflected at an interface 11a. The condenser lens 95 is used for collecting the second light beam reflected at the interface 11a, and the photodetection means 17 is used for detecting the position of the light beam collected by the condenser lens 95.

The second beam incidence means 90, in addition to beam incidence means 1 for making a light beam L1 strike the interface 11a, is equipped with a quarter-wave plate 91 and a Wollaston polarizing prism 92. The quarter-wave plate 91 is used for converting a linearly polarized light beam, emitted from a light source 2, into a circularly polarized light beam. The Wollaston polarizing prism 92 is used for separating the circularly polarized light beam into an s-polarized light beam and a p-polarized light beam.

The light beam emitted from the light source 2 is circularly polarized by the quarter-waveplate 91 and is separated into a p-polarized light beam L1 and an s-polarized light beam L2 by the Wollaston polarizing prism 92. The p-polarized light beam L1 and the s-polarized light beam L2 strike the interface 11a at different positions.

The s-polarized light beam L2 is collected by the condenser lens 95 and converges on a portion of the photodetection means 17. Based on a fluctuation in the position of the s-polarized light beam L2 on the photodetection means 17, the longitudinal tilt of the interface 11a is measured. On the other hand, an analyzer 68 is disposed in the optical path of the p-polarized light beam L1 between the interface 11a and the photodetection means 17, whereby the influence of the s-polarized light beam L2 on the p-polarized light beam L1 is removed and the state of ATR is measured. In the fourteenth embodiment, the photodetection means 17 employs a photodiode array detectable over a wider range than when detecting the state of ATR, and detects the position of the s-polarized light beam L2 at a position which does not cross a place where the state of ATR is measured. However, additional photodetection means for detecting the s-polarized light beam L2 may be provided.

Figure 20:
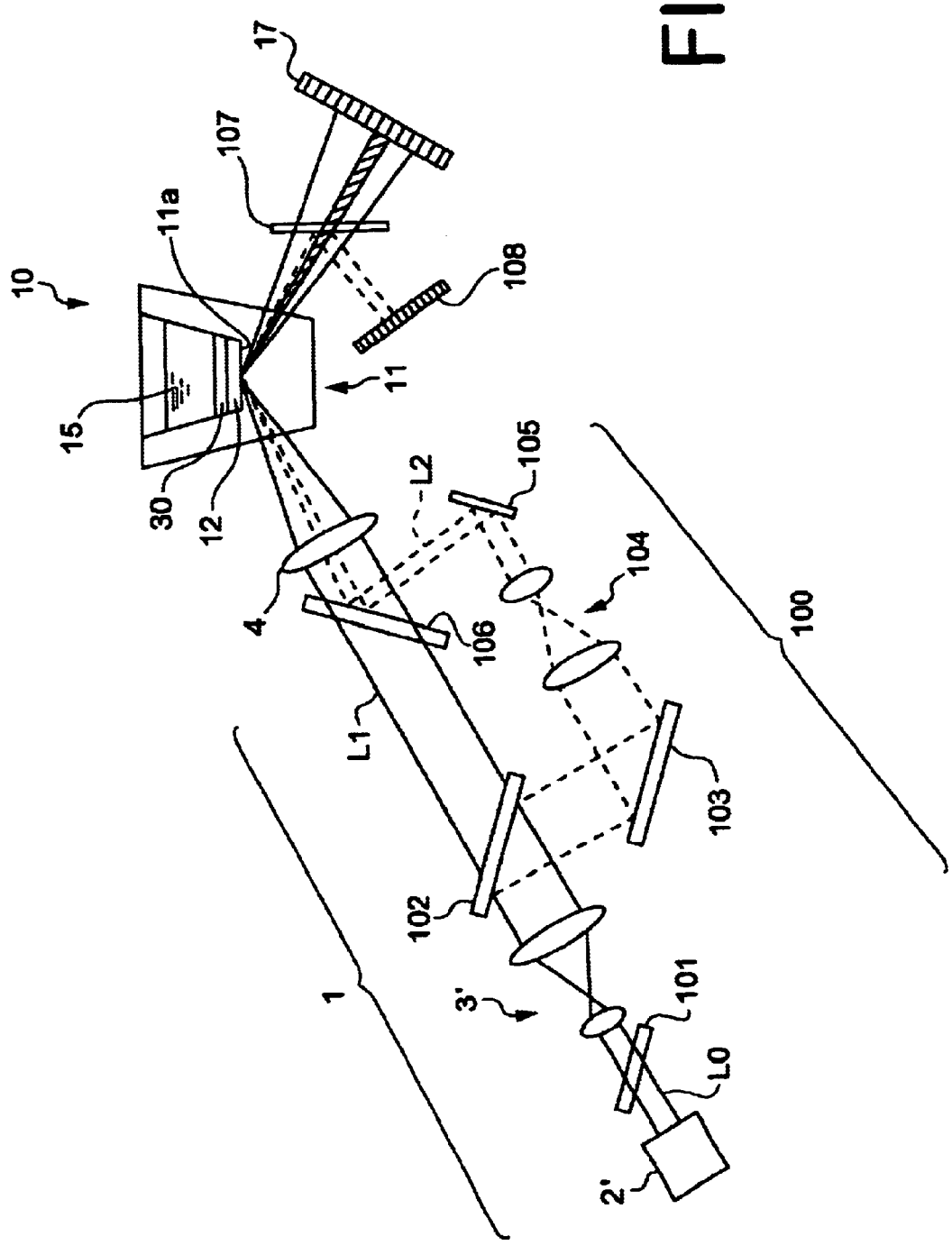
FIG. 20 is a side view showing a surface plasmon resonance sensor constructed according to a fifteenth embodiment of the present invention.

FIG. 20 shows a measuring apparatus constructed according to a fifteenth embodiment of the present invention.

The tilt measurement means of the measuring apparatus of the fifteenth embodiment is constructed of second incidence means 100, a polarization beam splitter (PBS) 107, and second photodetection means 108. The second incidence means 100 is used for making a small-diameter two-polarized light beam enter a dielectric block 11 as a second light beam so that the light beam is totally reflected at an interface 11a. The PBS 107 is used for reflecting the second light beam (s-polarized light beam) L2 reflected at the interface 11a, and transmitting a light beam (p-polarized light beam) L1 therethrough. The second photodetection means 108 is used for detecting the position of the second light beam L2 reflected by the PBS 107.

In the fifteenth embodiment, beam incidence means 1 is constructed of a light source 2' for emitting a small-diameter parallel light beam as a p-polarized light beam, a beam expander system 3' for expanding the diameter of the light beam, and a condenser lens 4 for making a p-polarized light beam L, transmitted through a PBS 102 to be described later, strike the interface 11a.

The second beam incidence means 100, in addition to the beam incidence means 1 for making the light beam L1 strike the interface 11a, is equipped with a quarter-wave plate 101, a PBS 102, mirrors 103, 105, 106, and a reduction optics system 104. The quarter-wave plate 101 is used for converting the linearly polarized light beam L0, emitted from the light source 2', into a circularly polarized light beam. The PBS 102 is used for transmitting a p-polarized light beam therethrough and reflecting an s-polarized light beam. The mirrors 103, 105, 106 are used for reflecting the s-polarized light beam L2. The reduction optics system 104 is used for reducing the diameter of the s-polarized light beam L2.

The linearly polarized light beam L0 emitted from the light source 2' is circularly polarized by the quarter-wave plate 101 and is expanded by the beam expander system 3'. The expanded light beam is separated into a p-polarized light beam L1 and an s-polarized light beam L2 by the PBS 102. The p-polarized light beam L1 is transmitted through the PBS 102, and the s-polarized light beam L2 is reflected. After the s-polarized light beam L2 is reduced in diameter by the reduction optics system 104, it is returned to the optical path of the p-polarized beam L1 and strikes the interface 11a.

The s-polarized light beam L2 reflected at the interface 11a is reflected by the PBS 107 and is detected by the second photodetection means 108. Based on a fluctuation in the position of the s-polarized light beam L2 on the second photodetection means 108, the longitudinal tilt of the interface 11a is measured.

The optical components of the second beam incidence means 100 maybe modified in various ways. For instance, as shown in FIG. 21, the mirrors 103, 105, and 106 of the second beam incidence means 100 may be changed in tilt and position to change the direction of the optical path of the second light beam L2.

Figure 22:
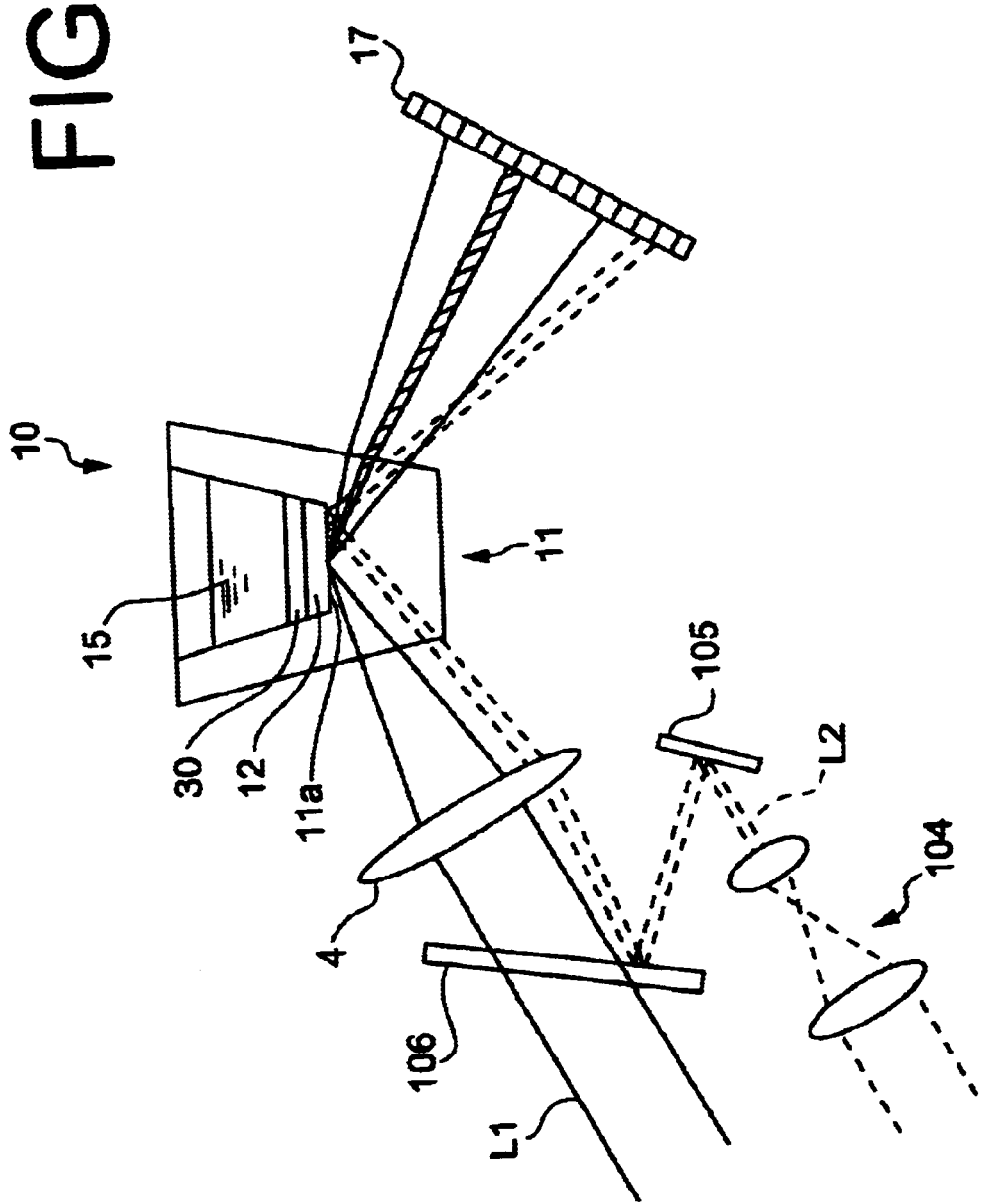
FIG. 22 is a side view showing a second modification of the surface plasmon resonance sensor of the fifteenth embodiment.

In addition, if as shown in FIG. 22, the tilts of the reflecting surfaces of the mirrors are changed so that the second light beam L2 is passed through a lens 4, the second light beam L2 strikes the interface 11a at a position shifted greatly from the position of incidence of the p-polarized light beam L1. Since the optical path of the second light beam L2 reflected at the interface 11a is shifted from that of the p-polarized light beam L1, there is no need to provide the PBS 107 on the side of the photodetection means 17. Furthermore, a portion of the photodetection means 17 can be utilized to detect the position of the second light beam L2.

Figure 21:
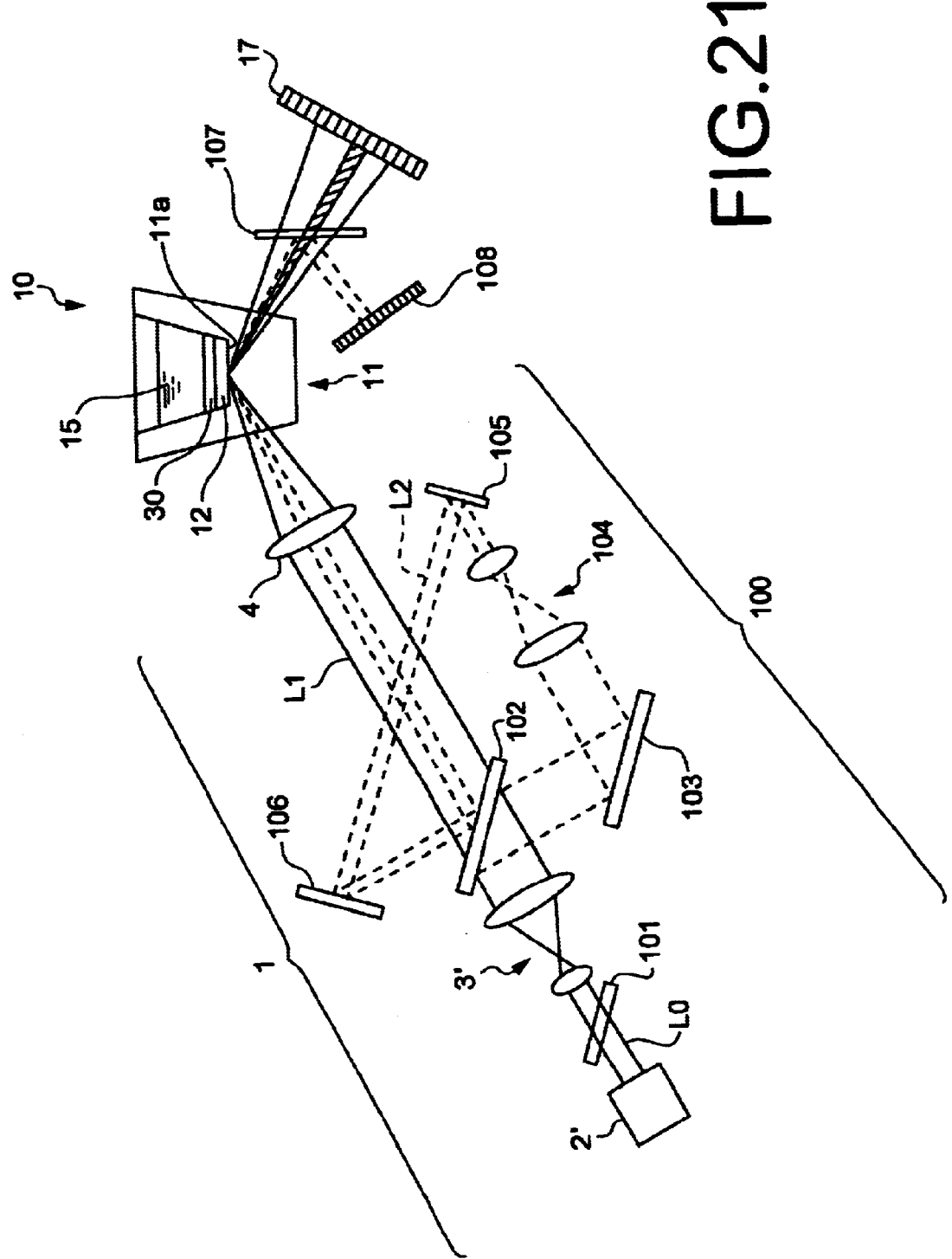
FIG. 21 is a side view showing a first modification of the surface plasmon resonance sensor of the fifteenth embodiment.
Figure 23:
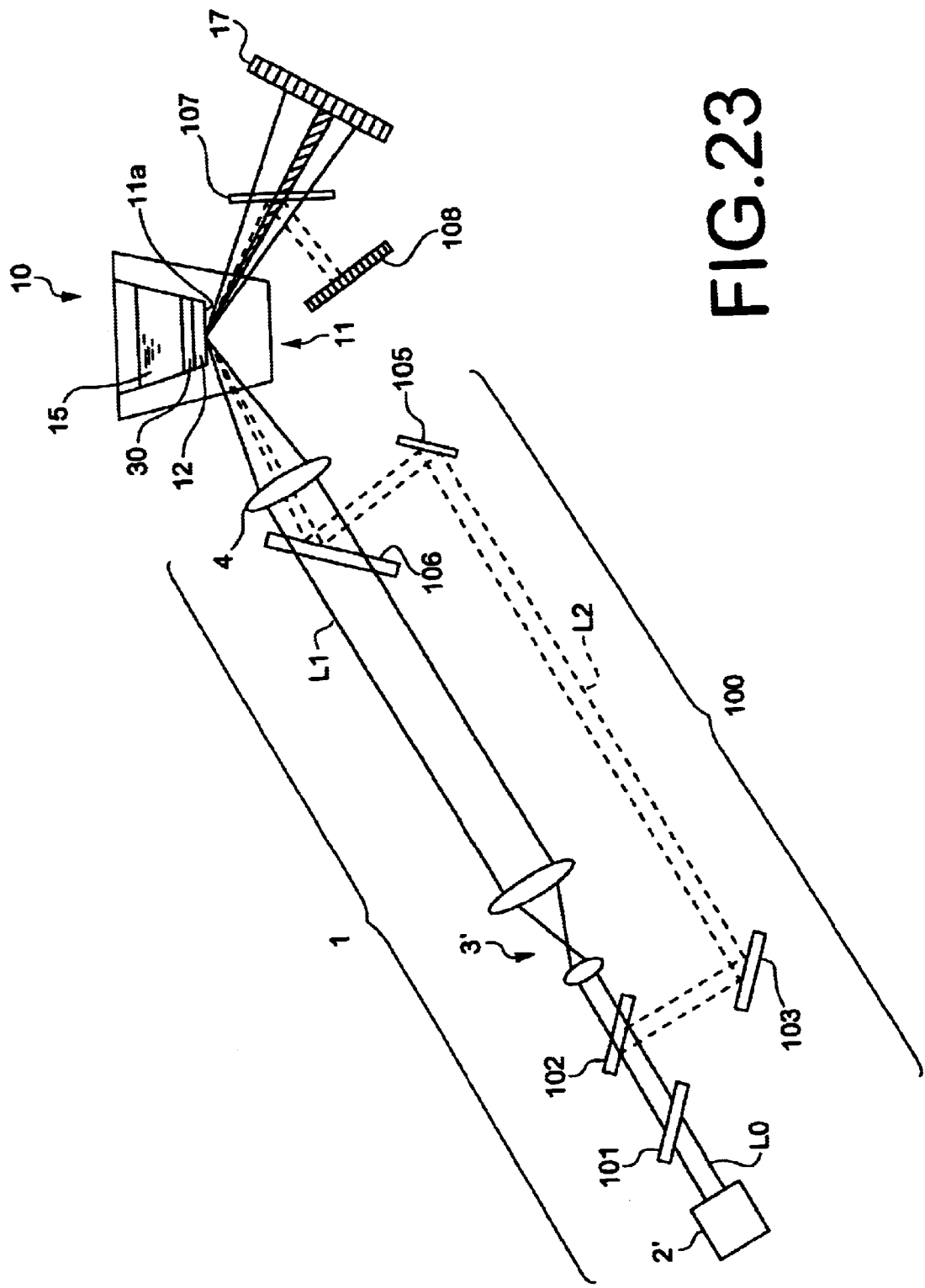
FIG. 23 is a side view showing a third modification of the surface plasmon resonance sensor of the fifteenth embodiment.

In the measuring apparatuses shown in FIGS. 20 to 22, the light beam L0 emitted from the light source 2' is expanded by the beam expander system 3' and is separated into an s-polarized light beam and a p-polarized light beam. However, if as shown in FIG. 23, the circularly polarized light beam L0 is separated into a p-polarized light beam L1 and an s-polarized light beam L2 by a PBS 102 before it is expanded, and only the p-polarized light beam L1 enters the beam expander system 3', the second beam incidence means becomes structurally simpler.

Figure 24:
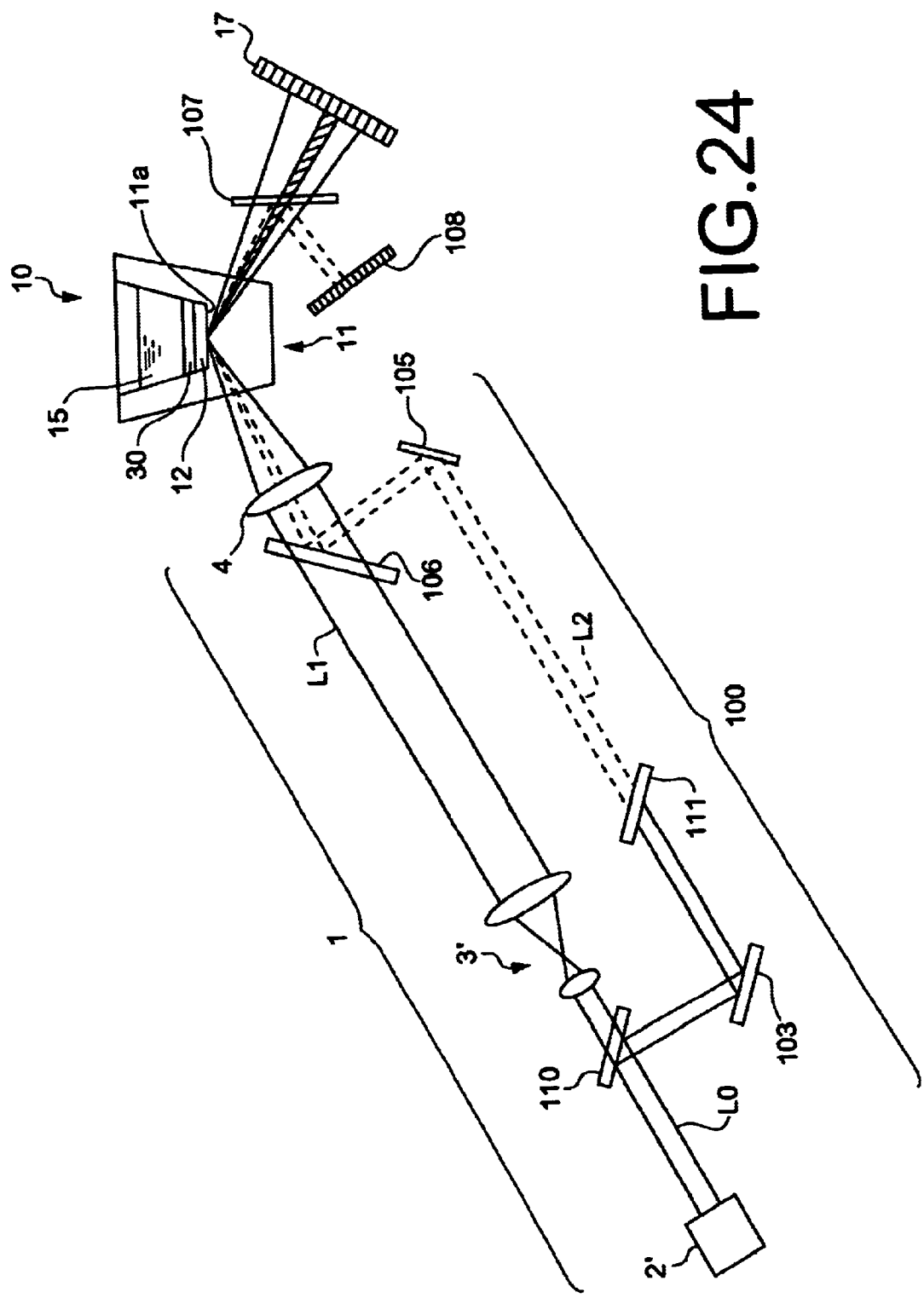
FIG. 24 is a side view showing a fourth modification of the surface plasmon resonance sensor of the fifteenth embodiment.

In addition, as shown in FIG. 24, a linearly polarized light beam (p-polarized light beam) L0 emitted from a light source 2' may be separated into two light beams by a half mirror 110 before it is converted into a circularly polarized light beam. In this case, one of the two light beams is expanded by a beam expander system 3' and used as a light beam L1 for measurement, while the other is changed in polarization direction by a half-wave plate 111 and strikes an interface 11a.

Figure 25:
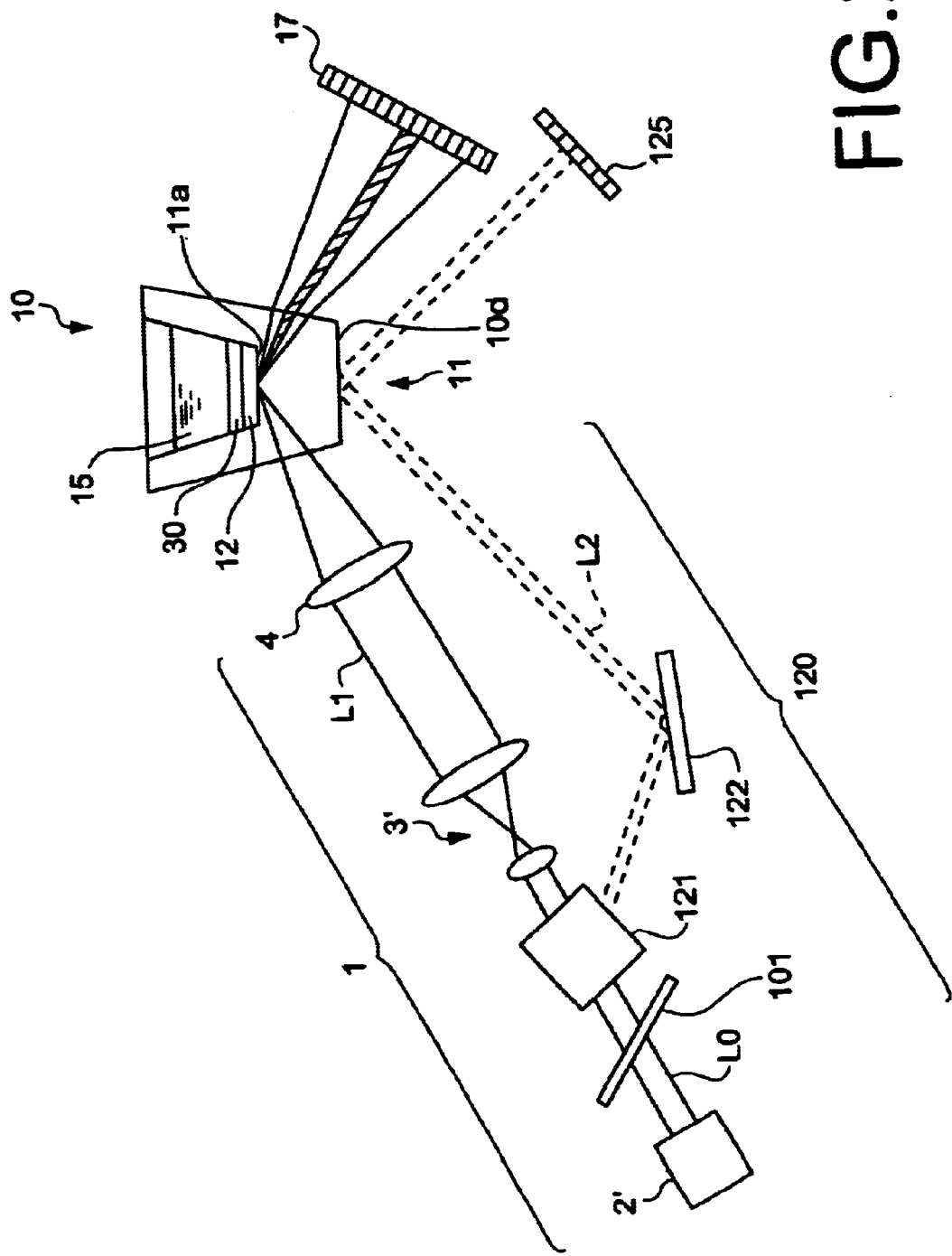
FIG. 25 is a side view showing a surface plasmon resonance sensor constructed according to a sixteenth embodiment of the present invention.

FIG. 25 shows a measuring apparatus constructed according to a sixteenth embodiment of the present invention.

The tilt measurement means of the measuring apparatus of the sixteenth embodiment is constructed of a reflecting surface, second beam incidence means 120, and photodetection means 125. The reflecting surface is provided on the bottom surface 10d of a measuring chip. The second beam incidence means 120 is used for making a small-diameter s-polarized light beam strike the reflecting surface as a second light beam L2 so that the second light beam is totally reflected at an interface 11a. The photodetection means 125 is used for detecting the second light beam L2 reflected at the reflecting surface.

The second beam incidence means 120, in addition to beam incidence means 1 for making a light beam L1 strike an interface 11a, is equipped with a quarter-wave plate 101, a Wollaston polarizing prism 121, and a mirror 122. The quarter-wave plate 101 is used for converting the light beam L1, emitted from a light source 2, into a circularly polarized light beam. The Wollaston polarizing prism 121 is used for separating the circularly polarized light beam into a p-polarized light beam L1 and an s-polarized light beam L2. With this arrangement, the s-polarized light beam L2 strikes the bottom surface 10d of the measuring chip so that it is totally reflected at the bottom surface 10d.

In the tilt measurement means of the sixteenth embodiment, the bottom surface 10d of the measuring chip 10 (i.e., the bottom surface of a dielectric block 11) is used as the reflecting surface. The second light beam L2 strikes not the interface 11a, but the bottom surface 10d of the measuring chip 10 which tilts in proportion to the tilt of the interface 10a. A fluctuation in the position of the second light beam L2 reflected at the bottom surface 10d is detected to measure the longitudinal tilt of the interface 10a.

Note that if the second light beam L2 is reflected at the bottom surface 10d, the second light beam L2 does not necessarily need to be an s-polarized light beam.

In the embodiments shown in FIGS. 19 to 25, the second beam incidence means, for making an s-polarized light beam strike the interface or a predetermined surface to be tilted in proportion to the tilt of the interface, employs part of the light emitted from the light source 2 for emitting the light beam L1. However, another light source for emitting the second light beam L2 may be provided.

In the fourth through the sixteenth embodiments, a correction corresponding to the longitudinal tilt of the interface has been made as a method of compensating for errors due to the longitudinal tile. However, as in the second and third embodiments, adjustment of position may be performed on the beam incidence means, the photodetection means, and/or the measuring unit.

In the embodiments equipped with calculating means for obtaining a measured value in which a correction has been made according to a longitudinal tilt, it has been described that with the initial interface position as reference, a longitudinal tilt from the reference position is detected at the time of each measurement thereafter, and that a measured value in which errors due to the tilt have been corrected is obtained. However, an interface position at a predetermined measurement, other than the initial measurement, of a plurality of measurements may be used as reference. Similarly, a longitudinal tilt from the reference position is obtained during each measurement, and a measured value in which errors due to the tilt have been made is obtained. In addition, the average position of the interface obtained by a plurality of measurements may be used as reference. Likewise, a longitudinal tilt from the average position is detected and a correction is made according to the tilt.

If errors detected in measuring a tilt are held as correction data for each of measuring apparatuses, and a correction value employing the correction data is obtained as a tilt value when a tilt is measured, then accuracy of measurement can be further enhanced.

Furthermore, in the embodiments with the calculating means, when the tilt of the interface exceeds an allowable value, an alarm may be issued. In that case, adjustments to the beam incidence means, the measuring unit, and/or the photodetection means may be made.

In the tilt measurements and tilt corrections in the sensors of the first through the sixteenth embodiments, only the longitudinal tilt of the interface is detected and errors due to the longitudinal tilt are corrected. However, in addition to the longitudinal tilt of the interface 11a which changes the incidence angle of the light beam L1, there is a transverse tilt which changes the incidence position of the light beam L1 in a direction perpendicular to a plane including the direction in which the incidence angle is changed. The transverse tilt results in the shift, in the direction perpendicular to the direction in which photodiodes are arranged, of the light beam L1. Because of this, there are cases where the light beam L1 cannot be received by the photodetection means 17. To prevent such a case, embodiments to be described below are equipped with tilt detection means for detecting longitudinal and transverse tilts, and correction means for correcting the longitudinal and transverse tilts.

Figure 26:
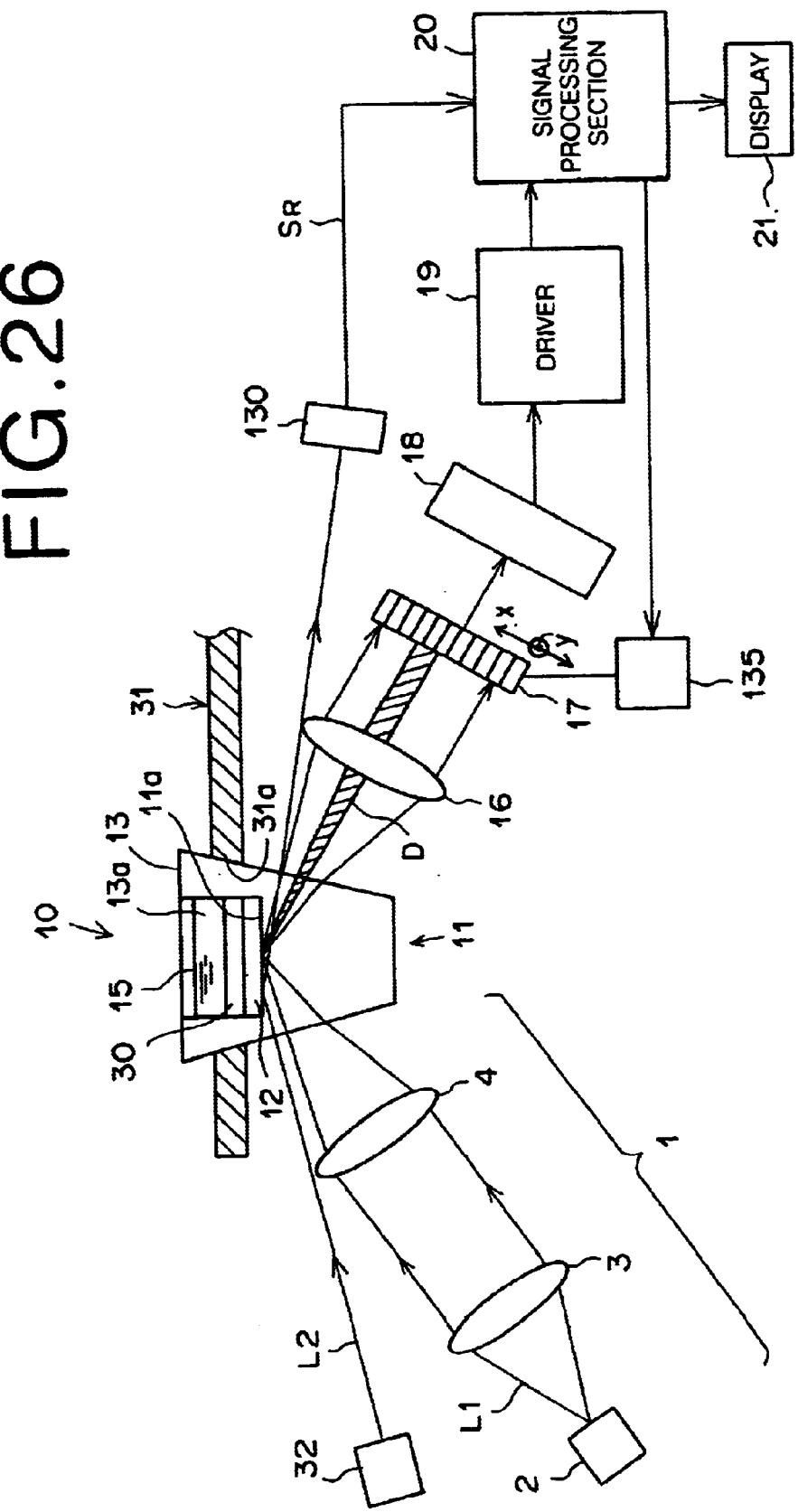
FIG. 26 is a side view showing a surface plasmon resonance sensor constructed according to a seventeenth embodiment of the present invention.

FIG. 26 shows a measuring apparatus constructed according to a seventeenth embodiment of the present invention.

The sensor of the seventeenth embodiment is nearly the same as the surface plasmon resonance sensor of the first embodiment, but differs in that in addition to the longitudinal tile of the interface, the transverse tilt is detected. The surface plasmon resonance sensor of the seventeenth embodiment is equipped with tilt measurement means, and means for correcting tilt errors (including inaccurate measurement). The tilt measurement means is constructed of second beam incidence means 32 and second photodetection means 130. The second beam incidence means 32 is used for making a second light beam L2 enter a dielectric block 11 so that the second light beam L2 is totally reflected at the interface 11a of the dielectric block 11. The second photodetection means 130 is used for detecting the second light beam L2, output from the second beam incidence means 32 and reflected at the interface 11a.

Figure 27:
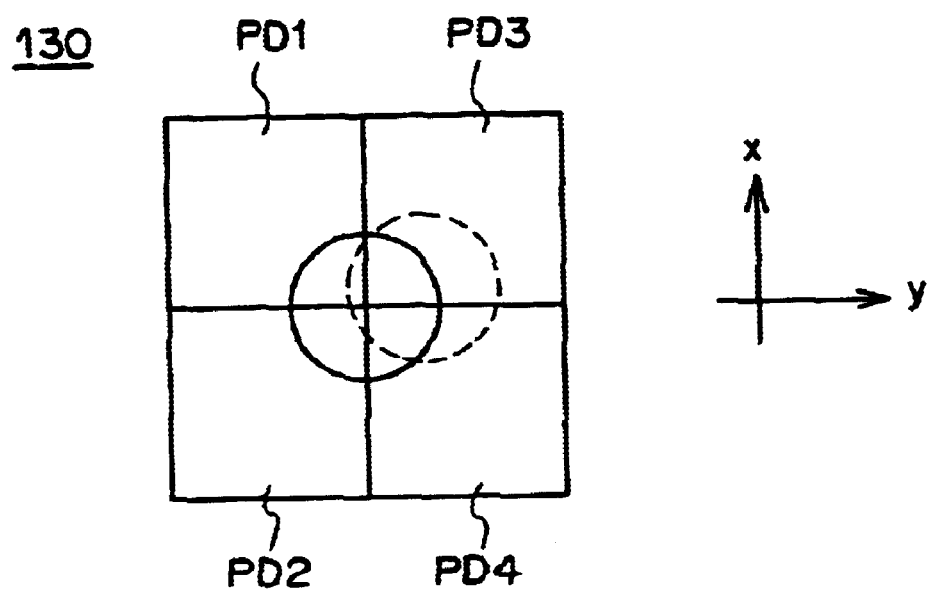
FIG. 27 is a schematic diagram showing the light receiving surface of the second photodetection means of the surface plasmon resonance sensor shown in FIG. 26.

The second photodetection means 130 is constructed, for example, of a position sensor consisting of a four-piece photodiode, and is used for detecting a two-dimensional fluctuation in the position of the light beam L2 incident on the light-receiving surface thereof. FIG. 27 schematically illustrates the light-receiving surface of the second photodetection means 130. As illustrated in the figure, the second photodetection means 130 consists of four photodiodes PD1, PD2, PD3, and PD4 and detects the position of a light beam from the quantity of the light received by each photodiode. More specifically, a shift in the x-direction (the longitudinal tilt of the interface) can be calculated from the difference between an addition signal of PD1 and PD3 and an addition signal of PD2 and PD4, and a shift in the y-direction (the transverse tilt of the interface) can be calculated from the difference between an addition signal of PD1 and PD2 and an addition signal of PD3 and PD4.

Note that the second light beam L2 for tilt measurement strikes the interface as an s-polarized light beam so that the polarization direction thereof differs from that of the light beam L1.

Means for correcting tilt errors is constructed of position adjustment means and calculating means. The position adjustment means functions as transverse adjustment means for correcting the shift, in the y-direction, of the light-received position on the photodetection means 17 resulting from a transverse tilt, and is used for moving the photodetection means 17 in the direction of arrow y to adjust the position of the photodetection means 17. The calculating means is used for obtaining a measured value in which errors due to a longitudinal tilt have been corrected.

That is, the position adjustment means is constructed of photodetection means 17 movable in the y-direction, and drive means 135 for moving the photodetection means 17. The drive means 135 moves and adjusts the photodetection means 17 in response to a signal from a signal processing section 20, which receives a signal from the second photodetection means 130 for tilt measurement and calculates the shift, in the y-direction, of the light beam L2. The calculating means is constructed of the signal processing section 20. As with the case of the aforementioned first embodiment, the signal processing section 20 obtains a signal output from the second photodetection means 130, calculates the shift, in the x-direction, of the light beam L2, and adds a correction signal, for correcting the tilt of the interface 11a, to a signal output from the photodetection means 17 for detecting a surface plasmon resonance signal. In this manner, the signal processing section 20 obtains an accurate value in which errors have been corrected. Since the calculations are the same as those in the first embodiment, a description thereof is omitted.

The measurement of a tilt, adjustment of position, etc., are performed as follows. First, when a first measurement of the sample 15 is made, settings are performed so that the second light beam L2, incident on the interface 11a by the second beam incidence means 32 and reflected at the interface 11a, is received at the center of the second photodetection means 130, as indicated by a solid line in FIG. 27. When a second measurement is made, the second light beam L2 reflected at the interface 11a is detected and a shift in the y-direction from the first detected position (the transverse tilt of the interface) is detected. Based on the shift in the y-direction, the position of the photodetection means 17 is adjusted in the y-direction. Based on a shift quantity obtained from a signal output from the second photodetection means 130 receiving the second light beam L2, only the position of the photodetection means 17 may be adjusted. When the first photodetection means 17 and the second photodetection means 130 are constructed so that they are moved in synchronization with each other, adjustments may be made so that the second light beam L2 is received at the center, in the y-direction, of the photodetection means 130. Thereafter, the shift, in the x-direction, of the second light beam L2 (i.e., the longitudinal tilt of the interface) is detected. Based on the shift in the x-direction, the signal processing section 20 obtains a measured value in which errors due to the longitudinal tilt of the interface 11a have been corrected.

When a third measurement and measurements thereafter are made, the transverse position of the photodetection means 17 is similarly adjusted based on the position of the second light beam L2 received by the second photodetection means 130. Thereafter, the state of ATR is measured, and a measured value in which errors due to the longitudinal tilt of the interface 11a have been corrected is obtained. In this manner, a measured value in which a compensation for the longitudinal and transverse tilts of the interface 11a has been made can be obtained and measurements can be performed more accurately.

Figure 28:
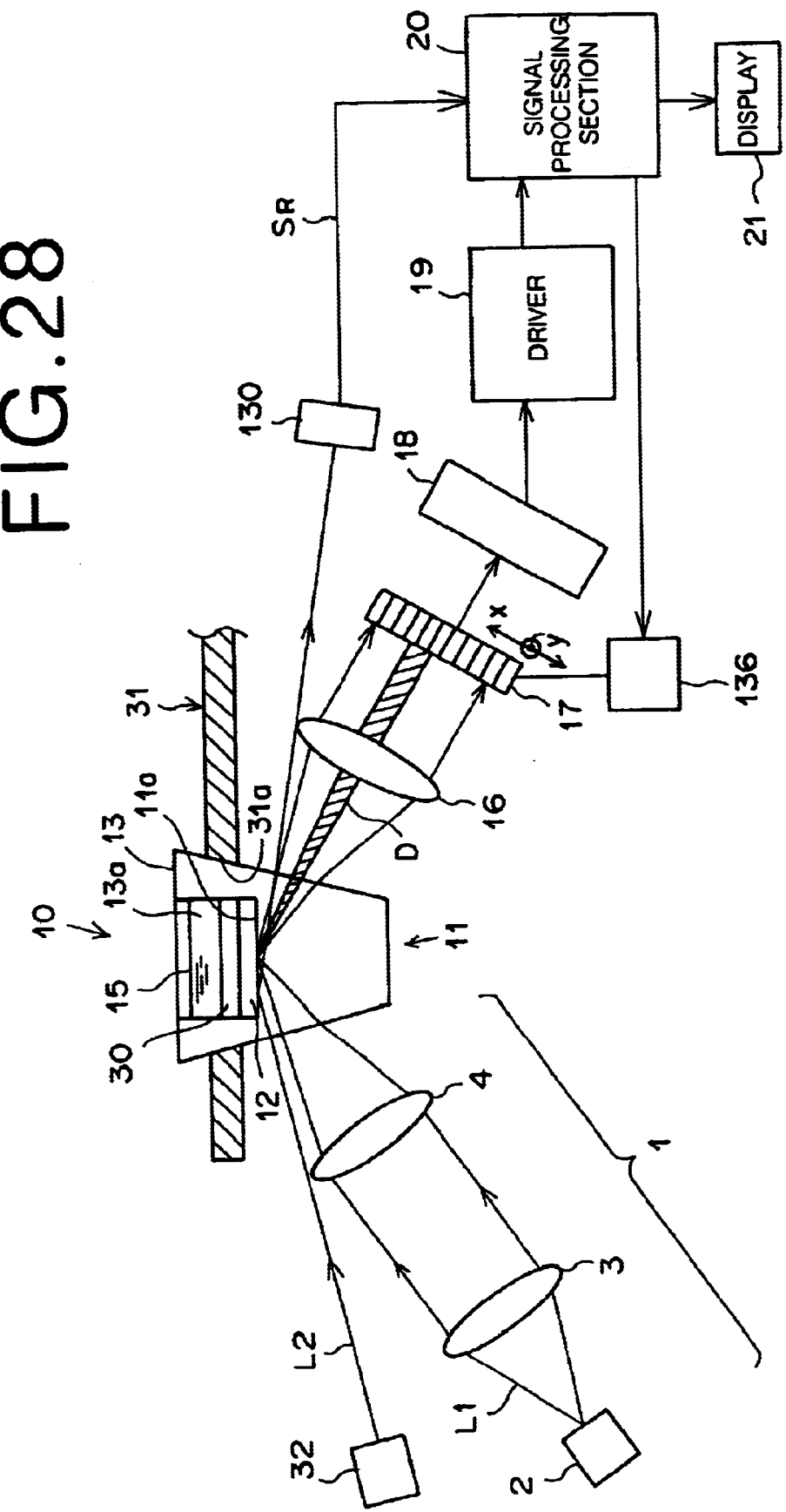
FIG. 28 is a side view showing a surface plasmon resonance sensor constructed according to an eighteenth embodiment of the present invention.

FIG. 28 shows a measuring apparatus constructed according to an eighteenth embodiment of the present invention.

The measuring apparatus of the eighteenth embodiment is nearly the same as the surface plasmon resonance sensor of the seventeenth embodiment, but means for correcting errors due to longitudinal and transverse tilts differs from that of the seventeenth embodiment. In the eighteenth embodiment, the transverse tilt and longitudinal tilt of the interface are simultaneously eliminated. As adjustment means for correcting errors due to longitudinal and transverse tilts (including inaccurate measurement), there is provided position adjustment means for moving first photodetection means 17 two-dimensionally in the direction of arrow x and the direction of arrow y perpendicular to the surface of the drawing sheet. That is, the position adjustment means is constructed of photodetection means 17 movable in the x-direction and y-direction, and drive means 136 for moving the photodetection means 17. The drive means 136 moves and adjusts the photodetection means 17 in response to a signal from a signal processing section 20, which receives a signal from second photodetection means 130 for tilt measurement and calculates the shift of the light beam L2.

The measurement of longitudinal and transverse tilts, adjustment of position, etc., are performed as follows. First, when a first measurement of a sample 15 is made, settings are performed so that a second light beam L2, reflected at the interface 11a, is received at the center of the second photodetection means 130. When a second measurement is made, the second light beam L2 reflected at the interface 11a is detected and a shift from the first detected position is detected. Based on the detected shift, the position of the photodetection means 17 is adjusted in the x-direction and y-direction. Based on a shift quantity obtained from a signal output from the second photodetection means 130 receiving the second light beam L2, only the position of the photodetection means 17 may be adjusted. Alternatively, the first photodetection means 17 and the second photodetection means 130 may be constructed so that they are moved in synchronization with each other, so that adjustments may be made so that the second light beam L2 is received at the center of the photodetection means 130. When a third measurement and measurements thereafter are made, the position of the photodetection means 17 is similarly adjusted based on the position of the second light beam L2 received by the second photodetection means 130. Thereafter, the state of ATR is measured. In this manner, a measured value in which a compensation for the longitudinal and transverse tilts of the interface 11a has been made can be obtained and measurements can be performed more accurately.

Note that the tilt of the interface 11a during a plurality of measurements occurs when a table for supporting the measuring chip is rotated, or when the supporting table, the light source, and the photodetectors are moved, as well as when the measuring chip is reset. As with the aforementioned embodiments, the longitudinal and transverse tilts of the interface 11a that occur in these cases are measured, and based on the measured tilts, a measured value in which corrections have been made according to the tilts can be obtained. In this manner, measurements can be performed with higher reliability.

In addition, in the case where a change in the aforementioned specific incidence angle (at which ATR occurs) due to only the liquid sample 15 is measured by measuring the state of ATR before the pouring of the liquid sample 15 into the measuring chip 10 and then subtracting the bulk effect of the measuring chip 10 from a value measured after the pouring of the liquid sample into the measuring chip 10, the reliability of measured values will be reduced, if longitudinal and transverse tilts of the interface 11a occur before and after the pouring of the liquid sample 15 into the measuring chip 10. In such a case, if the longitudinal and transverse tilts of the interface 11a are measured, and measured values are corrected based on the tilts, measurements can be made with high reliability.

Figure 29:
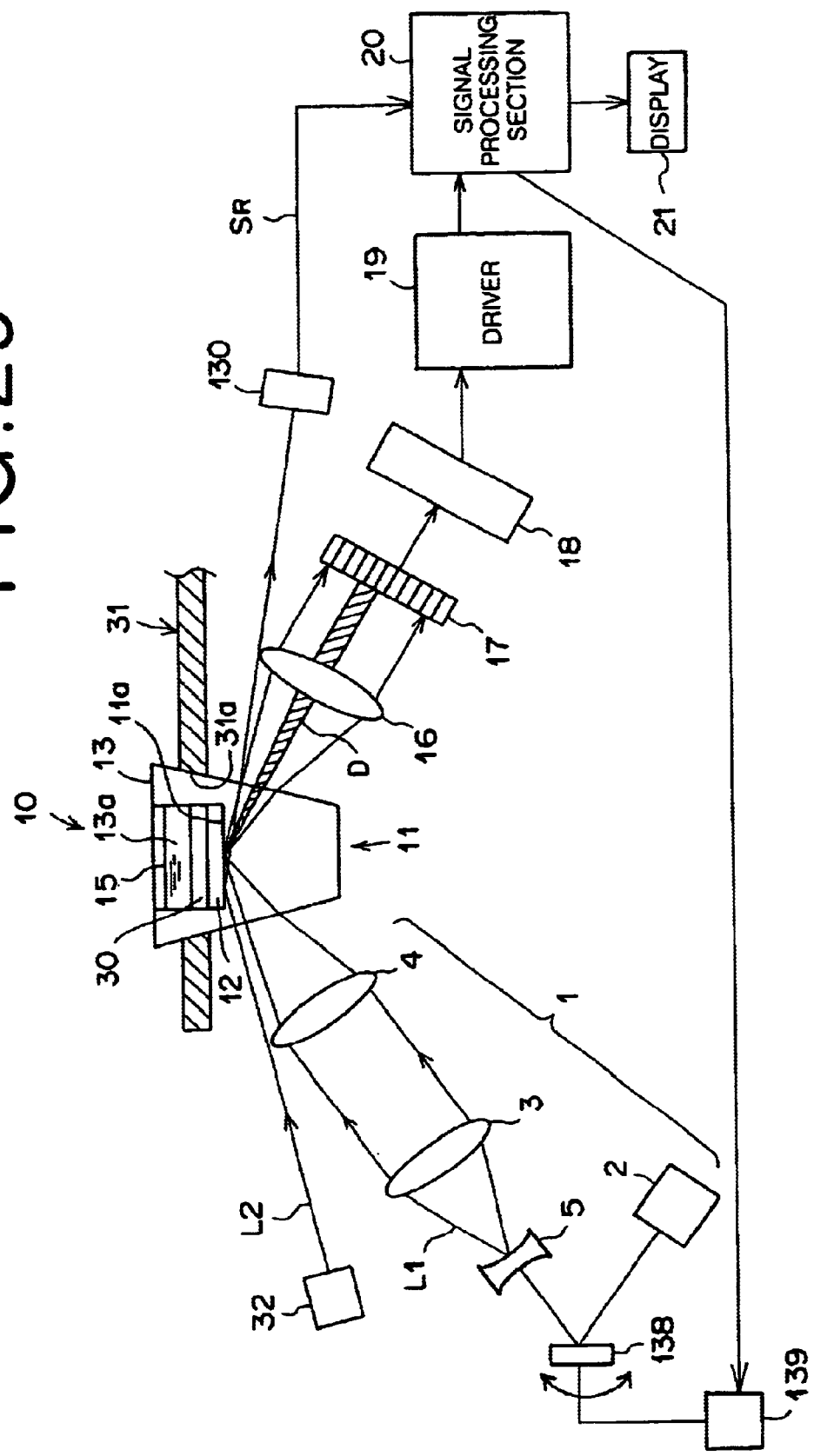
FIG. 29 is a side view showing a leaky mode sensor constructed according to a nineteenth embodiment of the present invention.

FIG. 29 shows a measuring apparatus constructed according to a nineteenth embodiment of the present invention.

As the means for correcting errors due to the longitudinal and transverse tilts of the interface, the measuring apparatus of the nineteenth embodiment is equipped with beam adjustment means for adjusting the incidence angle and incidence position of a light beam L1, not the photodetection means 17. The beam adjustment means is constructed of a tilt mirror 138 and drive means 139 for driving the tilt mirror 138. The tilt mirror 138 has a surface for reflecting the light beam L1 emitted from a light source 2, and the surface is rotatable in vertical and horizontal directions. The drive means 139 rotates the mirror 138 in response to a signal from a signal processing section 20, thereby adjusting the incidence angle and incidence position of the light beam L1. Note that the beam incidence means 1 of the nineteenth embodiment is constructed so that the small-diameter light beam L1 emitted from the light source 2 is diffused by a concave lens 5.

Thus, according to the longitudinal and transverse tilts of the interface obtained by the tilt measurement means, the incidence angle and incidence position of the light beam are adjusted, whereby a compensation for the longitudinal and transverse tilts of the interface is made.

As described above, in addition to adjusting the photodetection means 17 or beam incidence means 1, adjustments may be made so that the longitudinal and transverse tilts of the interface 11a are corrected by tilting the measuring chip 10 itself. In addition, by adjusting all or two of the photodetection means 17, beam incidence means 1, and measuring chip 10, measured values may be obtained in which a compensation for the longitudinal tilt of the interface 11a has been made as a whole.

Figure 30:
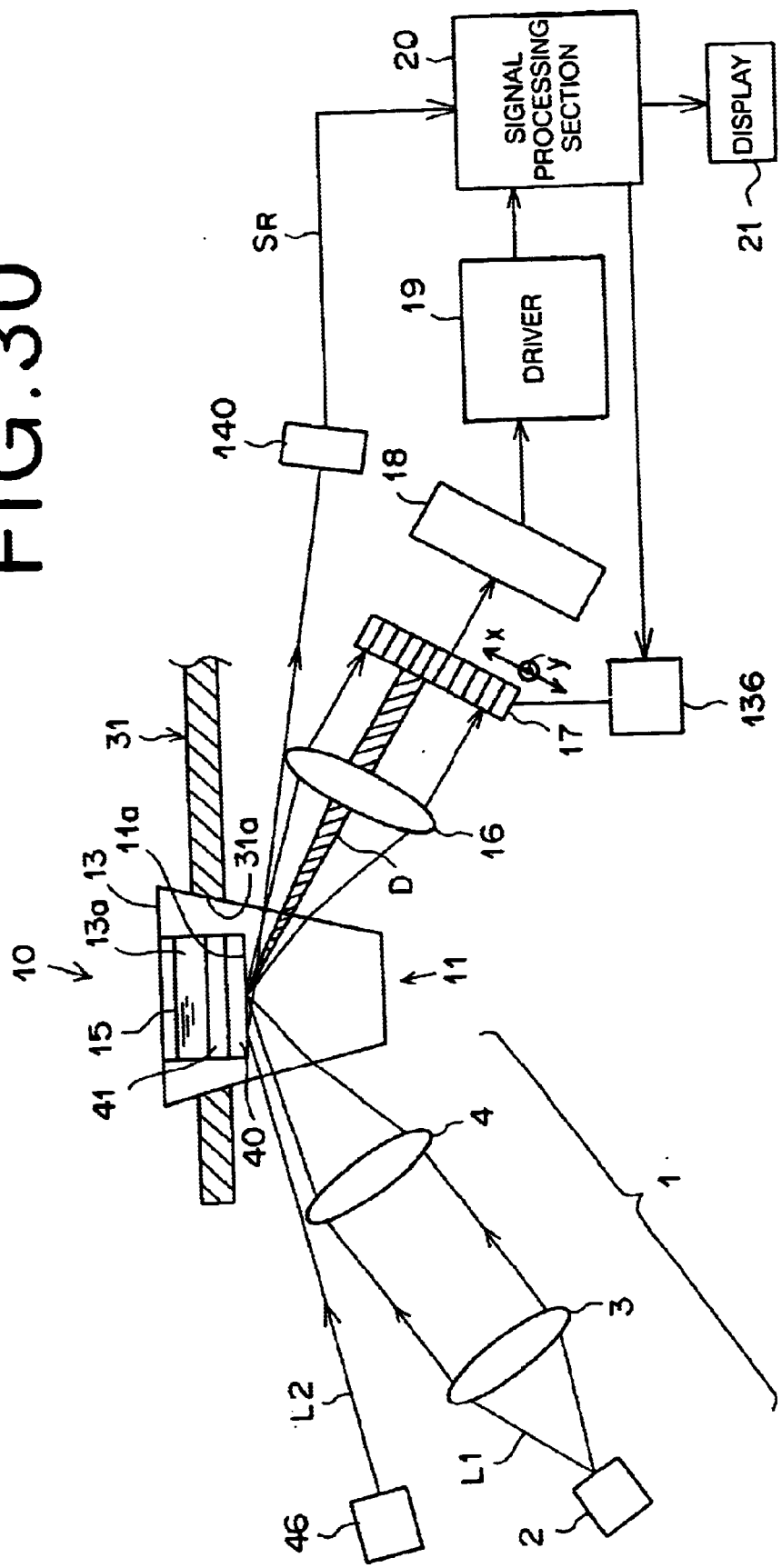
FIG. 30 is a side view showing a surface plasmon resonance sensor constructed according to a twentieth embodiment of the present invention.

FIG. 30 shows a measuring apparatus constructed according to a twentieth embodiment of the present invention, which is a leaky mode sensor similar to that of the fourth embodiment.

The leaky mode sensor of the twentieth embodiment is the similar to the leaky mode sensor of the fourth embodiment, but differs in that in addition to the longitudinal tile of the interface, the transverse tilt is detected. The leaky mode sensor of the twentieth embodiment is equipped with tilt measurement means, and means for correcting tilt errors (including inaccurate measurement). The tilt measurement means is equipped with a position sensor consisting of a four-piece photodiode as the second photodetection means 130.

Means for correcting the longitudinal and transverse tilts of the interface is the same as that employed in the surface plasmon resonance sensor of the seventeenth embodiment, and is therefore constructed of position adjustment means, which consists of photodetection means 17 movable in the x-direction and y-direction and drive means for driving the photodetection means 17. Each time a measurement is made, the longitudinal and transverse tilts of the interface are measured. Based on the tilts, the position of the photodetection means is adjusted. In this manner, measured values can be obtained in which a compensation for the longitudinal and transverse tilts of the interface has been made. Thus, measurements can be performed more accurately. Note that the second light beam L2 for tilt measurement has a wavelength differing from that of a light beam L1 for ATR measurement.

Figure 31:
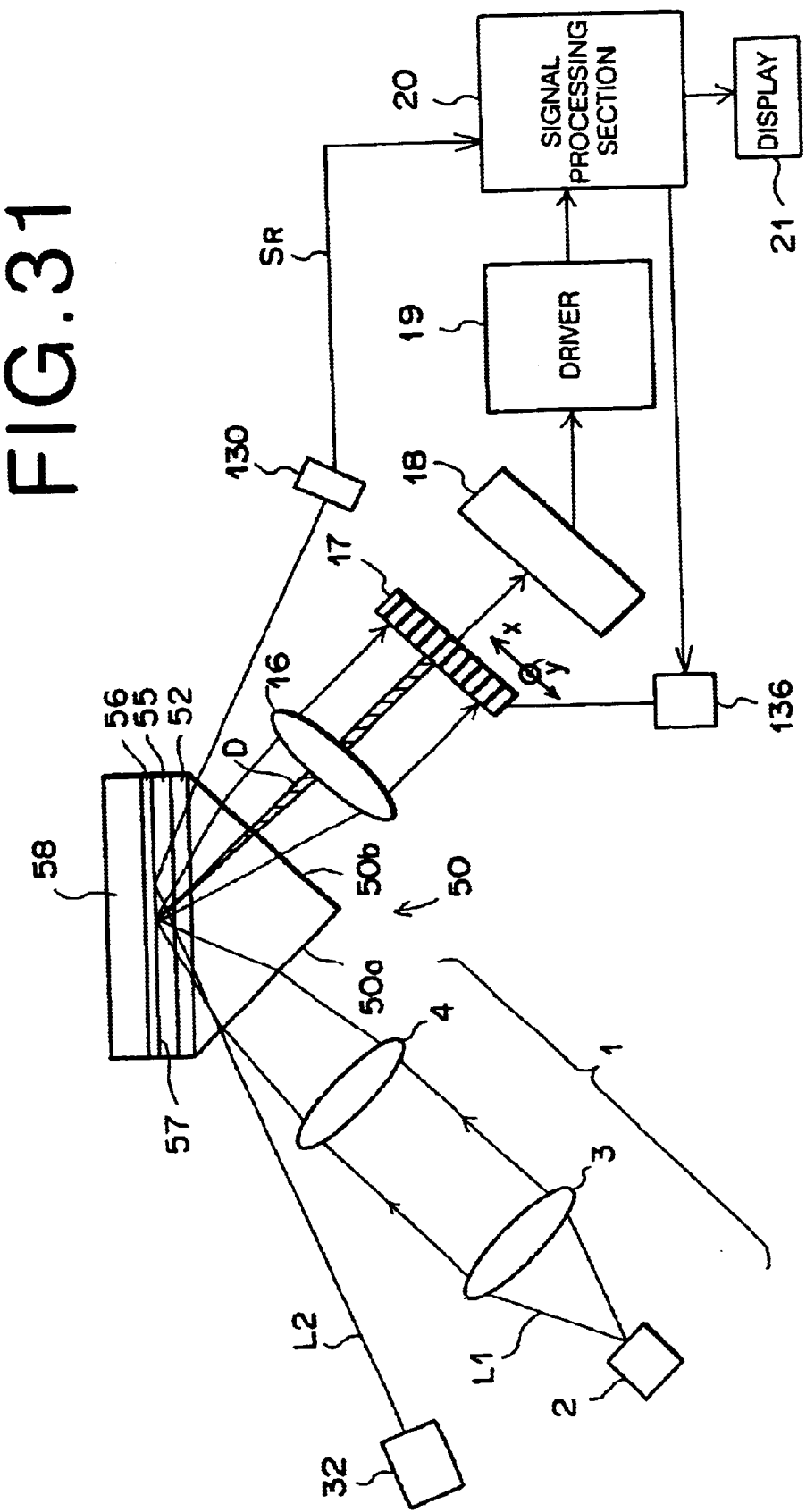
FIG. 31 is a side view showing a surface plasmon resonance sensor constructed according to a twenty-first embodiment of the present invention.

FIG. 31 shows measuring apparatus constructed according to a twenty-first embodiment of the present invention, which is a surface plasmon sensor similar to that of the fifth embodiment.

The twenty-first embodiment employs a measuring unit consisting of a trigonal prism 50 and a dielectric plate 55. The trigonal prism 50 extends in a direction perpendicular to the paper surface of FIG. 31, and the dielectric plate 55 is mounted on the top surface of the trigonal prism 50 through index-matching oil 52. The surface plasmon resonance sensor of this embodiment is capable of detecting the transverse tilt of an interface 57 in addition to the longitudinal tilt. As in the seventeenth embodiment, the surface plasmon resonance sensor is equipped with tilt measurement means, and means for correcting tilt errors (including inaccurate measurement). The tilt measurement means is constructed of second beam incidence means 32 and second photodetection means 130. The second beam incidence means 32 is used for making a second light beam L2 enter the prism 50 so that the second light beam L2 is totally reflected at the interface 57. The second photodetection means 130 consists of a four-piece photodiode and is used for detecting the second light beam L2, output from the second beam incidence means 32 and reflected at the interface 57. With this construction, a measured value can be obtained in which a compensation for errors due to the longitudinal and transverse tilts of the interface has been made.

Figure 32:
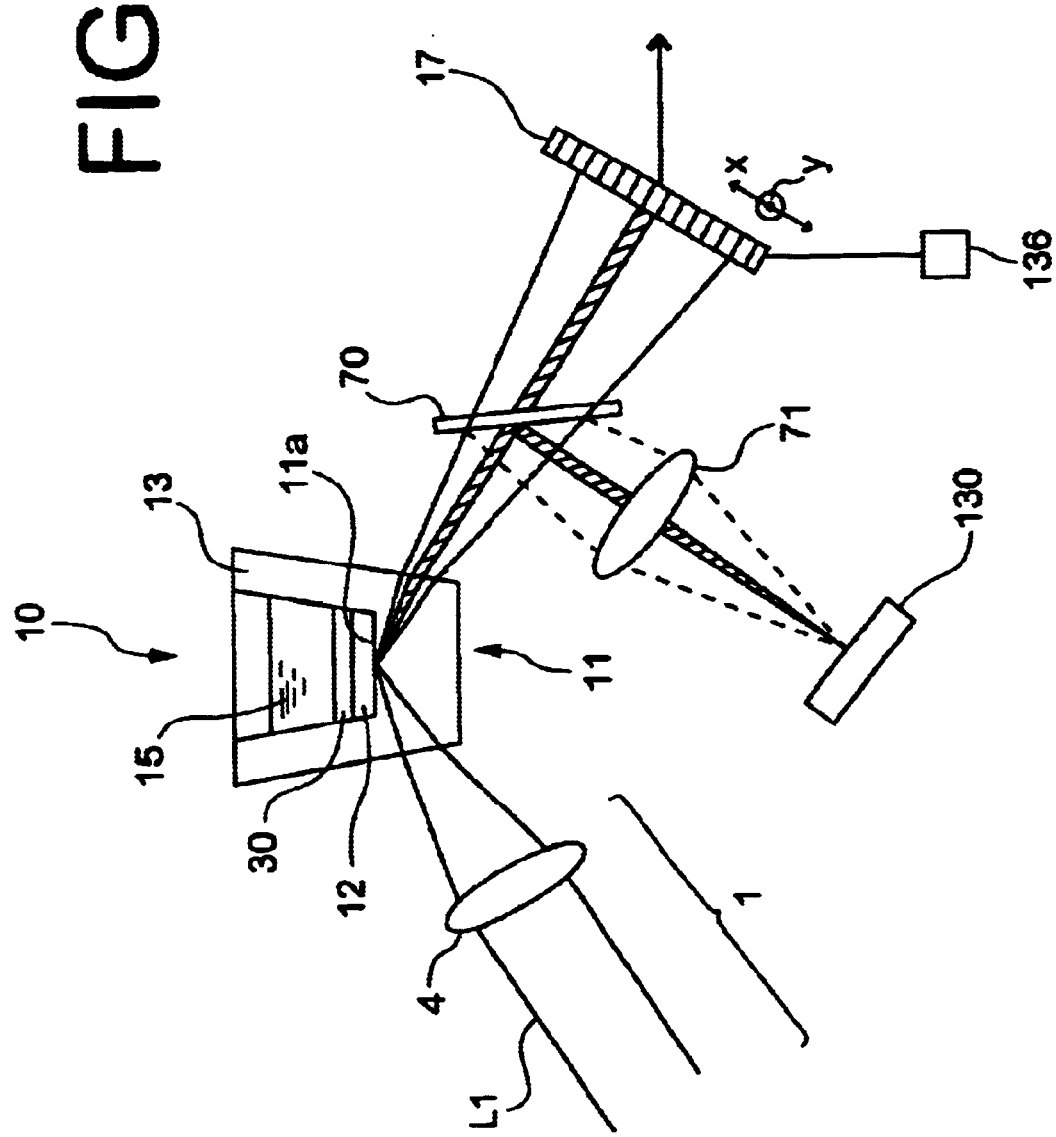
FIG. 32 is a side view showing a surface plasmon resonance sensor constructed according to a twenty-second embodiment of the present invention.
Figure 33:
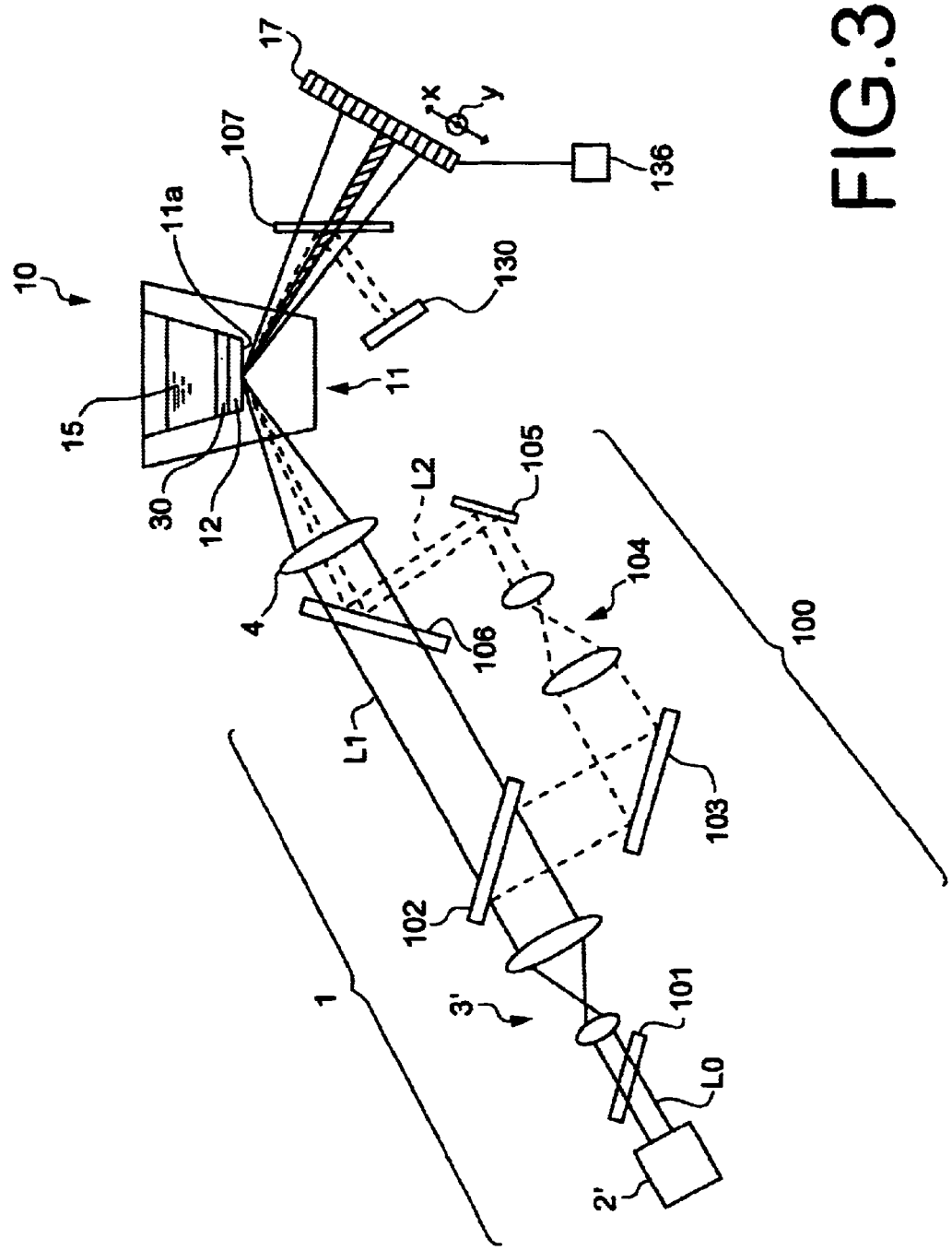
FIG. 33 is a side view showing a surface plasmon resonance sensor constructed according to a twenty-third embodiment of the present invention.
Figure 34:
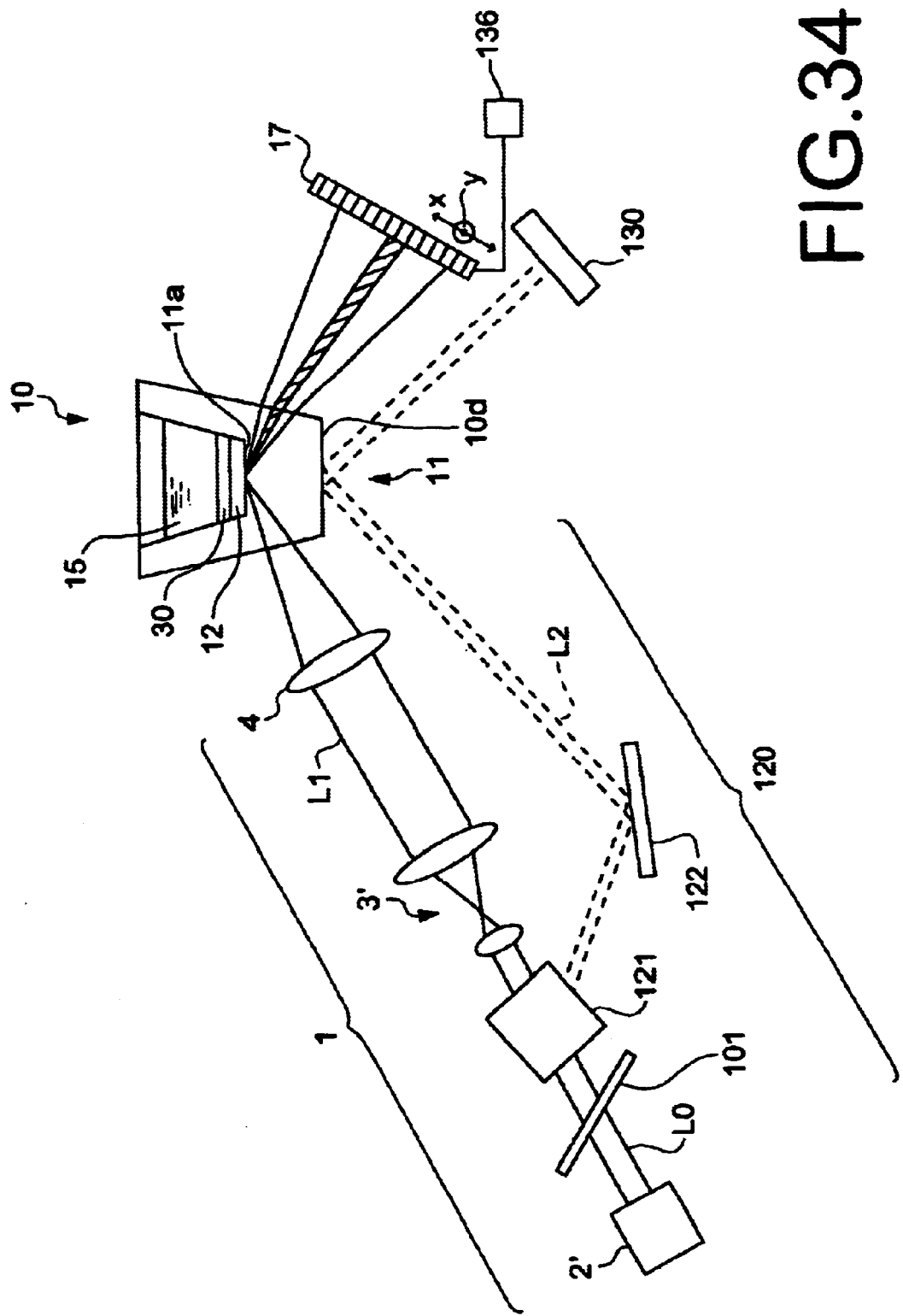
FIG. 34 is a side view showing a surface plasmon resonance sensor constructed according to a twenty-fourth embodiment of the present invention.

In the measuring apparatuses of the seventh through the sixteenth embodiments (excluding the eleventh embodiment), the second photodetection means 130 can employ a four-piece photodiode or two-dimensional sensor (such as a resistance photodetector, etc.) instead of a one-dimensional photodiode array, as shown in FIGS. 32 to 34. In addition, if first photodetection means 17 is movable in the x-direction and y-direction and drive means 36 for driving the photodetection means 17 to adjust the position of the means 17 is provided, both the longitudinal tilt and the transverse tilt of an interface 11a can be detected and accurately measured values can be obtained in which a compensation for errors due to the longitudinal and transverse tilts has been made.

Note that the measuring apparatuses according to the embodiments described above are of the type that makes a light beam enter an interface so that various angles of incidence are obtained with respect thereto; measures the light reflected at the interface; and measures the state of ATR by determining the angle of incidence at which a dark line occurs; thereby obtaining a measurement of the bonding state between a sample and a sensing medium. However, a construction may be adopted wherein the angle of incidence of a light beam is set at a predetermined angle that meets conditions for total internal reflection; and a light beam having various wavelengths, or a light beam having a variable wavelength is made to enter the interface; the light reflected at the interface is measured; and the state of ATR is measured for each wavelength; thereby obtaining a measurement of the bonding state between a sample and a sensing medium.

A different measuring apparatus that utilizes totally reflected light will be described, as the twenty third embodiment of the present invention.

Figure 35:
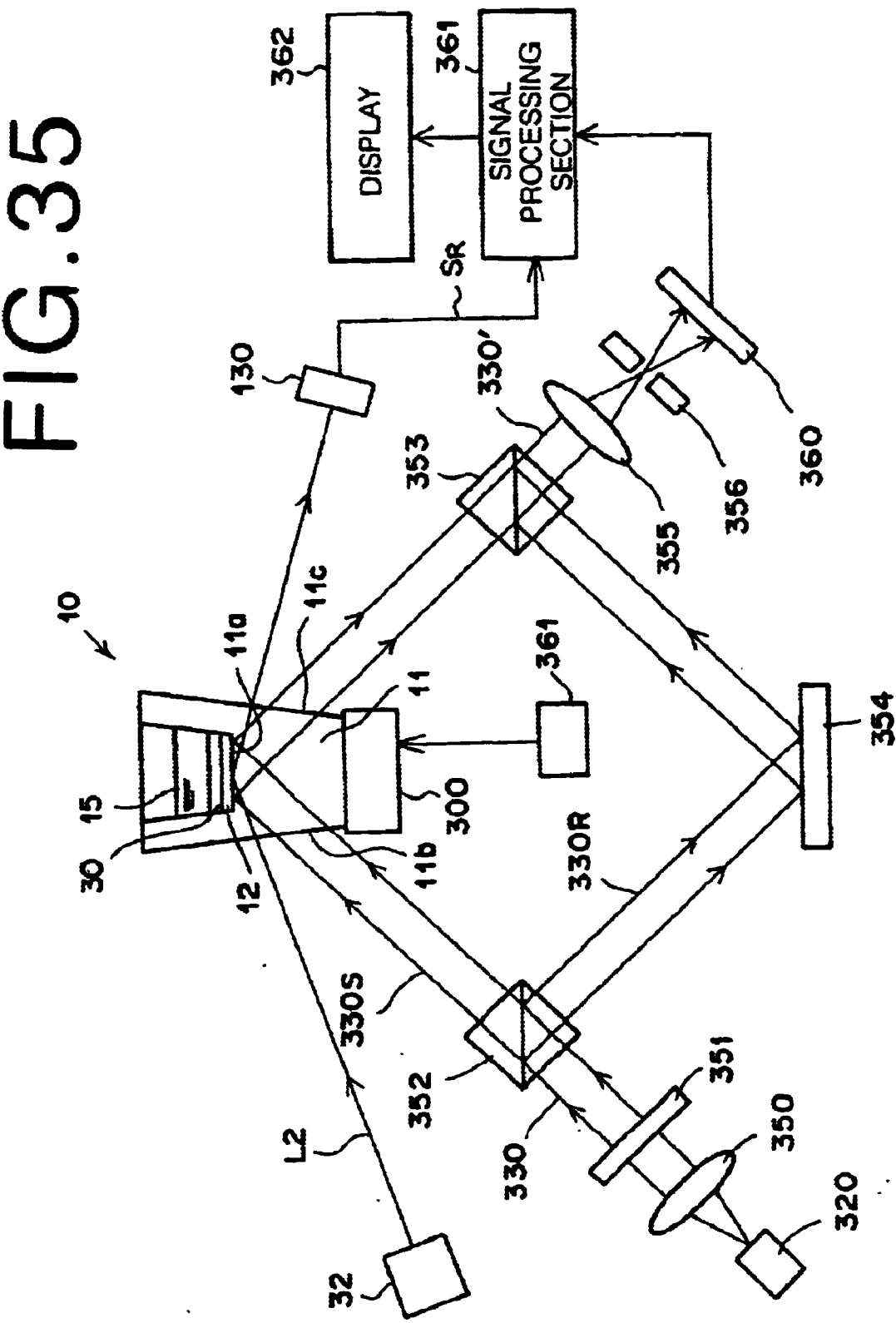
FIG. 35 is a side view showing a surface plasmon resonance sensor constructed according to a twenty-fifth embodiment of the present invention.

As shown in the side view of FIG. 35, the surface plasmon sensor of the present embodiment is equipped with a measurement chip 10 similar to that of the first embodiment as a measurement unit. The measurement chip 10 is positioned on a measurement unit support 300, which also serves as a tilt correcting stage.

A light source 320 is provided on the side of a light beam entrance surface 11b of a dielectric block 11 of the measuring chip 10, and a charged coupled device (CCD) 360 is provided on the side of a light exit surface 11c of the dielectric block 11 of the measuring chip 10. A collimating lens 350, an interference optical system, a condenser lens 355 and an aperture 356 is provided between the light source 320 and the CCD 360.

The interference optical system is constructed by a polarizing filter 351, a half mirror 352, a half mirror 353 and a mirror 354.

The CCD 360 is connected to a signal processing section 361, and the signal processing section 361 is connected to a display 362.

In the present measuring apparatus, means are provided for measuring and correcting errors (including inaccurate measurement) due to tilt in both the longitudinal and transverse directions, as in the eighteenth embodiment. The tilt measuring and correcting means is constructed of a second beam incidence means 32 and a second photodetection means 130. The second beam incidence means 32 causes a second light beam L2 to enter the dielectric block 11 so that the second light beam L2 is totally reflected at an interface 11athereof. The second photodetection means 130 detects the second light beam L2 reflected at the interface 11a. The measurement unit support 300 that supports the measurement chip 10 also acts as a tilt correction stage, which is the longitudinal and transverse tilt adjusting means for correcting errors (including inaccurate measurement) due to longitudinal and transverse tilt. This tilt correction stage performs positional adjustment of the measuring chip 10 according to instructions from the signal processing section 361.

Hereinafter, the operation undergone during measurement of a sample by the surface plasmon sensor according to the present embodiment will be described.

The light source 320 is driven, and a light beam 330 is emitted as a divergent light. The light beam 330 is collimated by the collimating lens 350, and enters the polarizing filter 351. After passing through the polarizing filter 351, the light beam 330 is divided by the half mirror 352 so that a portion thereof becomes a reference light beam 330R. The remaining portion of the light beam, 330S, is made to enter the interface 11a as p-polarized light. The light beam 330S totally reflected at the interface 11a and the reference light beam 330R reflected by the mirror 354 enter the half mirror 353 and are combined thereat. The combined light beam 330' is condensed by the condensing lens 355, passes through the aperture 356, and is detected by the CCD 360. At this time, the light beam 330' detected by the CCD 360 generates an interference fringe corresponding to the state of interference between the light beam 330S and 330R.

Multiple measurements are taken after dropping of a sample 15. By detecting a difference in the detected interference fringe, the bonding state between a specific substance within the sample 15 and a sensing medium 30 can be detected. That is, in this case, as the refractive index of the sensing medium 30 changes corresponding to the bonding state between the specific substance and the sensing medium 30, the state of interference between the light beam 330S and the reference light beam 330R changes when they are combined by the half mirror 353, the bonding state can be detected by observing the change in the interference fringe.

The signal processing section 361 determines whether a bonding reaction occurs based on the above principle, and the result of the determination is displayed on the display 362.

The method of detecting tilt of the interface 11a in the present embodiment is similar to that of the eighteenth embodiment. At every measurement, the second photodetection means 130 detects the tilt of the interface 11a. Corresponding to the detected tilt, the signal processing section 361 issues commands to the tilt correcting stage 300, which is driven to adjust the tilt of the measuring chip 10, thereby correcting the longitudinal and transverse tilt of the interface 11a. Because positional adjustments are thus made to the interface 11aq of the measuring chip 10, accurate measurements can be performed.

Finally, while the present invention has been described with reference to the preferred embodiments thereof, the invention is not to be limited to the details given herein, but may be modified within the scope of the invention hereinafter claimed.

What is claimed is:

1. A measuring apparatus comprising:
   a measuring unit equipped with a transparent dielectric block and a thin film layer formed on one surface of said dielectric block;

first beam incidence means for making a first light beam enter said dielectric block at various angles of incidence so that a condition for total internal reflection is satisfied at an interface between said dielectric block and said thin film layer; and first photodetection means for receiving a predetermined polarized light component of said first light beam totally reflected at said interface;

wherein said measuring unit is measured a plurality of times and a change in the state of attenuated total reflection during the plurality of measurements is detected;

and wherein said measuring apparatus further comprises:

tilt measurement means for measuring a longitudinal tilt of said interface which changes said incidence angles during said plurality of measurements; and calculating means for obtaining a measured value in which errors due to said longitudinal tilt have been corrected according to said longitudinal tilt measured by said tilt measurement means.

2. A measuring apparatus comprising:

a measuring unit equipped with a transparent dielectric block and a thin film layer formed on one surface of said dielectric block;

first beam incidence means for making a first light beam enter said dielectric block at an angle of incidence so that a condition for total internal reflection is satisfied at an interface between said dielectric block and said thin film layer; and first photodetection means for receiving a predetermined polarized light component of said first light beam totally reflected at said interface;

wherein said measuring unit is measured a plurality of times and a change in the state of attenuated total reflection during the plurality of measurements is detected;

and wherein said measuring apparatus further comprises:

tilt measurement means for measuring a longitudinal tilt of said interface which changes said incidence angles during said plurality of measurements; and adjustment means for making adjustments to said measuring unit, said first beam incidence means, and/or said first photodetection means so that errors due to said longitudinal tilt are corrected according to said longitudinal tilt measured by said tilt measurement means.

3. The measuring apparatus as set forth in either of claims 1 or 2, wherein said first beam incidence means is constructed to cause said first light beam to enter said interface at various angles of incidence;

said first photodetection means is constructed to measure a state of attenuated total reflection which occurs when said first light beam enters said interface at a predetermined angle;

said first light beam is a single light beam including components which strike said interface at various angles and having a predetermined light quantity distribution in a direction where an incidence angle to said interface changes; and said tilt measurement means measures said longitudinal tilt by utilizing at least a portion of said first light beam reflected at a portion of said measuring unit.

4. The measuring apparatus as set forth in claim 3, wherein said tilt measurement means measures said longitudinal tilt by utilizing a component of said first light beam which is outside a measuring range of said attenuated total reflection.

5. The measuring apparatus as set forth in claim 4, wherein said tilt measurement means measures said longitudinal tilt from a relationship between intensity of reflected light and a detected position, obtained for a portion of said first light beam, which is outside a measuring range of said attenuated total reflection, and in which a great change in a light quantity occurs due to said change in the incidence angle.

6. The measuring apparatus as set forth in claim 4, wherein said tilt measurement means causes a portion of said first light beam, which is outside a measuring range of said attenuated total reflection, to strike said interface as a dark line, and measures said longitudinal tilt, based on a position of said dark line included in said first light beam reflected at said interface, detected by said first photodetection means.

7. The measuring apparatus as set forth in claim 3, wherein said tilt measurement means comprises:

a converging lens for converging at least a portion of said first light beam reflected at a portion of said measuring unit; and second photodetection means for receiving said light beam converged by said converging lens and detecting position of said first light beam.

8. The measuring apparatus as set forth in claim 7, wherein said first light beam includes a plurality of polarized light components, and said second photodetection means receives a polarized light component, other than said predetermined polarized light component, of said first light beam and detects position of said first light beam.

9. The measuring apparatus asset forth in claim 7, wherein said tilt measurement means further comprises a second lens between said converging lens and said second photodetection means, and said converging lens, said second lens, and said second photodetection means are disposed with L, d0, d1, d2, f1, and f2 selected so that a relationship between a moved distance A of an angle of attenuated total reflection, expressed as $L \tan \theta + x$, and a spot movement quantity B of said first light beam on said second photodetection means, expressed as $\theta\{d1+d2-d1d2/f2-d0(d1/f1+d0/f1-d1d2/f1/f2-1+d2/f2)\}-x(d1/f1+d2/f1-d1d2/f1/f2-1+d2/f2)$, is A=B or A=−B , when f1 and f2 represent the focal lengths of said converging lens and said second lens, L represents the distance between the reflected position of said first light beam and said first photodetection means, d0 represents the distance between said reflected position and said converging lens, d1 represents the distance said converging lens and said second lens, d2 represents the distance between said second lens and said second photodetection means, x represents the shift quantity of said reflected position based on the shift quantity of said interface, and $\theta$ represents the longitudinal tilt of said interface.

10. The measuring apparatus as set forth in claim 9, wherein said converging lens, said second lens, and said second photodetection means are disposed so that the relationship between said distances L, d0, d1, and d2 and said focal lengths f1 and f2 becomes d1=f1, d2=f2, and d0=f1+L.

11. The measuring apparatus as set forth in either claim 1 or claim 2, wherein said tilt measurement means comprises second beam incidence means for making a second light beam, which differs from said first light beam, enter a portion of said measuring unit, and second photodetection means for receiving said second light beam reflected at said portion of said measuring unit and detecting position of said second light beam.

12. The measuring apparatus as set forth in claim 11, wherein said second light beam has a wavelength differing from that of said first light beam.

13. The measuring apparatus as set forth in claim 11, wherein said first light beam is a linearly polarized light beam of said predetermined polarized light component, and said second light beam is a linearly polarized light beam of a polarized light component differing from said first light beam.

14. The measuring apparatus as set forth in claim 3, wherein said portion of said measuring unit is a predetermined surface of said measuring unit which tilts corresponding to said longitudinal tilt of said interface.

15. The sensor as set forth in claim 14, wherein said predetermined surface is a reflecting surface provided near said one surface of said dielectric block on which said thin film layer is formed.

16. A measuring apparatus comprising:

a measuring unit equipped with a transparent dielectric block and a thin film layer formed on one surface of said dielectric block;

first beam incidence means for making a first light beam enter said dielectric block at various angles of incidence so that a condition for total internal reflection is satisfied at an interface between said dielectric block and said thin film layer; and first photodetection means for receiving a predetermined polarized light component of said first light beam totally reflected at said interface;

wherein said measuring unit is measured a plurality of times and a change in the state of attenuated total reflection during the plurality of measurements is detected;

and wherein said measuring apparatus further comprises:

tilt measurement means for measuring a longitudinal tilt and a transverse tilt of said interface which change said incidence angles during said plurality of measurements;

adjustment means for making adjustments to said measuring unit, said first beam incidence means, and/or said first photodetection means so that a shift of a received position of said first light beam on said first photodetection means resulting from said transverse tilt is corrected according to said transverse tilt measured by said tilt measurement means; and calculating means for obtaining a measured value in which errors due to said longitudinal tilt have been corrected according to said longitudinal tilt measured by said tilt measurement means.

17. A measuring apparatus comprising:

a measuring unit equipped with a transparent dielectric block and a thin film layer formed on one surface of said dielectric block;

first beam incidence means for making a first light beam enter said dielectric block at an angle of incidence so that a condition for total internal reflection is satisfied at an interface between said dielectric block and said thin film layer; and first photodetection means for receiving a predetermined polarized light component of said first light beam totally reflected at said interface;

wherein said measuring unit is measured a plurality of times and a change in the state of attenuated total reflection during the plurality of measurements is detected;

and wherein said measuring apparatus further comprises:

tilt measurement means for measuring a longitudinal tilt and a transverse tilt of said interface which change said incidence angles during said plurality of measurements; and adjustment means for making adjustments to said measuring unit, said first beam incidence means, and/or said first photodetection means so that a shift of a received position of said first light beam on said first photodetection means resulting from said transverse tilt, and errors due to said longitudinal tilt, are corrected according to said longitudinal and transverse tilts measured by said tilt measurement means.

18. The measuring apparatus as set forth in either claim 16 or 17, wherein said first beam incidence means is constructed to cause said first light beam to enter said interface at various angles of incidence;

said first photodetection means is constructed to measure a state of attenuated total reflection which occurs when said first light beam enters said interface at a predetermined angle;

said first light beam is a single light beam including components which strike said interface at various angles and having a predetermined light quantity distribution in a direction where an incidence angle to said interface changes; and said tilt measurement means comprises:

a converging lens for converging at least a portion of said first light beam reflected at a portion of said measuring unit; and two-dimensional photodetection means for receiving the light beam converged by said converging lens and detecting position of said first light beam.

19. The measuring apparatus as set forth in either claim 16 or 17, wherein said tilt measurement means comprises second beam incidence means for making a second light beam, which differs from said first light beam, enter a portion of said measuring unit, and two-dimensional photodetection means for receiving said second light beam reflected at said portion of said measuring unit and detecting position of said second light beam.

20. The measuring apparatus as set forth in claim 19, wherein said second light beam has a wavelength differing from that of said first light beam.

21. The measuring apparatus as set forth in claim 19, wherein said first light beam is a linearly polarized light beam of said predetermined polarized light component, and said second light beam is a linearly polarized light beam of a polarized light component differing from said first light beam.

22. The measuring apparatus as set forth in claim 18, wherein said second photodetection means comprises a four-piece photodiode.

23. The measuring apparatus as set forth in claim 18, wherein said second photodetection means comprises a resistance photodetector.

24. The measuring apparatus as set forth in any claim 18, wherein said portion of said measuring unit is a predetermined surface of said measuring unit which tilts corresponding to the longitudinal and transverse tilts of said interface.

25. The measuring apparatus as set forth in claim 24, wherein said predetermined surface is a reflecting surface provided near said one surface of said dielectric body on which said thin film layer is formed.

26. The measuring apparatus as set forth in any one of claims 1, 2, 16, and 17, wherein said dielectric block is formed as a single block having a light entrance surface, a light exit surface, and said one surface on which said thin film layer is formed.

27. The measuring apparatus as set forth in any one of claims 1, 2, 16, and 17, wherein said dielectric block comprises a first portion having a light entrance surface and a light exit surface, and a second portion having said one surface on which said thin film layer is formed, and said first portion and said second portion are joined together through index-matching means.

* * * * *